(12) United States Patent
Corti

(10) Patent No.: US 12,037,381 B2
(45) Date of Patent: *Jul. 16, 2024

(54) ANTIBODIES THAT POTENTLY NEUTRALIZE HEPATITIS B VIRUS AND USES THEREOF

(71) Applicant: Humabs BioMed SA, Bellinzona (CH)

(72) Inventor: Davide Corti, Bellinzona (CH)

(73) Assignee: Humabs BioMed SA, Bellinzona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/867,466

(22) Filed: Jul. 18, 2022

(65) Prior Publication Data

US 2023/0303663 A1 Sep. 28, 2023

Related U.S. Application Data

(60) Continuation of application No. 16/864,087, filed on Apr. 30, 2020, now Pat. No. 11,390,664, which is a division of application No. 15/766,703, filed as application No. PCT/EP2016/074114 on Oct. 7, 2016, now Pat. No. 10,683,344.

(30) Foreign Application Priority Data

Oct. 7, 2015 (WO) ................ PCT/EP2015/001970

(51) Int. Cl.
| | | |
|---|---|---|
| C07K 16/08 | (2006.01) | |
| A61K 39/42 | (2006.01) | |
| A61P 31/14 | (2006.01) | |
| A61P 31/20 | (2006.01) | |
| C07K 14/005 | (2006.01) | |
| C07K 16/10 | (2006.01) | |
| A61K 39/00 | (2006.01) | |

(52) U.S. Cl.
CPC ............ *C07K 16/082* (2013.01); *A61K 39/42* (2013.01); *A61P 31/14* (2018.01); *A61P 31/20* (2018.01); *C07K 14/005* (2013.01); *C07K 16/10* (2013.01); *A61K 2039/505* (2013.01); *C07K 2317/21* (2013.01); *C07K 2317/33* (2013.01); *C07K 2317/34* (2013.01); *C07K 2317/76* (2013.01); *C12N 2730/10111* (2013.01)

(58) Field of Classification Search
None
See application file for complete search history.

(56) References Cited

U.S. PATENT DOCUMENTS

| | | | |
|---|---|---|---|
| 3,766,162 A | 10/1973 | Spector | |
| 3,791,932 A | 2/1974 | Schuurs et al. | |
| 3,817,837 A | 6/1974 | Rubenstein et al. | |
| 4,179,337 A | 12/1979 | Davis et al. | |
| 4,233,402 A | 11/1980 | Maggio et al. | |
| 4,495,285 A | 1/1985 | Shimizu et al. | |
| 4,609,546 A | 9/1986 | Hiratani | |
| 4,676,980 A | 6/1987 | Segal et al. | |
| 4,766,106 A | 8/1988 | Katre et al. | |
| 4,831,175 A | 5/1989 | Gansow et al. | |
| 5,595,721 A | 1/1997 | Kaminski et al. | |
| 10,683,344 B2* | 6/2020 | Corti ................... | C07K 16/082 |
| 11,390,664 B2* | 7/2022 | Corti ................... | C07K 14/005 |
| 2005/0163783 A1 | 7/2005 | Braslawsky et al. | |
| 2015/0299289 A1 | 10/2015 | Urban et al. | |

FOREIGN PATENT DOCUMENTS

| | | |
|---|---|---|
| JP | 6869968 B2 | 5/2021 |
| WO | 97/39029 A2 | 10/1997 |
| WO | 97/40164 A1 | 10/1997 |
| WO | 98/29442 A1 | 7/1998 |
| WO | 00/52031 A2 | 9/2000 |
| WO | 00/52473 A2 | 9/2000 |
| WO | 2004/076677 A2 | 9/2004 |
| WO | 2006/076640 A1 | 7/2006 |
| WO | 2008/143954 A2 | 11/2008 |
| WO | 2009/069917 A1 | 6/2009 |
| WO | 2010/046775 A2 | 4/2010 |
| WO | 2014/032176 A1 | 3/2014 |
| WO | 2015/107126 A1 | 7/2015 |

OTHER PUBLICATIONS

Cerino et al. (PLOS, 2015, p. 1-10).*
International Search Report and Written Opinion, mailed Feb. 8, 2017, for International Application No. PCT/EP2016/074114, 17 pages.
Martin et al., "Selection of Ig μHeavy Chains by Complementarity-Determining Region 3 Length and Amino Acid Composition," *The Journal of Immunology 171*:4663-4671, 2003 (10 pages).
Qiu et al., "Identification and Characterization of a C(K/R)TC Motif as a Common Epitope Present in All Subtypes of Hepatitis B Surface Antigen," *The Journal of Immunology* 156(9):3350-3356, 1996.
Shirazi et al., "Monoclonal antibodies to various epitopes of hepatitis B surface antigen inhibit hepatitis B virus infection," *Journal of Gastroenterology and Hepatology* 29(5): 1083-1091, 2014.
Sureau et al., "Production of Infectious Hepatitis Delta Virus In Vitro and Neutralization with Antibodies Directed against Hepatitis B Virus Pre-S Antigens," *Journal of Virology* 66(2): 1241-1245, 1992.

(Continued)

*Primary Examiner* — Agnieszka Boesen
(74) *Attorney, Agent, or Firm* — Fox Rothschild LLP

(57) ABSTRACT

The present invention relates to antibodies, and antigen binding fragments thereof, that bind to the antigenic loop region of hepatitis B surface antigen (HBsAg) and potently neutralize infection of both hepatitis B virus (HBV) and hepatitis delta virus (HDV). The invention also relates to epitopes to which the antibodies and antigen binding fragments bind, as well as to nucleic acids that encode and cells that produce such antibodies and antibody fragments. In addition, the invention relates to the use of the antibodies and antibody fragments of the invention in the diagnosis, prophylaxis and treatment of hepatitis B and hepatitis D.

20 Claims, 39 Drawing Sheets

Specification includes a Sequence Listing.

(56) References Cited

OTHER PUBLICATIONS

Traggiai et al., "An efficient method to make human monoclonal antibodies from memory B cells: potent neutralization of SARS coronavirus," *Nature Medicine* 10(8):871-875, 2004.

Wedemeyer et al., "Update on the Management of HBV-HDV Coinfection," *Current Hepatitis Reports* 11(2):95-101, 2012.

Zubkin et al., "Strategy of Vaccination Against HBV-infection in Hemodialysis Patients with 'Isolated' HBcAb," *International Journal of Infectious Diseases* 10:S42-S43, 2006. (abstract only).

Jaoudé et al., "Role of the Antigenic Loop of the Hepatitis B Virus Envelope Proteins in Infectivity of Hepatitis Delta Virus," Journal of Virology 79(16): 10460-10466, Aug. 2005.

* cited by examiner

```
                         20                    40                          60
                         |                     |                           |
HBV-D J02203 (D, ayw3)   QGMLPVCPLIPGSTTSTGPCRTCMTTAQGTSMYPSCCCTKPSDGNCTCIPIPSSWAFGKFLWEWASARFSW 72
FJ899792.1 (D, adw2)     ..............G...................................................  72
HBV-A AM282986 sAg       ..............TT.....L.K.T.P..N...F...............A.Y...........V..  72
HBV-B1 Japan D23678 sAg  .............T.......L.K.T.P.....F................A.Y...........V..  72
HBV-C1 Cambodia AB117758 sAg .....................L.K.T.P.....F.......T........AR............V..  72
HBV-E Ghana AB205192 sAg ...............T.....L.T.T.L.....F....S...........A.Y..............  72
HBV-F4 Brazil X69798 sAg ...............T.....L.K.T.L.....F....S............L.Y.............  72
HBV-G USA AF160501 sAg   .....................L.K.T.P..N..................A.Y...........V..  72
HBV-H Nicaragua AY090454 sAg ...........T.........L.K.T.L.....F..................Y...........V..  72
HBV-I Vietnam AF241409 sAg ...........T.........L.K.T.P..N...F...............A.Y..............  72
HBV-J Borneo AB486012 sAg ...........T.........L.K.T.L..........................A...........V..  72
```

FIG. 5

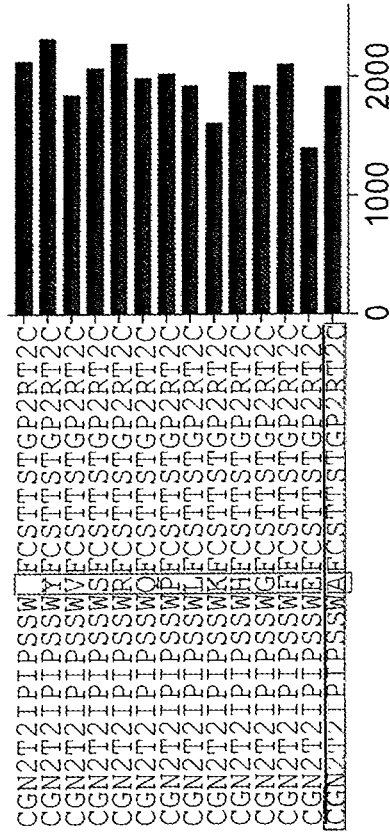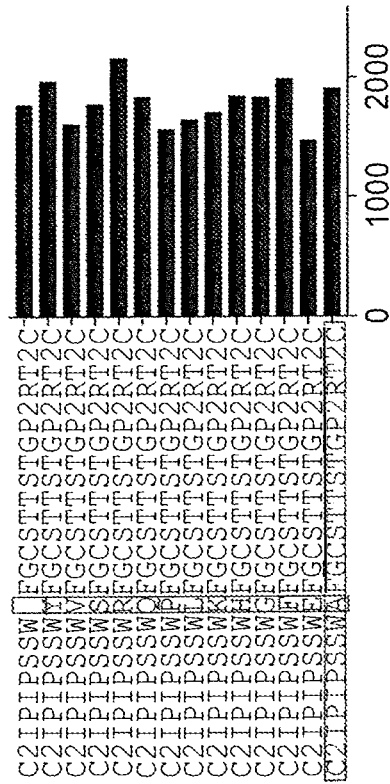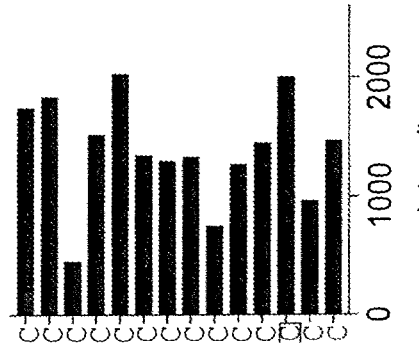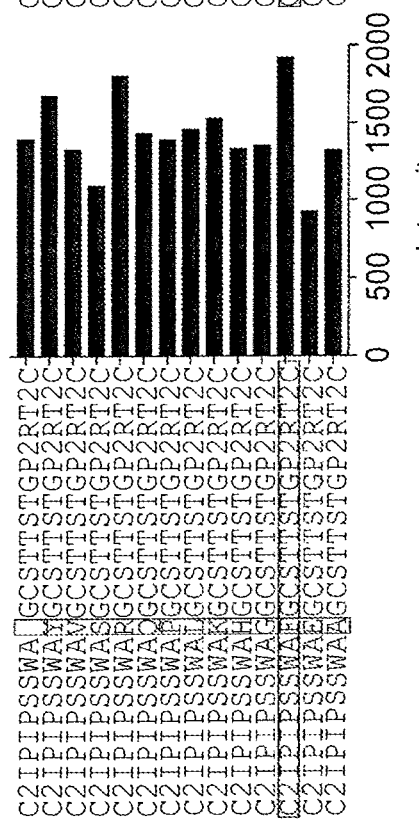
FIG. 18 (continued)

FIG. 20

| Variant name | VH | VL | Binding to HBsAg (adw) |
|---|---|---|---|
| HBC34 | WT | WT | + |
| HBC34-V1 | W107F | WT | +/- |
| HBC34-V2 | W107F | W107A | - |
| HBC34-V3 | W107F | W107F | +/- |
| HBC34-V4 | M115I | W107F | +/- |
| HBC34-V5 | W107A | W107F | - |
| HBC34-V6 | M115L | W107F | +/~ |
| HBC34-V7 | WT | W107F | + |
| HBC34-V8 | W107A/M115A | W107F | - |
| HBC34-V9 | W107A/M115A | W107A | - |
| HBC34-V10 | W107A/M115A | WT | - |
| HBC34-V11 | M115I | WT | +/~ |
| HBC34-V12 | W107A | WT | - |
| HBC34-V13 | M115L | WT | + |
| HBC34-V15 | WT | W107A | +/~ |
| HBC34-V16 | M115L | W107A | +/- |
| HBC34-V17 | W107A | W107A | - |
| HBC34-V18 | M115I | W107A | +/- |

FIG. 21

| Variant name | VH | VL | Binding EC50 | Fold change (mutant/wt) | Productivity (µg/ml) | Fold change (mutant/wt) |
|---|---|---|---|---|---|---|
| HBC34 | WT | WT | 7,7 | 1,0 | 318 | 1,00 |
| HBC34-V1 | W107F | WT | 12,8 | 1,6 | 79 | 0,25 |
| HBC34-V3 | W107F | W107F | 69,4 | 9,0 | 64 | 0,20 |
| HBC34-V4 | M115I | W107F | 15,7 | 2,0 | 112 | 0,35 |
| HBC34-V6 | M115L | W107F | 12,7 | 1,6 | 103 | 0,32 |
| HBC34-V7 | WT | W107F | 10,4 | 1,3 | 533 | 1,68 |
| HBC34-V11 | M115I | WT | 10,8 | 1,4 | 195 | 0,61 |
| HBC34-V13 | M115L | WT | 8,0 | 1,0 | 106 | 0,33 |

| Variant name | VH modification | VL modification | EC50 | Fold change (mutant/wt) | Productivity (µg/ml) | Fold change (mutant/wt) |
|---|---|---|---|---|---|---|
| HBC34 | WT | WT | 13,3 | 1,0 | 197 | 1,00 |
| HBC34-V6 | M115L | W107F | 16,5 | 1,2 | 35 | 0,18 |
| HBC34-V7 | WT | W107F | 18,6 | 1,4 | 232 | 1,18 |
| HBC34-V13 | M115L | WT | 12,0 | 0,9 | 46 | 0,23 |
| HBC34-V19 | M115L/FR124GL | WT | 18,9 | 1,4 | 37 | 0,19 |
| HBC34-V20 | M115L/FR1234GL | WT | 31,8 | 2,4 | 145 | 0,73 |
| HBC34-V21 | M115L/FR124GL | W107F | 607 | 45,6 | 28 | 0,14 |
| HBC34-V22 | M115L/FR1234GL | W107F | 419 | 31,4 | 110 | 0,56 |
| HBC34-V23 | WT | W107F/FR1234GL/CDR2Y66 | 20,1 | 1,5 | 184 | 0,93 |
| HBC34-V24 | M115L | W107F/FR1234GL/CDR2Y66 | 24,0 | 1,8 | 27 | 0,14 |
| HBC34-V25 | M115L/FR124GL | W107F/FR1234GL/CDR2Y66 | 492 | 36,9 | 26 | 0,13 |
| HBC34-V26 | M115L/FR1234GL | W107F/FR1234GL/CDR2Y66 | 125 | 9,4 | 93 | 0,47 |
| HBC34-V27 | WT | W107F/FR1234GL | 2022 | 151,8 | 270 | 1,37 |
| HBC34-V28 | M115L | W107F/FR1234GL | 2037 | 152,9 | 29 | 0,15 |
| HBC34-V29 | M115L/FR124GL | W107F/FR1234GL | >10000 | ND | 36 | 0,18 |
| HBC34-V30 | M115L/FR1234GL | W107F/FR1234GL | >10000 | ND | 101 | 0,51 |

ANTIBODIES THAT POTENTLY NEUTRALIZE HEPATITIS B VIRUS AND USES THEREOF

REFERENCE TO AN ELECTRONIC SEQUENCE LISTING

The contents of the electronic sequence listing (470082_405C2_SEQUENCE_LISTING.xml; Size: 111 kilobytes; and Date of Creation: Jun. 7, 2023) is herein incorporated by reference in its entirety.

The present invention relates to the field of antibodies against hepatitis B virus (HBV) and against hepatitis delta virus (HDV) and uses thereof. The potent anti hepatitis B antibodies of the present invention bind to an epitope located in the antigenic loop region of the S domain of the HBV envelope proteins (HBsAg), as identified in the present invention. The invention also relates to nucleic acids that encode and immortalized B cells and cultured plasma cells that produce such antibodies and antibody fragments. In addition, the invention relates to the use of the antibodies and antibody fragments of the invention in screening methods as well as in the diagnosis, prophylaxis and treatment of diseases, in particular hepatitis B and hepatitis D.

The hepatitis B virus (HBV) consists of (i) an envelope containing three related surface proteins (hepatitis B surface antigen, HBsAg) and lipid and (ii) an icosahedral nucleocapsid enclosing the viral DNA genome and DNA polymerase. The HBV capsid is formed in the cytosol of the infected cell during packaging of an RNA pregenome replication complex and gains the ability to bud during synthesis of the viral DNA genome by reverse transcription of the pregenome in the lumen of the particle. The three HBV envelope proteins S-HBsAg, M-HBsAg, and L-HBsAg shape a complex transmembrane fold at the endoplasmic reticulum, and form disulfide-linked homo- and heterodimers. During budding at an intracellular membrane, a short linear domain in the cytosolic preS region interacts with binding sites on the capsid surface. The virions are subsequently secreted into the blood. In addition, the surface proteins can bud in the absence of capsids and form subviral particles (SVP's) which are also secreted in 3-4 log excess over virions. High level of HBsAg can exhaust HBsAg-specific T-cell response, and is proposed as an important factor for viral immunotolerance in patients with chronic hepatitis B (CHB) (Chisari F V, Isogawa M, Wieland S F, Pathologie Biologie, 2010; 58:258-66).

Hepatitis B virus causes potentially life-threatening acute and chronic liver infections. Acute hepatitis B is characterized by viremia, with or without symptoms, with the risk of fulminant hepatitis occurrence (Liang T J, Block T M, McMahon B J, Ghany M G, Urban S, Guo J T, Locarnini S, Zoulim F, Chang K M, Lok A S. Present and future therapies of hepatitis B: From discovery to cure. Hepatology. 2015 Aug. 3. doi: 10.1002/hep.28025. [Epub ahead of print]). Despite an efficacious vaccine against hepatitis B is available since 1982, WHO reports that 240 million people are chronically infected with hepatitis B and more than 780 000 people die every year due to hepatitis B complications. Approximately one third of chronic hepatitis B (CHB) patients develop cirrhosis, liver failure and hepatocellular carcinoma, accounting for 600,000 deaths per year (Liang T J, Block T M, McMahon B J, Ghany M G, Urban S, Guo J T, Locarnini S, Zoulim F, Chang K M, Lok A S. Present and future therapies of hepatitis B: From discovery to cure. Hepatology. 2015 Aug. 3. doi: 10.1002/hep.28025. [Epub ahead of print]).

The currently available treatments for chronic hepatitis B include (pegylated) interferon-alpha (IFN-α or pegIFN-α) and nucleos(t)ide analogue Direct Acting Antivirals (DAAs) that inhibit the hepatitis B virus (HBV) DNA polymerase ("polymerase inhibitors"). Polymerase inhibitors include Lamivudine, Adefovir, Entcavir, Telbivudine and Tenofovir. Polymerase inhibitors (Lamivudine, Adefovir, Entecavir, Telbivudine, Tenofovir) suppress the reverse transcriptase function of the HBV DNA polymerase and therefore interfere with the synthesis of viral DNA from pregenomic RNA. This treatment does not prevent viral spread, formation of cccDNA and does not affect HBsAg release. Moreover, polymerase inhibitors limit disease progression but rarely clear the virus. Thus, viral relapse is commonly observed after stopping the treatment and, therefore, polymerase inhibitors should be used for the lifetime. In addition, drug-resistant mutants emerge after prolonged treatment. PEG-IFN-α inhibits HBV indirectly through immune modulatory effects and directly by reducing steady-state levels of HBV transcripts (increased acetylation of cccDNA-bound histones). However, PEG-IFN-α has limited efficacy and causes serious side effects.

While pegIFN-α is effective in approximately one-third of the treated patients, the polymerase inhibitors significantly reduce viral load in the vast majority of those treated (Timothy M. Block, Robert Gish, Haitao Guo, Anand Mehta, Andrea Cuconati, W. Thomas London, Ju-Tao Guo Chronic hepatitis B: What should be the goal for new therapies? Antiviral Research 98 (2013) 27-34). Interferon α is associated with many adverse reactions and cannot be used in patients with advanced cirrhosis or medical/psychiatric contraindications (Liang T J, Block T M, McMahon B J, Ghany M G, Urban S, Guo J T, Locarnini S, Zoulim F, Chang K M, Lok A S. Present and future therapies of hepatitis B: From discovery to cure. Hepatology. 2015 Aug. 3. doi: 10.1002/hep.28025. [Epub ahead of print]). Although polymerase inhibitors such as entecarvir and tenofovir appear to have less adverse effects, rates of HBeAG seroconversion and HBsAg loss are low for those drugs. Therefore, most patients require often lifelong treatment with associated costs and risks of adverse reactions, drug resistance and non-adherence. Thus, the currently available treatment for chronic hepatitis B is still handicapped by various limitations and cannot be considered as curative. Therefore—although treatment for HBV has improved—HBV patients often require life-long therapies and cure is still a challenging goal. (Liang T J, Block T M, McMahon B J, Ghany M G, Urban S, Guo J T, Locarnini S, Zoulim F, Chang K M, Lok A S. Present and future therapies of hepatitis B: From discovery to cure. Hepatology. 2015 Aug. 3. doi: 10.1002/hep.28025. [Epub ahead of print]). The closest outcome to cure chronic hepatitis B (CHB) and an ideal endpoint of treatment would be to achieve a loss of hepatitis B surface antigen (HBsAg), which is, however, not yet achieved efficiently with the presently available treatments of chronic hepatitis B (for review see Gish R. G. et al., 2015, Antiviral Research 121:47-58).

Severely decompensated HBV patients with acute hepatitis or hepatocellular carcinoma are indicated for orthotopic liver transplantation (OLT). After OLT, the hepatitis B recurrence rate is >80% without prevention, while >90% of transplant recipients are clinically controlled with combined hepatitis B immunoglobulin (HBIG) and nucleos(t)ide analogue treatment. Hepatitis B immunoglobulins (HBIG) are polyclonal immunoglobulins purified from vaccinated donors. However, long-term HBIG administration is associated with several unresolved issues, including limited availability and extremely high cost (Takaki A, Yasunaka T, Yagi T. Molecular mechanism to control post-transplantation hepatitis B recurrence. Int J Mol Sci. 2015 Jul. 30; 16(8):17494-513). Moreover, extremely high doses have to be administered, namely 10 grams (containing 10,000 IU based on binding assays) are administered to the recipient during the transplant by intravenous infusion. Subsequently 2 grams are administered intravenously daily for 8 days and further infusions are given every 1-3 months to maintain anti-HBs serum levels above 100 IU/ml. Again, life-long treatment is required.

Even more severe complications are observed when coinfection or superinfection with hepatitis delta virus (HDV) occur. According to the WHO, hepatitis D infects about 15 million people worldwide. HDV is considered a subviral satellite because it can propagate only in the presence of HBV. HDV is one of the smallest animal viruses (40 nm), whereby its genome is only 1.6 kb and encodes for S and L HDAg. All other proteins needed for genome replication of HDV, including the RNA polymerase, are provided by the host cell and the HDV envelope is provided by HBV. In other words, HDV is a defective virus that requires coinfection with HBV for its replication since it utilizes the hepatitis B envelope proteins (HBsAg) as its own virion coat. When introduced into permissive cells, the HDV RNA genome replicates and associates with multiple copies of the HDV-encoded proteins to assemble a ribonucleoprotein (RNP) complex. The RNP is exported from the cell by the HBV envelope proteins, which are able to assemble lipoprotein vesicles that bud into the lumen of a pre-Golgi compartment before being secreted. Moreover, the HBV envelope proteins also provide a mechanism for the targeting of HDV to an uninfected cell, thereby ensuring the spread of HDV.

The complications caused by HDV include a greater likelihood of experiencing liver failure in acute infections and a rapid progression to liver cirrhosis, with an increased chance of developing liver cancer in chronic infections. In combination with hepatitis B virus, hepatitis D has the highest fatality rate of all the hepatitis infections, at 20% (Fattovich G, Giustina G, Christensen E, Pantalena M, Zagni I, Realdi G, Schalm S W. Influence of hepatitis delta virus infection on morbidity and mortality in compensated cirrhosis type B. Gut. 2000 March; 46(3):420-6). The only approved therapy for chronic HDV infection is interferon-alpha. However, treatment of HDV with interferon-alpha is relatively inefficient and not well-tolerated. Treatment with interferon-alpha results in sustained virological response six months post-treatment in one fourth of the patients. Also, nucleos(t)ide analogs (NAs) have been widely tested in hepatitis delta, but they appear to be ineffective. Combination treatment of NAs with interferon also proved to be disappointing and so there is a need for novel therapeutic options (Zaigham Abbas, Minaam Abbas Management of hepatitis delta: Need for novel therapeutic Options. World J Gastroenterol 2015 Aug. 28; 21(32): 9461-9465).

In view of the above, it is the object of the present invention provide an antibody-based product, which is capable of neutralizing both, hepatitis B virus (HBV) and hepatitis delta virus (HDV). That enables an improved prevention and treatment of hepatitis B. Moreover, no treatment is presently available for hepatitis D and, thus, it is also an object of the present invention to provide an antibody-based product for prevention and treatment of hepatitis D.

It is furthermore an object of the present invention to provide an antibody-based product, which enables a better treatment of chronic hepatitis B. To this end, it is advantageous if one single antibody-based product acts in different ways by (i) potently neutralizing HBV, (ii) promoting clearance of HBsAg and HBV and (iii) inducing seroconversion, i.e. an immune response to the virus. Moreover, antibodies may advantageously also promote an improved presentation of the antigen, thereby facilitating the restoration of an anti-HBV T-cell response.

In addition, it is an object of the present invention to provide an antibody, or an antigen-binding fragment thereof, which binds to different—preferably all known—genotypes of hepatitis B virus surface antigen and to different—preferably all known—infectious mutants of hepatitis B virus surface antigen. In summary, it is the object of the present invention to provide improved antibodies, or antigen binding fragments thereof, as well as related nucleic acid molecules, vectors and cells and pharmaceutical compositions, which overcome the above discussed drawbacks of the prior art.

The object underlying the present invention is solved by the subject-matter set out below and in the appended claims.

In the following, the elements of the present invention will be described. These elements are listed with specific embodiments, however, it should be understood that they may be combined in any manner and in any number to create additional embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Unless defined otherwise, all technical and scientific terms used herein have the same meaning as commonly understood by one of ordinary skill in the art.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

As used herein, the terms "peptide", "polypeptide", and "protein" and variations of these terms refer to a molecule, in particular a peptide, oligopeptide, polypeptide or protein including fusion protein, respectively, comprising at least two amino acids joined to each other by a normal peptide bond, or by a modified peptide bond, such as for example in the cases of isosteric peptides. For example, a peptide, polypeptide or protein is preferably composed of amino acids selected from the 20 amino acids defined by the genetic code, linked to each other by a normal peptide bond ("classical" polypeptide). A peptide, polypeptide or protein can be composed of L-amino acids and/or D-amino acids. In particular, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein may comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

As used herein a "(poly)peptide" comprises a single chain of amino acid monomers linked by peptide bonds as explained above. A "protein", as used herein, comprises one or more, e.g. 1, 2, 3, 4, 5, 6, 7, 8, 9 or 10 (poly)peptides, i.e. one or more chains of amino acid monomers linked by peptide bonds as explained above. Preferably, a protein according to the present invention comprises 1, 2, 3, or 4 polypeptides.

The term "recombinant", as used herein (e.g. a recombinant antibody, a recombinant protein, a recombinant nucleic acid etc.), refers to any molecule (antibody, protein, nucleic acid etc.) which is prepared, expressed, created or isolated by recombinant means, and which is not naturally occurring.

As used herein, the terms "nucleic acid", "nucleic acid molecule" and "polynucleotide" are used interchangeably and are intended to include DNA molecules and RNA molecules. A nucleic acid molecule may be single-stranded or double-stranded, but preferably is double-stranded DNA.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The terms "binding" and "specifically binding" and similar reference do not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

As used herein, the term "sequence variant" refers to any sequence having one or more alterations in comparison to a reference sequence, whereby a reference sequence is any of the sequences listed in the "Table of Sequences and SEQ ID Numbers" (sequence listing), i.e. SEQ ID NO: 1 to SEQ ID NO: 88. Thus, the term "sequence variant" includes nucleotide sequence variants and amino acid sequence variants. For a sequence variant in the context of a nucleotide sequence, the reference sequence is also a nucleotide sequence, whereas for sequence variant in the context of an amino acid sequence, the reference sequence is also an amino acid sequence. A "sequence variant" as used herein is at least 80%, preferably at least 85%, more preferably at least 90%, even more preferably at least 95% and particularly preferably at least 98% or 99% identical to the reference sequence. Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; http://www.ncbi.nlm.nih.gov/) [Blosum 62 matrix; gap open penalty=11 and gap extension penalty=1].

A "sequence variant" in the context of a nucleic acid (nucleotide) sequence has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "sequence variant" of a nucleotide sequence can either result in a change in the respective reference amino acid sequence, i.e. in an amino acid "sequence variant" or not. Nucleotide sequence variants, which do not result in amino acid sequence variants are preferred (silent mutations). However, nucleotide sequence variants leading to "non-silent" mutations are also within the scope, in particular such nucleotide sequence variants, which result in an amino acid sequence, which is at least 80%, preferably at least 85%, more preferably at least 90%, even more preferably at least 95% and particularly preferably at least 98% or 99% identical to the reference amino acid sequence.

A "sequence variant" in the context of an amino acid sequence has an altered sequence in which one or more of the amino acids is deleted, substituted or inserted in comparison to the reference amino acid sequence. As a result of the alterations, such a sequence variant has an amino acid sequence which is at least 80%, preferably at least 85%, more preferably at least 90%, even more preferably at least 95% and particularly preferably at least 98% or 99% identical to the reference amino acid sequence. For example, per 100 amino acids of the reference sequence a variant sequence has no more than 10 alterations, i.e. any combination of deletions, insertions or substitutions, is "at least 90% identical" to the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme. Importantly, the alterations in the sequence variants do not abolish the functionality of the respective reference sequence, in the present case, for example the functionality of a sequence of an antibody, or antigen binding fragment thereof, to bind to the same epitope and/or to sufficiently neutralize infection of HBV and HDV. Guidance in determining which nucleotides and amino acid residues, respectively, may be substituted, inserted or deleted without abolishing such functionality can be found by using computer programs well known in the art.

As used herein, a nucleic acid sequence or an amino acid sequence "derived from" a designated nucleic acid, peptide, polypeptide or protein refers to the origin of the nucleic acid, peptide, polypeptide or protein. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g. a corresponding genomic sequence. A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

The present invention is based, amongst other findings, on the discovery and isolation of antibodies that are highly potent in neutralizing hepatitis B and hepatitis delta viruses, as well as of epitopes to which the antibodies of the invention bind. Such antibodies are desirable, as only small quantities of the antibodies are required in order to neutralize hepatitis B virus. Moreover, there is currently no treatment available for hepatitis D. The antibodies according to the present invention are highly effective in preventing as well as treating or attenuating HBV and HDV. Moreover, the antibodies according to the present invention bind to different—preferably all known—genotypes of hepatitis B virus surface antigen and to different—preferably all known—infectious mutants of hepatitis B virus surface antigen.

Antibodies and Antigen-Binding Fragments Thereof.

In a first aspect the present invention provides an isolated antibody, or an antigen binding fragment thereof, that binds to the antigenic loop region of HBsAg and neutralizes infection with hepatitis B virus and hepatitis delta virus.

As used herein, the term "antibody" encompasses various forms of antibodies including, without being limited to, whole antibodies, antibody fragments, in particular antigen binding fragments, human antibodies, chimeric antibodies, humanized antibodies, recombinant antibodies and genetically engineered antibodies (variant or mutant antibodies) as long as the characteristic properties according to the invention are retained. Human antibodies and monoclonal antibodies are preferred and especially preferred are human monoclonal antibodies, in particular as recombinant human monoclonal antibodies.

Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 3340). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). Preferably, human monoclonal antibodies are prepared by using improved EBV-B cell immortalization as described in Traggiai E, Becker S, Subbarao K, Kolesnikova L, Uematsu Y, Gismondo M R, Murphy B R, Rappuoli R, Lanzavecchia A. (2004): An efficient method to make human monoclonal antibodies from memory B cells: potent neutralization of SARS coronavirus. Nat Med. 10(8):871-5. The term "human antibody" as used herein also comprises such antibodies which are modified, e.g. in the variable region, to generate the properties according to the invention as described herein. As used herein, the term "variable region" (variable region of a light chain ($V_L$), variable region of a heavy chain ($V_H$)) denotes each of the pair of light and heavy chains which is involved directly in binding the antibody to the antigen.

Antibodies of the invention can be of any isotype (e.g., IgA, IgG, IgM i.e. an α, γ or μ heavy chain), but will preferably be IgG. Within the IgG isotype, antibodies may be IgG1, IgG2, IgG3 or IgG4 subclass, whereby IgG1 is preferred. Antibodies of the invention may have a κ or a Δ light chain. HBsAg-specific antibodies of the IgG-type may advantageously also block the release of HBV and HBsAg from infected cells—based on antigen-independent uptake of IgG through FcRN-IgG receptors into hepatocytes. Therefore, HBsAg-specific antibodies of the IgG-type can bind intracellularly and thereby block the release of HBV virions and HBsAg.

Preferably, the antibody according to the present invention, or the antigen binding fragment thereof, is a purified antibody, a single chain antibody, Fab, Fab', F(ab')2, Fv or scFv.

The antibodies of the invention may thus preferably be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv. Although the specification, including the claims, may, in some places, refer explicitly to antigen binding fragment(s), antibody fragment(s), variant(s) and/or derivative(s) of antibodies, it is understood that the term "antibody" or "antibody of the invention"

includes all categories of antibodies, namely, antigen binding fragment(s), antibody fragment(s), variant(s) and derivative(s) of antibodies.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fabs, bispecific scFv, and diabodies (Holliger and Hudson, 2005, Nature Biotechnology 9: 1126-1136).

Antibodies according to the present invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies according to the present invention may be immunogenic in human and/or in non-human (or heterologous) hosts e.g., in mice. For example, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

The antibody, and the antigen binding fragment thereof, according to the present invention binds to the antigenic loop region of HBsAg. The envelope of the hepatitis B virus contains three "HBV envelope proteins" (also known as "HBsAg", "hepatitis B surface antigen"): S protein (for "small", also referred to as S-HBsAg), M protein (for "middle", also referred to as M-HBsAg) and L protein (for "large", also referred to as L-HBsAg). S-HBsAg, M-HBsAg and L-HBsAg share the same C-terminal extremity (also referred to as "S domain", 226 amino acids), which corresponds to the S protein (S-HBsAg) and which is crucial for virus assembly and infectivity. S-HBsAg, M-HBsAg and L-HBsAg are synthesized in the endoplasmic reticulum (ER), assembled, and secreted as particles through the Golgi apparatus. The S domain comprises four predicted transmembrane (TM) domains, whereby both, the N-terminus as well as the C-terminus of the S domain are exposed to the lumen. The transmembrane domains TM1 and TM2 are both necessary for cotranslational protein integration into the ER membrane and the transmembrane domains TM3 and TM4 are located in the C-terminal third of the S domain. The "antigenic loop region" of HBsAg is located between the predicted TMs and TM4 transmembrane domains of the S domain of HBsAg, whereby the antigenic loop region comprises amino acids 101-172 of the S domain, which contains 226 amino acids in total (Salisse J. and Sureau C., 2009, Journal of Virology 83: 9321-9328). It is important to note that a determinant of infectivity resides in the antigenic loop region of HBV envelope proteins. In particular, residues between 119 and 125 of the HBsAg contained a CXXC motif, which had been demonstrated to be the most important sequence required for the infectivity of HBV and HDV (Jaoude G A, Sureau C, Journal of Virology, 2005; 79:10460-6).

When it is herein referred to positions in the amino acid sequence of the S domain of HBsAg, it is referred to an amino acid sequence as set forth in SEQ ID NO: 3 (shown below) or to natural or artificial sequence variants thereof.

```
MENITSGFLGPLLVLQAGFFLLTRILTIPQSLDSWWTSLNFLGGTTVCLGQ

NSQSPTSNHSPTSCPPTCPGYRWMCLRRFIIFLFILLLCLIFLLVLLDYQG

MLPVCPLIPGSSTTSTGPCRTCMTTAQGTSMYPSCCCTKPSDGNCTCIPIP

SSWAFGKFLWEWASARFSWLSLLVPFVQWFVGLSPTVWLSVIWMMWYWGPS

LYSILSPFLPLLPIFFCLWVYI
(SEQ ID NO: 3; amino acids 101-172 are shown
underlined)
```

For example, the expression "amino acids 101-172 of the S domain" refers to the amino acid residues from positions 101-172 of the polypeptide according to SEQ ID NO: 3. However, a person skilled in the art understands that mutations or variations (including, but not limited to, substitution, deletion and/or addition, for example, HBsAg of a different genotype or a different HBsAg mutant as described herein) may occur naturally in the amino acid sequence of the S domain of HBsAg or be introduced artificially into the amino acid sequence of the S domain of HBsAg without affecting its biological properties. Therefore, in the invention, the term "S domain of HBsAg" intends to comprise all such polypeptides, for example, including the polypeptide according to SEQ ID NO: 3 and its natural or artificial mutants. In addition, when sequence fragments of the S domain of HBsAg are described herein (e.g. amino acids 101-172 or amino acids 120-130 of the S domain of HBsAg), they include not only the corresponding sequence fragments of SEQ ID NO: 3, but also the corresponding sequence fragments of its natural or artificial mutants. For example, the expression "amino acid residues from positions 101-172 of the S domain of HBsAg" comprises amino acid residues from positions 101-172 of SEQ ID NO: 3 and the corresponding fragments of its mutants (natural or artificial mutants). According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity.

The M protein (M-HBsAg) corresponds to the S protein extended by an N-terminal domain of 55 amino acids called "pre-S2". The L protein (L-HBsAg) corresponds to the M protein extended by an N-terminal domain of 108 amino acids called "pre-S1" (genotype D). The pre-S1 and pre-S2 domains of the L protein can be present either at the inner face of viral particles (on the cytoplasmic side of the ER), playing a crucial role in virus assembly, or on the outer face (on the luminal side of the ER), available for the interaction with target cells and necessary for viral infectivity. Moreover, HBV surface proteins (HBsAgs) are not only incorporated into virion envelopes but also spontaneously bud from ER-Golgi intermediate compartment membranes to form empty "subviral particles" (SVPs) that are released from the cell by secretion.

Since all three HBV envelope proteins S-HBsAg, M-HBsAg and L-HBsAg comprise the S domain, all three HBV envelope proteins S-HBsAg, M-HBsAg and L-HBsAg also comprise the "antigenic loop region". Accordingly, an antibody, or an antigen binding fragment thereof, according to the present invention, which neutralizes HBV and binds to the antigenic loop region of HBsAg, binds to all three HBV envelope proteins S-HBsAg, M-HBsAg and L-HBsAg.

Moreover, an antibody, or an antigen binding fragment thereof, according to the present invention, neutralizes infection with hepatitis B virus and hepatitis delta virus. In other words, the antibody, or the antigen binding fragment thereof, according to the present invention, reduces viral infectivity of hepatitis B virus and hepatitis delta virus.

To study and quantitate virus infectivity (or "neutralization") in the laboratory the person skilled in the art knows various standard "neutralization assays". For a neutralization assay animal viruses are typically propagated in cells and/or cell lines. In the context of the present invention a neutralization assay is preferred, wherein cultured cells are incubated with a fixed amount of HBV or HDV in the presence (or absence) of the antibody to be tested. As a readout the levels of hepatitis B surface antigen (HBsAg) or hepatitis B e antigen (HBeAg) secreted into the cell culture supernatant may be used and/or HBcAg staining may be assessed. For HDV, for example delta antigen immunofluorescence staining may be assessed.

In a preferred embodiment of a HBV neutralization assay, cultured cells, for example HepaRG cells, in particular differentiated HepaRG cells, are incubated with a fixed amount of HBV in the presence or absence of the antibody to be tested, for example for 16 hours at 37° C. That incubation is preferably performed in a medium (e.g. supplemented with 4% PEG 8000). After incubation, cells may be washed and further cultivated. To measure virus infectivity, the levels of hepatitis B surface antigen (HBsAg) and hepatitis B e antigen (HBeAg) secreted into the culture supernatant, e.g. from day 7 to day 11 post-infection, may be determined by enzyme-linked immunosorbent assay (ELISA).

Additionally, HBcAg staining may be assessed in an immunofluorescence assay. In a preferred embodiment of a HDV neutralization assay essentially the same assay as for HBV may be used, with the difference that sera from HDV carriers may be used as HDV infection inoculum on differentiated HepaRg cells (instead of HBV). For detection, delta antigen immunofluorescence staining may be used as a readout.

The antibody and antigen binding fragment of the invention have high neutralizing potency. The concentration of the antibody of the invention required for 50% neutralization of hepatitis B virus (HBV) and hepatitis delta virus (HDV), is, for example, about 10 µg/ml or less. Preferably, the concentration of the antibody of the invention required for 50% neutralization of HBV and HDV is about 5 µg/ml, more preferably the concentration of the antibody of the invention required for 50% neutralization of HBV and HDV is about 1 µg/ml, even more preferably, the concentration of the antibody of the invention required for 50% neutralization of HBV and HDV is about 750 ng/ml. Most preferably, the concentration of the antibody of the invention required for 50% neutralization of HBV and HDV is 500 ng/ml or less, e.g. 450, 400, 350, 300, 250, 200, 175, 150, 125, 100, 90, 80, 70, 60 or about 50 ng/ml or less. This means that only low concentrations of the antibody are required for 50% neutralization of HBV and HDV. Specificity and potency can be measured using standard assays as known to one of skill in the art.

The antibody, or the antigen binding fragment thereof, according to the present invention, which potently neutralizes both, HBV and HDV, is useful in the prevention and treatment of hepatitis B and hepatitis D. In this context it is of note that infection with HDV typically occurs simultaneously or subsequently to infection with HBV (inoculation with HDV in the absence of HBV does not cause hepatitis D since HDV requires the support of HBV for its own replication) and hepatitis D is typically observed in chronic HBV carriers.

Preferably, the antibody according to the present invention, or an antigen binding fragment thereof, promotes clearance of HBsAg and HBV. In particular, the antibody according to the present invention, or an antigen binding fragment thereof, promotes clearance of both, HBV and subviral particles of hepatitis B virus (SVP's). Clearance of HBsAg or of subviral particles may be assessed by measuring the level of HBsAg for example in a blood sample, e.g. from a hepatitis B patient. Similarly, clearance of HBV may be assessed by measuring the level of HBV for example in a blood sample, e.g. from a hepatitis B patient.

In the sera of patients infected with HBV, in addition to infectious particles (HBV), there is typically an excess (typically 1,000- to 100,000-fold) of empty subviral particles (SVP) composed solely of HBV envelope proteins (HBsAg) in the form of relatively smaller spheres and filaments of variable length. Subviral particles were shown to strongly enhance intracellular viral replication and gene expression of HBV (Bruns M. et al. 1998 J Virol 72(2): 1462-1468). This is also important in the context of infectivity of sera containing HBV, since the infectivity depends not only on the number of viruses but also on the number of SVP's (Bruns M. et al. 1998 J Virol 72(2): 1462-1468). Moreover, an excess of subviral particles can serve as a decoy by absorbing neutralizing antibodies and therefore delay the clearance of infection. Typically, achievement of hepatitis B surface antigen (HBsAg) loss is thus considered to be an ideal endpoint of treatment and the closest outcome to cure chronic hepatitis B (CHB).

Accordingly, the antibody according to the present invention, or an antigen binding fragment thereof, which preferably promotes clearance of HBsAg, in particular clearance of subviral particles of hepatitis B virus, and HBV enables improved treatment of hepatitis B, in particular in the context of chronic hepatitis B. Thereby, the antibody according to the present invention, or an antigen binding fragment thereof, can exert its neutralization properties even more potent since less of the antibody is absorbed by SVP's acting as a decoy. In addition, the antibody according to the present invention, or an antigen binding fragment thereof, which preferably promotes clearance of subviral particles of hepatitis B virus, decreases infectivity of sera containing HBV.

Preferably, the antibody according to the present invention, or an antigen binding fragment thereof, comprises an Fc moiety. More preferably, the Fc moiety is derived from human origin, e.g. from human IgG1, IgG2, IgG3, and/or IgG4, whereby human IgG1 is particularly preferred.

As used herein, the term "Fc moiety" refers to a sequence derived from the portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. A complete Fc moiety comprises at least a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Each of the amino acid positions within an Fc moiety have been numbered according to the art-recognized EU numbering system of Kabat, see e.g., by Kabat et al., in "Sequences of Proteins of Immunological Interest", U.S. Dept. Health and Human Services, 1983 and 1987.

Preferably, in the context of the present invention an Fc moiety comprises at least one of: a hinge (e.g., upper, middle, and/or lower hinge region) domain, a CH2 domain, a CH3 domain, or a variant, portion, or fragment thereof. In preferred embodiments, an Fc moiety comprises at least a hinge domain, a CH2 domain or a CH3 domain. More preferably, the Fc moiety is a complete Fc moiety.

The Fc moiety may also comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a hinge domain (or portion thereof), (v) a CH2 domain (or portion thereof), or (vi) a CH3 domain or portion thereof.

It will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. Such functions include Fc receptor (FcR) binding, antibody half-life modulation, ADCC function, protein A binding, protein G binding, and complement binding. The portions of naturally occurring Fc moieties, which are responsible and/or essential for such functions are well known by those skilled in the art.

For example, to activate the complement cascade C1q binds to at least two molecules of IgG1 or one molecule of IgM, attached to the antigenic target (Ward, E. S., and Ghetie, V., Ther. Immunol. 2 (1995) 77-94). Burton, D. R., described (Mol. Immunol. 22 (1985) 161-206) that the heavy chain region comprising amino acid residues 318 to 337 is involved in complement fixation. Duncan, A. R., and Winter, G. (Nature 332 (1988) 738-740), using site directed mutagenesis, reported that Glu318, Lys320 and Lys322 form the binding site to C1q. The role of Glus18, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on hematopoietic cells. Fc receptors belong to the immunoglobulin superfamily, and were shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., J. Leukoc. Biol. 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., Annu. Rev. Immunol. 9 (1991) 457-492; Capel, P. J., et al., Immunomethods 4 (1994) 25-34; de Haas, M., et al., J Lab. Clin. Med. 126 (1995) 330-341; and Gessner, J. E., et al., Ann. Hematol. 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Therefore, Fc moieties providing cross-linking of receptors (FcγR) are preferred. In humans, three classes of FcγR have been characterized, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is known to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homolougous; and (iii) FcγRIII (CD16), which binds IgG with medium to low affinity and exists as two types: FcγRIIIA found on NK cells, macrophages, eosinophils and some monocytes and T cells and mediating ADCC and FcγRIIIB, which is highly expressed on neutrophils. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. Importantly, 75% of all FcγRIIB is found in the liver (Ganesan, L. P. et al., 2012: FcγRIIb on liver sinusoidal endothelium clears small immune complexes. Journal of Immunology 189: 4981-4988). FcγRIIB is abundantly expressed on Liver Sinusoidal Endothelium, called LSEC, and in Kupffer cells in the liver and LSEC are the major site of small immune complexes clearance (Ganesan, L. P. et al., 2012: FcγRIIb on liver sinusoidal endothelium clears small immune complexes. Journal of Immunology 189: 4981-4988).

Accordingly, in the present invention such antibodies, and antigen binding fragments thereof, are preferred, which are able to bind to FcγRIIb, for example antibodies comprising an Fc moiety for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933. Thereby, the clearance of immune complexes can be enhanced (Chu, S., et al., 2014: Accelerated Clearance of IgE In Chimpanzees Is Mediated By Xmab7195, An Fc-Engineered Antibody With Enhanced Affinity For Inhibitory Receptor FcγRIIb. Am J Respir Crit, American Thoracic Society International Conference Abstracts). Accordingly, in the context of the present invention such antibodies, or antigen binding fragments thereof, are preferred, which comprise an engineered Fc moiety with the mutations S267E and L328F, in particular as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933.

On B-cells it seems to function to suppress further immunoglobulin production and isotype switching to say for example the IgE class. On macrophages, FcγRIIB acts to inhibit phagocytosis as mediated through FcγRIIA. On eosinophils and mast cells the b form may help to suppress activation of these cells through IgE binding to its separate receptor.

Regarding FcγRI binding, modification in native IgG of at least one of E233-G236, P238, D265, N297, A327 and P329 reduces binding to FcγRI. IgG2 residues at positions 233-236, substituted into IgG1 and IgG4, reduces binding to FcγRI by 103-fold and eliminated the human monocyte response to antibody-sensitized red blood cells (Armour, K. L., et al. Eur. J. Immunol. 29 (1999) 2613-2624). Regarding FcγRII binding, reduced binding for FcγRIIA is found e.g. for IgG mutation of at least one of E233-G236, P238, D265, N297, A327, P329, D270, Q295, A327, R292 and K414. Regarding FcγRIII binding, reduced binding to FcγRIIIA is found e.g. for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above mentioned mutation sites and methods for measuring binding to FcγRI and FcγRIIA are described in Shields, R. L., et al., *J. Biol. Chem.* 276 (2001) 6591-6604.

Regarding binding to the crucial FcγRII, two regions of native IgG Fc appear to be critical for interactions of FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRI appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

For example, the Fc moiety may comprise or consist of at least the portion of an Fc moiety that is known in the art to be required for FcRn binding or extended half-life. Alternatively or additionally, the Fc moiety of the antibody of the invention comprises at least the portion of known in the art to be required for Protein A binding and/or the Fc moiety of the antibody of the invention comprises at least the portion of an Fc molecule known in the art to be required for protein G binding. Preferably, the retained function is the clearance of HBsAg and HBV, which is assumed to be mediated by FcγR binding. Accordingly, a preferred Fc moiety comprises at least the portion known in the art to be required for FcγR binding. As outlined above, a preferred Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

Preferably, the antibody, or antigen binding fragment thereof, according to the present invention comprises an Fc region. As used herein, the term "Fc region" refers to the portion of an immunoglobulin formed by two or more Fc moieties of antibody heavy chains. For example, the Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2. Preferably, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties.

The Fc moieties of the Fc region may be of the same or different class and/or subclass. For example, the Fc moieties may be derived from an immunoglobulin (e.g., a human immunoglobulin) of an IgG1, IgG2, IgG3 or IgG4 subclass. Preferably, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. Additionally or alternatively, the chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or moiety may (additionally or alternatively) for example comprise a chimeric hinge region.

For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser22SPro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKY-GPPCPPCPAPPVAGP (SEQ ID NO: 91)). Further chimeric hinges, which may be used in the Fc moiety of the antibody according to the present invention are described in US 2005/0163783 A1.

In the present invention it is preferred that the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Preferably, the antibody according to the present invention comprises, in particular in addition to an Fc moiety as described above, other parts derived from a constant region, in particular from a constant region of IgG, preferably from a constant region of IgG1, more preferably from a constant region of human IgG1. More preferably, the antibody according to the present invention comprises, in particular in addition to an Fc moiety as described above, all other parts of the constant regions, in particular all other parts of the constant regions of IgG, preferably all other parts of the constant regions of IgG1, more preferably all other parts of the constant regions of human IgG1.

As outlined above, a particularly preferred antibody according to the present invention comprises a (complete) Fc region derived from human IgG1. More preferably, the antibody according to the present invention comprises, in particular in addition to a (complete) Fc region derived from human IgG1 also all other parts of the constant regions of IgG, preferably all other parts of the constant regions of IgG1, more preferably all other parts of the constant regions of human IgG1.

It is also preferred that the antibody according to the present invention, or an antigen binding fragment thereof, binds to 1, 2, 3, 4, 5, 6, 7, 8, 9 or 10 of the HBsAg genotypes A, B, C, D, E, F, G, H, I, and J. Examples for the different genotypes of HBsAg include the following: GenBank accession number J02203 (HBV-D, ayw3), GenBank accession number FJ899792.1 (HBV-D, adw2), GenBank accession number AM282986 (HBV-A), GenBank accession number D23678 (HBV-B1 Japan), GenBank accession number AB117758 (HBV-C1 Cambodia), GenBank accession number AB205192 (HBV-E Ghana), GenBank accession number X69798 (HBV-F4 Brazil), GenBank accession number AF160501 (HBV-G USA), GenBank accession number AY090454 (HBV-H Nicaragua), GenBank accession number AF241409 (HBV-I Vietnam) and GenBank accession number AB486012 (HBV-J Borneo). The amino acid sequences of the antigenic loop region of the S domain of HBsAg of the different genotypes is shown in Table 1 (SEQ ID NO's: 5-15).

More preferably, the antibody according to the present invention, or an antigen binding fragment thereof, binds to at least 6, even more preferably to at least 8, and particularly preferably to all 10 of the HBsAg genotypes A, B, C, D, E, F, G, H, I, and J. HBV is differentiated into many genotypes, according to genome sequence. To date, eight well-known genotypes (A-H) of the HBV genome have been defined. Moreover, two new genotypes, I and J, have also been identified (Sunbul M., 2014, World J Gastroenterol 20(18): 5427-5434). The genotype is known to affect the progression of the disease and differences between genotypes in response to antiviral treatment have been determined. For example, genotype A has a tendency for chronicity, whereas viral mutations are frequently encountered in genotype C. Both chronicity and mutation frequency are common in genotype D. Moreover, the genotypes of HBV are differentially distributed over the world (Sunbul M., 2014, *World J Gastroenterol* 20(18): 5427-5434). By providing an antibody according to the present invention, or an antigen binding fragment thereof, which preferably binds to at least 6, preferably to at least 8, more preferably to all 10 of the HBsAg genotypes A, B, C, D, E, F, G, H, I, and J, an antibody is provided, which binds very broadly to the different genotypes.

Preferably, the antibody according to the present invention, or an antigen binding fragment thereof, binds to 1, 2, 3, 4, 5, 6, 7, 8, 9, 10, 11, 12, 13, 14, 15, 16, 17 or 18 of the HBsAg mutants having mutations in the antigenic loop region: HBsAg Y100C/P120T, HBsAg P120T, HBsAg P120T/S143L, HBsAg C121S, HBsAg R122D, HBsAg R122I, HBsAg T123N, HBsAg Q129H, HBsAg Q129L, HBsAg M133H, HBsAg M133L, HBsAg M133T, HBsAg K141E, HBsAg P142S, HBsAg S143K, HBsAg D144A, HBsAg G145R and HBsAg N146A. Those mutants are naturally occurring mutants based on the S domain of HBsAg Genotype D, Genbank accession no. FJ899792 (SEQ ID NO: 4), whereby the mutated amino acid residue(s) are indicated in the name.

```
SEQ ID NO: 4:
MENVTSGFLGPLLVLQAGFFLLTRILTIPQSLDSWWTSLNFLGGTTVCLGQ

NSQSPTSNHSPTSCPPTCPGYRWMCLRRFIIFLFILLLCLIFLLVLLDYQG

MLPVCPLIPGSSTTGTGPCRTCTTPAQGTSMYPSCCCTKPSDGNCTCIPIP

SSWAFGKFLWEWASARFSWLSLLVPFVQWFVGLSPTVWLSVIWMMWYWGPS

LYSTLSPFLPLLPIFFCLWVYI
(the antigenic loop region, i.e. amino acids 101-
172, is shown underlined).
```

The amino acid sequences of the antigenic loop region of the S domain of HBsAg of the different mutants is shown in Table 1 (SEQ ID NO's: 16-33).

More preferably, the antibody according to the present invention, or an antigen binding fragment thereof, binds to at least 12, even more preferably to at least 15, and particularly preferably to all 18 of the infectious HBsAg mutants having mutations in the antigenic loop region: HBsAg Y100C/P120T, HBsAg P120T, HBsAg P120T/S143L, HBsAg C121S, HBsAg R122D, HBsAg R122I, HBsAg T123N, HBsAg Q129H, HBsAg Q129L, HBsAg M133H, HBsAg M133L, HBsAg M133T, HBsAg K141E, HBsAg P142S, HBsAg S143K, HBsAg D144A, HBsAg G145R and HBsAg N146A.

Preferably, the antibody according to the present invention, or an antigen binding fragment thereof, binds to an epitope comprising at least one, preferably at least two, more preferably at least three amino acids, even more preferably at least four amino acids of the antigenic loop region of HBsAg, wherein the at least two, preferably the at least three, more preferably the at least four amino acids are selected from amino acids 115-133 of the S domain of HBsAg, preferably from amino acids 120-133 of the S domain of HBsAg, more preferably from amino acids 120-130 of the S domain of HBsAg. Of note, the position of the amino acids (e.g. 115-133, 120-133, 120-130) refers to the S domain of HBsAg as described above, which is present in all three HBV envelope proteins S-HBsAg, M-HBsAg, and L-HBsAg, whereby S-HBsAg typically corresponds to the S domain of HBsAg.

In particular, the antibody according to the present invention, or an antigen binding fragment thereof, binds to an epitope in the antigenic loop region of HBsAg, whereby the epitope is typically formed by one or more amino acids located at positions selected from amino acid positions 115-133, preferably selected from amino acid positions 120-133, more preferably selected from amino acid positions 120-130 of the S domain of HBsAg.

The term "formed by" as used herein in the context of an epitope means, that the epitope to which the antibody of the invention, or an antigen binding fragment thereof, binds to may be linear (continuous) or conformational (discontinuous). A linear or a sequential epitope is an epitope that is recognized by antibodies by its linear sequence of amino acids, or primary structure. In contrast, a conformational epitope has a specific three-dimensional shape and protein structure. Accordingly, if the epitope is a linear epitope and comprises more than one amino acid located at positions selected from amino acid positions 115-133, preferably selected from amino acid positions 120-133 of the S domain of HBsAg, the amino acids comprised by the epitope are typically located in adjacent positions of the primary structure (i.e. consecutive amino acids in the amino acid sequence). In the case of a conformational epitope (3D structure), in contrast, the amino acid sequence typically forms a 3D structure as epitope and, thus, the amino acids forming the epitope (or the amino acids "comprised by" the epitope) may be or may be not located in adjacent positions of the primary structure (i.e. maybe or may be not consecutive amino acids in the amino acid sequence).

Preferably, the epitope to which the antibody of the invention, or an antigen binding fragment thereof, binds to is only formed by amino acid(s) selected from amino acid positions 115-133, preferably selected from amino acid positions 120-133, more preferably selected from amino acid positions 120-130 of the S domain of HBsAg. In other words, it is preferred that no (further) amino acids—which are located outside the positions 115-133, preferably positions 120-133, more preferably positions 120-130—are required to form the epitope to which the antibody of the invention, or an antigen binding fragment thereof, binds to.

Preferably, the epitope in the antigenic loop region of HBsAg to which the antibody of the invention, or an antigen binding fragment thereof, bind are formed by two or more amino acids located at positions selected from amino acid positions 115-133, preferably selected from amino acid positions 120-133, more preferably selected from amino acid positions 120-130 of the S domain of HBsAg. More preferably, the epitope in the antigenic loop region of HBsAg to which the antibody of the invention, or an antigen binding fragment thereof, bind are formed by three or more amino acids located at positions selected from amino acid positions 115-133, preferably selected from amino acid positions 120-133, more preferably selected from amino acid positions 120-130 of the S domain of HBsAg. Even more preferably, the epitope in the antigenic loop region of HBsAg to which the antibody of the invention, or an antigen binding fragment thereof, bind are formed by four or more amino acids located at positions selected from amino acid positions 115-133, preferably selected from amino acid positions 120-133, more preferably selected from amino acid positions 120-130 of the S domain of HBsAg. In other words, it is preferred that, the antibody according to the present invention, or an antigen binding fragment thereof, binds to at least one, preferably at least two, more preferably at least three, even more preferably to at least four amino acids of the antigenic loop region of HBsAg selected from amino acid 115-amino acid 133 of the S domain of HBsAg, preferably from amino acid 120-amino acid 133 of the S domain of HBsAg, more preferably selected from amino acids 120-130 of the S domain of HBsAg.

More preferably, the antibody according to the present invention, or the antigen binding fragment thereof, binds to an epitope comprising at least two, preferably at least three, more preferably at least four amino acids of the antigenic loop region of HBsAg, wherein the at least two, preferably the at least three, more preferably the at least four amino acids are selected from amino acid 120-amino acid 133, preferably from amino acids 120-130 of The S domain of HBsAg and wherein the at least two, preferably the at least three, more preferably the at least four amino acids are located in adjacent positions (i.e. are consecutive amino acids in the amino acid sequence/primary structure).

The epitope to which the antibody according to the present invention, or an antigen binding fragment thereof, binds to, is preferably a conformational epitope. Accordingly, it is preferred that the antibody according to the present invention, or an antigen binding fragment thereof, binds to an epitope comprising at least two, preferably at least three, more preferably at least four amino acids of the antigenic loop region of HBsAg, wherein the at least two, preferably the at least three, more preferably the at least four amino acids are selected from amino acids 120-133, preferably from amino acids 120-130, of the S domain of HBsAg and wherein at least two, preferably at least three, of the at least two, preferably the at least three, more preferably the at least four amino acids are not located in adjacent positions (of the primary structure).

In other words, (i) either none of the amino acids to which the antibody binds to (i.e. the amino acids forming the epitope) are located in adjacent positions of the primary structure or (ii) some, for example two or three, of the amino acids to which the antibody binds to (i.e. the amino acids forming the epitope) are located in adjacent positions (of the primary structure) whereas other amino acids to which the antibody binds to (i.e. the amino acids forming the epitope) are not located in adjacent positions (of the primary structure).

Amino acids to which the antibody binds to (i.e. the amino acids forming the epitope), which are not located in adjacent positions of the primary structure, are typically spaced apart by one or more amino acids, to which the antibody does not bind to. Preferably, at least one, more preferably at least two, even more preferably at least three, most preferably at least four, particularly preferably at least five amino acids may be located between the at least two, preferably at least three, amino acids, which are comprised by the epitope and which are not located in adjacent positions.

Preferably, the antibody according to the present invention, or an antigen binding fragment thereof, binds to an epitope comprising at least amino acids P120, C121, R122 and C124 of the S domain of HBsAg. More preferably, the antibody or the antigen binding fragment binds to an epitope comprising an amino acid sequence according to SEQ ID NO: 88:

PCRXC wherein X is any amino acid or no amino acid; preferably X is any amino acid; more preferably X is T, Y, R, S, or F; even more preferably X is T, Y or R; most preferably X is T or R.

Even more preferably the antibody or the antigen binding fragment binds to an epitope comprising an amino acid sequence according to SEQ ID NO: 80:

TGPCRTC or to an amino acid sequence sharing at least 80%, preferably at least 90%, more preferably at least 95% sequence identity with SEQ ID NO: 80.

Most preferably, the antibody or the antigen binding fragment binds to an epitope comprising an amino acid sequence according to SEQ ID NO: 85:

STTSTGPCRTC or to an amino acid sequence sharing at least 80%, preferably at least 90%, more preferably at least 95% sequence identity with SEQ ID NO: 85.

It is also preferred that the antibody or the antigen binding fragment binds to an epitope comprising an amino acid sequence comprising at least amino acids 145-151 of the S domain of HBsAg:

GNCTCIP (SEQ ID NO: 81).

More preferably, the antibody or the antigen binding fragment binds to an epitope comprising an amino acid sequence according to SEQ ID NO: 80 and an amino acid sequence according to SEQ ID NO: 81.

More preferably, the antibody or the antigen binding fragment binds to an epitope comprising an amino acid sequence according to SEQ ID NO: 85 and/or an amino acid sequence according to SEQ ID NO: 87.

As described above, the epitope to which the antibodies of the invention binds to may be linear (continuous) or conformational (discontinuous). Preferably, the antibody and antibody fragments of the invention binds to a conformational epitope, more preferably the conformational epitope is present only under non-reducing conditions.

However, it is also preferred that the antibody according to the present invention, or an antibody fragment thereof, binds to a linear epitope, more preferably the linear epitope is present under both, non-reducing conditions and reducing conditions.

Preferably, the antibody according to the present invention, or an antigen binding fragment thereof, binds to an epitope in the antigenic loop of HBsAg formed by an amino acid sequence according to SEQ ID NO: 1:

```
                                              (SEQ ID NO: 1)
X1 X2 X3 TC X4 X5 X6A X7G
wherein X1, X2, X3, X4, X5, X6 and X7 may be any
amino acid.
```

Preferably, $X_1$, $X_2$, $X_3$, $X_4$, $X_5$, $X_6$ and $X_7$ are amino acids, which are conservatively substituted in comparison to amino acids 120-130 of SEQ ID NO: 3. It is also preferred that $X_1$, $X_2$, $X_3$, $X_4$, $X_5$, $X_6$ and $X_7$ are amino acids, which are conservatively substituted in comparison to amino acids 20-30 of any of SEQ ID NO's 5-33 (cf. Table 1; referring to the antigenic loop region sequences, i.e. aa 101-172 of the S domain of different variants of HBsAG).

Preferably, in SEQ ID NO: 1 $X_1$ is a small amino acid. A "small" amino acid, as used herein, refers to any amino acid selected from the group consisting of alanine, aspartic acid, asparagine, cysteine, glycine, proline, serine, threonine and valine. More preferably, $X_1$ is proline, serine or threonine.

Preferably, in SEQ ID NO: 1 $X_2$ is a small amino acid. More preferably, $X_2$ is cystein or threonine.

Preferably, in SEQ ID NO: 1 $X_3$ is a charged amino acid or an aliphatic amino acid. A "charged" amino acid, as used herein, refers to any amino acid selected from the group consisting of arginine, lysine, aspartic acid, glutamic acid and histidine. A "aliphatic" amino acid, as used herein, refers to any amino acid selected from the group consisting of alanine, glycine, isoleucine, leucine, and valine. More preferably, $X_3$ is arginine, lysine, aspartic acid or isoleucine.

Preferably, in SEQ ID NO: 1 $X_4$ is a small amino acid and/or a hydrophobic amino acid. A "hydrophobic" amino acid, as used herein, refers to any amino acid selected from the group consisting of alanine, isoleucine, leucine, phenylalanine, valine, tryptophan, tyrosin, methionine, proline and glycine. More preferably, $X_4$ is methionine or threonine.

Preferably, in SEQ ID NO: 1 $X_5$ is a small amino acid and/or a hydrophobic amino acid. More preferably, $X_5$ is threonine, alanine or isoleucine.

Preferably, in SEQ ID NO: 1 $X_6$ is a small amino acid and/or a hydrophobic amino acid. More preferably, $X_e$ is threonine, proline or leucine.

Preferably, in SEQ ID NO: 1 $X_7$ is a polar amino acid or an aliphatic amino acid. A "polar" amino acid, as used herein, refers to any amino acid selected from the group consisting of aspartic acid, asparagine, arginine, glutamic acid, histidine, lysine, glutamine, tryptophan, tyrosine, serine, and threonine. More preferably, $X_7$ is glutamine, histidine or leucine.

Accordingly, it is more preferred that the antibody according to the present invention, or an antigen binding fragment thereof, binds to an epitope in the antigenic loop of HBsAg formed by an amino acid sequence according to SEQ ID NO: 2:

```
                                              (SEQ ID NO: 2)
X1 X2 X3 TC X4 X5 X6A X7G
wherein X1 is P, T or S,
X2 is C or S,
X3 is R, K, D or I,
X4 is M or T,
X5 is T, A or I,
X6 is T, P or L, and
X7 is Q, H or L.
```

With regard to the preferred epitopes formed by the amino acid sequences according to SEQ ID NO: 1 or 2, it is noted that the term "formed by" as used herein is in particular not intended to imply that the antibody necessarily binds to each and every amino acid of SEQ ID NO: 1 or 2. In particular in the case of the preferred conformational epitope, the antibody may bind only to some of the amino acids of SEQ ID NO: 1 or 2, whereby other amino acid residues may merely act as "spacers", thereby providing the 3D structure of the epitope.

Preferably, the antibody according to the present invention, or an antigen binding fragment thereof, binds to an epitope in the antigenic loop of HBsAg formed by one or more, preferably by two or more, more preferably by three or more and even more preferably by four or more amino acids of an amino acid sequence selected from SEQ ID NO's 5-33 shown below in Table 1.

More preferably, the antibody according to the present invention, or an antigen binding fragment thereof, binds to an antigenic loop region of HBsAg having an amino acid sequence according to any of SEQ ID NO's 5-33 shown below in Table 1 or to a sequence variant thereof. Even more preferably, the antibody according to the present invention, or an antigen binding fragment thereof, binds to all of the antigenic loop variants of HBsAg having an amino acid sequence according to any of SEQ ID NO's 5-33 shown below in Table 1. In other words, it is particularly preferred if the antibody according to the present invention, or an antigen binding fragment thereof, is able to bind to all of the different antigenic loop regions of HBsAg having an amino acid sequence according to any of SEQ ID NO's 5-33.

TABLE 1

Exemplary amino acid sequences of the antigenic loop region of the S domain of HBsAg (residues 101-172 of the S domain of HBsAg-except for SEQ ID NO: 16 which refers to residues 100-172 of the S domain of HBsAg in order to include the relevant mutation) of the different genotypes and mutants as used herein.

| Name | SEQ ID NO. | Amino acid sequence |
|---|---|---|
| J02203 (D, ayw3) | 5 | QGMLPVCPLIPGSSTTSTGPCRTCMTTAQGTSMYPSCCC TKPSDGNCTCIPIPSSWAFGKFLWEWASARFSW |
| FJ899792 (D, adw2) | 6 | QGMLPVCPLIPGSSTTGTGPCRTCTTPAQGTSM YPSCCCTKPSDGNCTCIPIPSSWAFGKFLWEWAS ARFSW |
| AM282986 (A) | 7 | QGMLPVCPLIPGTTTTSTGPCKTCTTPAQGNSMFPSCCC TKPSDGNCTCIPIPSSWAFAKYLWEWASVRFSW |
| D23678 (B1) | 8 | QGMLPVCPLIPGSSTTSTGPCKTCTTPAQGTSMFPSCCCT KPTDGNCTCIPIPSSWAFAKYLWEWASVRFSW |
| AB117758 (C1) | 9 | QGMLPVCPLLPGTSTTSTGPCKTCTIPAQGTSMFPSCCCT KPSDGNCTCIPIPSSWAFARFLWEWASVRFSW |
| AB205192 (E) | 10 | QGMLPVCPLIPGSSTTSTGPCRTCTTLAQGTSMFPSCCCS KPSDGNCTCIPIPSSWAFGKFLWEWASARFSW |
| X69798 (F4) | 11 | QGMLPVCPLLPGSTTTSTGPCKTCTTLAQGTSMFPSCCC SKPSDGNCTCIPIPSSWALGKYLWEWASARFSW |
| AF160501 (G) | 12 | QGMLPVCPLIPGSSTTSTGPCKTCTTPAQGNSMYPSCCCT KPSDGNCTCIPIPSSWAFAKYLWEWASVRFSW |
| AY090454 (H) | 13 | QGMLPVCPLLPGSTTTSTGPCKTCTTLAQGTSMFPSCCC TKPSDGNCTCIPIPSSWAFGKYLWEWASARFSW |
| AF241409 (I) | 14 | QGMLPVCPLIPGSSTTSTGPCKTCTTPAQGNSMYPSCCCT KPSDGNCTCIPIPSSWAFAKYLWEWASVRFSW |
| AB486012 (J) | 15 | QGMLPVCPLLPGSTTTSTGPCRTCTITAQGTSMFPSCCC TKPSDGNCTCIPIPSSWAFAKFLWEWASVRFSW |
| HBsAg Y100C/P120T | 16 | CQGMLPVCPLIPGSSTTGTGTCRTCTTPAQGTSMYPSCC CTKPSDGNCTCIPIPSSWAFGKFLWEWASARFSW |
| HBsAg P120T | 17 | QGMLPVCPLIPGSSTTGTGTCRTCTTPAQGTSMYPSCCC TKPSDGNCTCIPIPSSWAFGKFLWEWASARFSW |
| HBsAg P120T/S143L | 18 | QGMLPVCPLIPGSSTTGTGTCRTCTTPAQGTSMYPSCCC TKPLDGNCTCIPIPSSWAFGKFLWEWASARFSW |
| HBsAg C121S | 19 | QGMLPVCPLIPGSSTTGTGPSRTCTTPAQGTSMYPSCCC TKPSDGNCTCIPIPSSWAFGKFLWEWASARFSW |
| HBsAg R122D | 20 | QGMLPVCPLIPGSSTTGTGPCDTCTTPAQGTSMYPSCCC TKPSDGNCTCIPIPSSWAFGKFLWEWASARFSW |
| HBsAg R122I | 21 | QGMLPVCPLIPGSSTTGTGPCITCTTPAQGTSMYPSCCCT KPSDGNCTCIPIPSSWAFGKFLWEWASARFSW |
| HBsAg T123N | 22 | QGMLPVCPLIPGSSTTGTGPCRNCTTPAQGTSMYPSCCC TKPSDGNCTCIPIPSSWAFGKFLWEWASARFSW |
| HBsAg Q129H | 23 | QGMLPVCPLIPGSSTTGTGPCRTCTTPAHGTSMYPSCCC TKPSDGNCTCIPIPSSWAFGKFLWEWASARFSW |

TABLE 1-continued

Exemplary amino acid sequences of the antigenic loop region of the S domain of HBsAg (residues 101-172 of the S domain of HBsAg-except for SEQ ID NO: 16 which refers to residues 100-172 of the S domain of HBsAg in order to include the relevant mutation) of the different genotypes and mutants as used herein.

| Name | SEQ ID NO. | Amino acid sequence |
|---|---|---|
| HBsAg Q129L | 24 | QGMLPVCPLIPGSSTTGTGPCRTCTTPALGTSMYPSCCC TKPSDGNCTCIPIPSSWAFGKFLWEWASARFSW |
| HBsAg M133H | 25 | QGMLPVCPLIPGSSTTGTGPCRTCTTPAQGTSHYPSCCC TKPSDGNCTCIPIPSSWAFGKFLWEWASARFSW |
| HBsAg M133L | 26 | QGMLPVCPLIPGSSTTGTGPCRTCTTPAQGTSLYPSCCCT KPSDGNCTCIPIPSSWAFGKFLWEWASARFSW |
| HBsAg M133T | 27 | QGMLPVCPLIPGSSTTGTGPCRTCTTPAQGTSYPSCCCT KPSDGNCTCIPIPSSWAFGKFLWEWASARFSW |
| HBsAg K141E | 28 | QGMLPVCPLIPGSSTTGTGPCRTCTTPAQGTSMYPSCCC TEPSDGNCTCIPIPSSWAFGKFLWEWASARFSW |
| HBsAg P142S | 29 | QGMLPVCPLIPGSSTTGTGPCRTCTTPAQGTSMYPSCCC TKSSDGNCTCIPIPSSWAFGKFLWEWASARFSW |
| HBsAg S143K | 30 | QGMLPVCPLIPGSSTTGTGPCRTCTTPAQGTSMYPSCCC TKPKDGNCTCIPIPSSWAFGKFLWEWASARFSW |
| HBsAg D144A | 31 | QGMLPVCPLIPGSSTTGTGPCRTCTTPAQGTSMYPSCCC TKPSAGNCTCIPIPSSWAFGKFLWEWASARFSW |
| HBsAg G145R | 32 | QGMLPVCPLIPGSSTTGTGPCRTCTTPAQGTSMYPSCCC TKPSDRNCTCIPIPSSWAFGKFLWEWASARFSW |
| HBsAg N146A | 33 | QGMLPVCPLIPGSSTTGTGPCRTCTTPAQGTSMYPSCCC TKPSDGACTCIPIPSSWAFGKFLWEWASARFSW |

In general, the antibody according to the present invention, or the antigen binding fragment thereof, preferably comprises (at least) three complementarity determining regions (CDRs) on a heavy chain and (at least) three CDRs on a light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR's.

The sequences of the heavy chains and light chains of an exemplary antibody of the invention, comprising three different CDRs on the heavy chain and three different CDRs on the light chain were determined. The position of the CDR amino acids are defined according to the IMGT numbering system (IMGT: http://www.imgt.org/; cf. Lefranc, M.-P. et al. (2009) Nucleic Acids Res. 37, D1006-D1012).

Table 2 shows the amino acid sequences of the CDR's and the heavy chain variable region (VH) and the light chain variable region (VL) of an exemplary antibody according to the present invention ("HBC34"):

| HBC34 | SEQ ID NO. | Amino acid sequence |
|---|---|---|
| CDRH1 | 34 | GRIFRSFY |
| CDRH2 | 35 | NQDGSEK |
| CDRH2 long | 66 | INQDGSEK |
| CDRH3 | 36 | AAWSGNSGGMDV |
| CDRL1 | 37 | KLGNKN |
| CDRL2 | 38 | EVK |
| CDRL2 long | 39 | VIYEVKYRP |
| CDRL3 | 40 | QTWDSTTVV |
| VH | 41 | ELQLVESGGGWVQPGGSQRLSCAASGRIFRSFYMSWVRQAP GKGLEWVATINQDGSEKLYVDSVKGRFTISRDNAKNSLFLQ MNNLRVEDTAVYYCAAWSGNSGGMDVWGQGTTVSVSS |

| HBC34 | SEQ ID NO. | Amino acid sequence |
|---|---|---|
| VL | 42 | SYELTQPPSVSVSPGQTVSIPCSGDKLGNKNVCWFQHKPGQSPVLVIYEVKYRPSGIPERFSGSNSGNTATLTISGTQAMDEAAYFCQTWDSTTVVFGGGTRLTVL |

It is thus preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 2.

Table 3 shows the amino acid sequences of the CDR's and the heavy chain variable region (VH) and the light chain variable region (VL) of a further exemplary antibody according to the present invention ("HBC34v7"):

| HBC34v7 | SEQ ID NO. | Amino acid sequence |
|---|---|---|
| CDRH1 | 34 | GRIFRSFY |
| CDRH2 | 35 | NQDGSEK |
| CDRH2 long | 66 | INQDGSEK |
| CDRH3 | 36 | AAWSGNSGGMDV |
| CDRL1 | 37 | KLGNKN |
| CDRL2 | 38 | EVK |
| CDRL2 long | 39 | VIYEVKYRP |
| CDRL3 | 58 | QTFDSTTVV |
| VH | 41 | ELQLVESGGGWVQPGGSQRLSCAASGRIFRSFYMSWVRQAPGKGLEWVATINQDGSEKLYVDSVKGRFTISRDNAKNSLFLQMNNLRVEDTAVYYCAAWSGNSGGMDVWGQGTTVSVSS |
| VL | 59 | SYELTQPPSVSVSPGQTVSIPCSGDKLGNKNVCWFQHKPGQSPVLVIYEVKYRPSGIPERFSGSNSGNTATLTISGTQAMDEAAYFCQTFDSTTVVFGGGTRLTVL |

It is thus also preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 3.

Table 4 shows the amino acid sequences of the CDR's and the heavy chain variable region (VH) and the light chain variable region (VL) of a further exemplary antibody according to the present invention ("HBC34v23"):

| HBC34v23 | SEQ ID NO. | Amino acid sequence |
|---|---|---|
| CDRH1 | 34 | GRIFRSFY |
| CDRH2 | 35 | NQDGSEK |
| CDRH2 long | 66 | INQDGSEK |
| CDRH3 | 36 | AAWSGNSGGMDV |
| CDRL1 | 37 | KLGNKN |
| CDRL2 | 38 | EVK |
| CDRL2 long | 39 | VIYEVKYRP |
| CDRL3 | 58 | QTFDSTTVV |
| VH | 41 | ELQLVESGGGWVQPGGSQRLSCAASGRIFRSFYMSWVRQAPGKGLEWVATINQDGSEKLYVDSVKGRFTISRDNAKNSLFLQMNNLRVEDTAVYYCAAWSGNSGGMDVWGQGTTVSVSS |
| VL | 65 | SYELTQPPSVSVSPGQTASITCSGDKLGNKNACWYQQKPGQSPVLVIYEVKYRPSGIPERFSGSNSGNTATLTISGTQAMDEADYYCQTFDSTTVVFGGGTKLTVL |

It is thus also preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 4.

Table 5 shows the amino acid sequences of the CDR's and the heavy chain variable region (VH) and the light chain variable region (VL) of a further exemplary antibody according to the present invention ("HBC34v31"):

| HBC34v31 | SEQ ID NO. | Amino acid sequence |
|---|---|---|
| CDRH1 | 34 | GRIFRSFY |
| CDRH2 | 35 | NQDGSEK |
| CDRH2 long | 66 | INQDGSEK |
| CDRH3 | 36 | AAWSGNSGGMDV |
| CDRL1 | 37 | KLGNKN |
| CDRL2 | 38 | EVK |
| CDRL2 long | 39 | VIYEVKYRP |
| CDRL3 | 40 | QTWDSTTVV |
| VH | 67 | EVQLVESGGGLVQPGGSLRLSCAASGRIFRSFYMSWVRQAPGKGLEWVANINQDGSEKLYVDSVKGRFTISRDNAKNSLFLQMNNLRVEDTAVYYCAAWSGNSGGMDVWGQGTTVTVSS |
| VL | 42 | SYELTQPPSVSVSPGQTVSIPCSGDKLGNKNVCWFQHKPGQSPVLVIYEVKYRPSGIPERFSGSNSGNTATLTISGTQAMDEAAYFCQTWDSTTVVFGGGTRLTVL |

It is thus preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 5.

Table 6 shows the amino acid sequences of the CDR's and the heavy chain variable region (VH) and the light chain variable region (VL) of a further exemplary antibody according to the present invention ("HBC34v32"):

| HBC34v32 | SEQ ID NO. | Amino acid sequence |
|---|---|---|
| CDRH1 | 34 | GRIFRSFY |
| CDRH2 | 35 | NQDGSEK |
| CDRH2 long | 66 | INQDGSEK |
| CDRH3 | 36 | AAWSGNSGGMDV |
| CDRL1 | 37 | KLGNKN |
| CDRL2 | 38 | EVK |
| CDRL2 long | 39 | VIYEVKYRP |
| CDRL3 | 58 | QTFDSTTVV |
| VH | 67 | EVQLVESGGGLVQPGGSLRLSCAASGRIFRSFYMSWVRQAPGKGLEWVANINQDGSEKLYVDSVKGRFTISRDNAKNSLFLQMNNLRVEDTAVYYCAAWSGNSGGMDVWGQGTTVTVSS |
| VL | 59 | SYELTQPPSVSVSPGQTVSIPCSGDKLGNKNVCWFQHKPGQSPVLVIYEVKYRPSGIPERFSGSNSGNTATLTISGTQAMDEAAYFCQTFDSTTVVFGGGTRLTVL |

It is thus also preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 6.

Table 7 shows the amino acid sequences of the CDR's and the heavy chain variable region (VH) and the light chain variable region (VL) of a further exemplary antibody according to the present invention ("HBC34v33"):

| HBC34v33 | SEQ ID NO. | Amino acid sequence |
|---|---|---|
| CDRH1 | 34 | GRIFRSFY |
| CDRH2 | 35 | NQDGSEK |
| CDRH2 long | 66 | INQDGSEK |
| CDRH3 | 36 | AAWSGNSGGMDV |
| CDRL1 | 37 | KLGNKN |
| CDRL2 | 38 | EVK |
| CDRL2 long | 39 | VIYEVKYRP |
| CDRL3 | 58 | QTFDSTTVV |
| VH | 67 | EVQLVESGGGLVQPGGSLRLSCAASGRIFRSFYMSWVRQAPGKGLEWVANINQDGSEKLYVDSVKGRFTISRDNAKNSLFLQMNNLRVEDTAVYYCAAWSGNSGGMDVWGQGTTVTVSS |
| VL | 65 | SYELTQPPSVSVSPGQTASITCSGDKLGNKNACWYQQKPGQSPVLVIYEVKYRPSGIPERFSGSNSGNTATLTISGTQAMDEADYYCQTFDSTTVVFGGGTKLTVL |

It is thus also preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 7.

Table 8 provides an overview over the VH and VL modifications of the exemplary antibody variants "HBC34v7", "HBC34v23", "HBC34v31", "HBC34v32" and "HBC34v33" of the wild-type (WT) antibody "HBC34" and over the respective SEQ ID NOs of the corresponding CDR and VH/VL amino acid sequences:

| Variant name | VH modification | VL modification | CDR H1 | H2 | H3 | L1 | L2 | L3 | VL | VH |
|---|---|---|---|---|---|---|---|---|---|---|
| HBC34 | WT | WT | 34 | 35/66 | 36 | 37 | 38/39 | 40 | 41 | 42 |
| HBC34-V7 | WT | W107F | 34 | 35/66 | 36 | 37 | 38/39 | 58 | 41 | 59 |
| HBC34-V23 | WT | W07F/ FR1234GL/ CDR2Y66 | 34 | 35/66 | 36 | 37 | 38/39 | 58 | 41 | 65 |
| HBC34-V31 | FR124GL | WT | 34 | 35/66 | 36 | 37 | 38/39 | 40 | 67 | 42 |
| HBC34-V32 | FR124GL | W107F | 34 | 35/66 | 36 | 37 | 38/39 | 58 | 67 | 59 |
| HBC34-V33 | FR124GL | W07F/ FR1234GL/ CDR2Y66 | 34 | 35/66 | 36 | 37 | 38/39 | 58 | 67 | 65 |

Preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 36 or a functional sequence variant thereof as described herein. Accordingly, it is preferred that the at least one heavy chain CDRH3 comprises an amino acid sequence sharing at least 80%, preferably at least 85%, more preferably at least 90%, even more preferably at least 95% and particularly preferably at least 98% or 99% sequence identity with SEQ ID NO: 36. More preferably, the at least one heavy chain CDRH3 comprises an amino acid sequence according to SEQ ID NO: 36.

It is also preferred that the antibody or antigen binding fragment comprises a heavy chain comprising at least one CDRH1, at least one CDRH2 and at least one CDRH3 and a light chain comprising at least one CDRL1, at least one CDRL2 and at least one CDRL3, wherein the at least one light chain CDRL3 comprises an amino acid sequence according to SEQ ID NO: 40 or SEQ ID NO: 58, or a functional sequence variant thereof. Accordingly, it is preferred that the at least one light chain CDRL3 comprises an amino acid sequence sharing at least 80%, preferably at least 85%, more preferably at least 90%, even more preferably at least 95% and particularly preferably at least 98% or 99% sequence identity with SEQ ID NO: 40 or SEQ ID NO: 58. More preferably, the at least one light chain CDRL3 comprises an amino acid sequence according to SEQ ID NO: 40 or SEQ ID NO: 58.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein the at least one heavy chain CDRH1 comprises an amino acid sequence according to SEQ ID NO: 34 or a functional sequence variant thereof, the at least one CDRH2 comprises an amino acid sequence according to SEQ ID NO: 35 or a functional sequence variant thereof and/or the at least one heavy chain CDRH3 comprises an amino acid sequence according to SEQ ID NO: 36 or a functional sequence variant thereof. More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein the at least one heavy chain CDRH1 comprises an amino acid sequence according to SEQ ID NO: 34 or a functional sequence variant thereof, the at least one CDRH2 comprises an amino acid sequence according to SEQ ID NO: 35 or 66 or a functional sequence variant thereof and/or the at least one heavy chain CDRH3 comprises an amino acid sequence according to SEQ ID NO: 36 or a functional sequence variant thereof. Accordingly, it is preferred that the at least one heavy chain CDRH1 comprises an amino acid sequence sharing at least 80%, preferably at least 85%, more preferably at least 90%, even more preferably at least 95% and particularly preferably at least 98% or 99% sequence identity with SEQ ID NO: 34; the at least one heavy chain CDRH2 comprises an amino acid sequence sharing at least 80%, preferably at least 85%, more preferably at least 90%, even more preferably at least 95% and particularly preferably at least 98% or 99% sequence identity with SEQ ID NO: 35 or 66; and/or the at least one heavy chain CDRH3 comprises an amino acid sequence sharing at least 80%, preferably at least 85%, more preferably at least 90%, even more preferably at least 95% and particularly preferably at least 98% or 99% sequence identity with SEQ ID NO: 36. More preferably, the at least one heavy chain CDRH1 comprises an amino acid sequence according to SEQ ID NO: 34; the at least one heavy chain CDRH2 comprises an amino acid sequence according to SEQ ID NO: 35 or 66; and/or the at least one heavy chain CDRH3 comprises an amino acid sequence according to SEQ ID NO: 36.

Preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein the at least one CDRL1 comprises an amino acid sequence according to SEQ ID NO: 37 or a functional sequence variant thereof, the at least one CDRL2 comprises an amino acid sequence according to SEQ ID NO: 38 or 39 or a functional sequence variant thereof, and/or the at least one CDRL3 amino comprises an amino acid sequence according to SEQ ID NO: 40 or a functional sequence variant thereof. It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein the at least one light chain CDRL1 comprises an amino acid sequence according to SEQ ID NO: 37 or a functional sequence variant thereof, the at least one light chain CDRL2 comprises an amino acid sequence according to SEQ ID NO: 38 or 39 or a functional sequence variant thereof, and/or the at least one light chain CDRL3 amino comprising an amino acid sequence according to SEQ ID NO: 58 or a functional sequence variant thereof. Accordingly, it is preferred that the at least one light chain CDRL1 comprises an amino acid sequence sharing at least 80%, preferably at least 85%, more preferably at least 90%, even more preferably at least 95% and particularly preferably at least 98% or 99% sequence identity with SEQ ID NO: 37; the at least one light chain CDRL2 comprises an amino acid sequence sharing at least 80%, preferably at least 85%, more preferably at least 90%, even more preferably at least 95% and particularly preferably at least 98% or 99% sequence identity with SEQ ID NO: 38 or 39; and/or the at least one light chain CDRL3 comprises an amino acid sequence sharing at least 80%, preferably at least 85%, more preferably at least 90%, even more preferably at least 95% and particularly preferably at least 98% or 99% sequence identity with SEQ ID NO: 40 or 58. More preferably, the at least one light chain CDRL1 comprises an amino acid sequence according to SEQ ID NO: 37; the at least one light chain CDRL2 comprises an amino acid sequence according to SEQ ID NO: 38 or 39; and/or the at least one light chain CDRL3 comprises an amino acid sequence according to SEQ ID NO: 40 or 58.

Accordingly, it is also preferred that the antibody, or the antigen binding fragment thereof, according to the present invention comprises CDRH1, CDRH2, and CDRH3 amino acid sequences and CDRL1, CDRL2, and CDRL3 amino acid sequences according to SEQ ID NOs: 34-38 and 40 or functional sequence variants thereof or according to SEQ ID NOs: 34-37 and 39-40 or functional sequence variants thereof, respectively. It is also preferred that the antibody or the antigen binding fragment comprises CDRH1, CDRH2, and CDRH3 amino acid sequences and CDRL1, CDRL2, and CDRL3 amino acid sequences according to SEQ ID NOs: 34, 36-38, 40 and 66 or functional sequence variants thereof or according to SEQ ID NOs: 34, 36-37, 39-40 and 66 or functional sequence variants thereof, respectively. It is also preferred that the antibody or the antigen binding fragment comprises CDRH1, CDRH2, and CDRH3 amino acid sequences and CDRL1, CDRL2, and CDRL3 amino acid sequences according to SEQ ID NOs: 34-38 and 58 or functional sequence variants thereof or according to SEQ ID NOs: 34-37, 39 and 58 or functional sequence variants thereof, respectively. It is furthermore preferred that the antibody or the antigen binding fragment comprises CDRH1, CDRH2, and CDRH3 amino acid sequences and CDRL1, CDRL2, and CDRL3 amino acid sequences according to SEQ ID NOs: 34, 36-38, 58 and 66 or functional sequence variants thereof or according to SEQ ID NOs: 34, 36-37, 39, 58 and 66 or functional sequence variants thereof, respectively.

Accordingly, it is preferred that the antibody or the antigen binding fragment comprises CDRH1, CDRH2, and CDRH3 amino acid sequences and CDRL1, CDRL2, and CDRL3 amino acid sequences (i) sharing at least 80%, preferably at least 85%, more preferably at least 90%, even more preferably at least 95% and particularly preferably at least 98% or 99% sequence identity with each of SEQ ID NOs: 34-38 and 40, respectively; or (ii) sharing at least 80%, preferably at least 85%, more preferably at least 90%, even more preferably at least 95% and particularly preferably at least 98% or 99% sequence identity with each of SEQ ID NOs: 34-37, 39 and 40, respectively; or (iii) sharing at least 80%, preferably at least 85%, more preferably at least 90%, even more preferably at least 95% and particularly preferably at least 98% or 99% sequence identity with each of SEQ ID NOs: 34-38 and 58, respectively; or (iv) sharing at least 80%, preferably at least 85%, more preferably at least 90%, even more preferably at least 95% and particularly preferably at least 98% or 99% sequence identity with each of SEQ ID NOs: 34-37, 39 and 58, respectively; or (v) sharing at least 80%, preferably at least 85%, more preferably at least 90%, even more preferably at least 95% and particularly preferably at least 98% or 99% sequence identity with each of SEQ ID NOs: 34, 36-38, 40 and 66, respectively; or (vi) sharing at least 80%, preferably at least 85%, more preferably at least 90%, even more preferably at least 95% and particularly preferably at least 98% or 99% sequence identity with each of SEQ ID NOs: 34, 36-37, 39, 40 and 66, respectively; or (vii) sharing at least 80%, preferably at least 85%, more preferably at least 90%, even more preferably at least 95% and particularly preferably at least 98% or 99% sequence identity with each of SEQ ID NOs: 34, 36-38, 58 and 66, respectively; or (viii) sharing at least 80%, preferably at least 85%, more preferably at least 90%, even more preferably at least 95% and particularly preferably at least 98% or 99% sequence identity with each of SEQ ID NOs: 34, 36-37, 39, 58 and 66, respectively.

More preferably, the antibody or the antigen binding fragment comprises CDRH1, CDRH2, and CDRH3 amino acid sequences and CDRL1, CDRL2, and CDRL3 amino acid sequences (i) according to SEQ ID NOs: 34-38 and 40, respectively; or (ii) according to SEQ ID NOs: 34-37, 39 and 40, respectively; or (iii) according to SEQ ID NOs: 34-38 and 58, respectively; or (iv) according to SEQ ID NOs: 34-37, 39 and 58, respectively; or (v) according to SEQ ID NOs: 34, 36-38, 40 and 66, respectively; or (vi) according to SEQ ID NOs: 34, 36-37, 39, 40 and 66, respectively; or (vii) according to SEQ ID NOs: 34, 36-38, 58 and 66, respectively; or (viii) according to SEQ ID NOs: 34, 36-37, 39, 58 and 66, respectively.

Moreover, it is also preferred that the antibody, or the antigen binding fragment thereof, according to the present invention comprises a heavy chain variable region (VH) amino acid sequence according to SEQ ID NO: 41 or a functional sequence variant thereof and/or a light chain variable region (VL) amino acid sequence according to SEQ ID NO: 42 or a functional sequence variant thereof. Accordingly, it is preferred that the antibody or the antigen binding fragment comprises a heavy chain variable region (VH) amino acid sequence sharing at least 80%, preferably at least 85%, more preferably at least 90%, even more preferably at least 95% and particularly preferably at least 98% or 99% sequence identity with SEQ ID NO: 41 and a light chain variable region (VL) amino acid sequence sharing at least 80%, preferably at least 85%, more preferably at least 90%, even more preferably at least 95% and particularly preferably at least 98% or 99% sequence identity with SEQ ID NO: 42. More preferably, the antibody or the antigen binding fragment comprises a heavy chain variable region (VH) amino acid sequence according to SEQ ID NO: 41 and a light chain variable region (VL) amino acid sequence according to SEQ ID NO: 42.

Moreover, it is also preferred that the antibody, or the antigen binding fragment thereof, according to the present invention comprises a heavy chain variable region (VH) amino acid sequence according to SEQ ID NO: 41 or 67 or a functional sequence variant thereof and/or a light chain variable region (VL) amino acid sequence according to SEQ ID NO: 42 or a functional sequence variant thereof. Accordingly, it is preferred that the antibody or the antigen binding fragment comprises a heavy chain variable region (VH) amino acid sequence sharing at least 80%, preferably at least 85%, more preferably at least 90%, even more preferably at least 95% and particularly preferably at least 98% or 99% sequence identity with SEQ ID NO: 41 or 67 and a light chain variable region (VL) amino acid sequence sharing at least 80%, preferably at least 85%, more preferably at least 90%, even more preferably at least 95% and particularly preferably at least 98% or 99% sequence identity with SEQ ID NO: 42. More preferably, the antibody or the antigen binding fragment comprises a heavy chain variable region (VH) amino acid sequence according to SEQ ID NO: 41 or 67 and a light chain variable region (VL) amino acid sequence according to SEQ ID NO: 42.

Preferably, the antibody or the antigen binding fragment comprises a heavy chain variable region (VH) amino acid sequence according to SEQ ID NO: 41 or 67 or a functional sequence variant thereof and a light chain variable region (VL) amino acid sequence according to SEQ ID NO: 59 or 65 or a functional sequence variant thereof. Accordingly, it is preferred that the antibody or the antigen binding fragment comprises (i) a heavy chain variable region (VH) amino acid sequence sharing at least 80%, preferably at least 85%, more preferably at least 90%, even more preferably at least 95% and particularly preferably at least 98% or 99% sequence identity with SEQ ID NO: 41 or 67; and (ii) a light chain variable region (VL) amino acid sequence sharing at least 80%, preferably at least 85%, more preferably at least 90%, even more preferably at least 95% and particularly preferably at least 98% or 99% sequence identity with SEQ ID NO: 59 or 65. More preferably, the antibody or the antigen binding fragment comprises a heavy chain variable region (VH) amino acid sequence according to SEQ ID NO:

41 or 67 and a light chain variable region (VL) amino acid sequence according to SEQ ID NO: 59 or 65.

Preferably, the antibody, or the antigen binding fragment thereof, according to the present invention comprises at least one heavy chain CDRH1, CDRH2 and CDRH3 and light chain CDRL1, CDRL2, and CDRL3 amino acid sequences that are at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NO's: 34-38 and 40 or to the amino acid sequences of SEQ ID NOs: 34-37 and 39-40, respectively.

Preferably, the antibody, or the antigen binding fragment thereof, according to the present invention comprises at least one heavy chain CDRH1, CDRH2 and CDRH3 and light chain CDRL1, CDRL2, and CDRL3 amino acid sequences that are at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NO's: 34-38 and 58, respectively, or to the amino acid sequences of SEQ ID NOs: 34-37, 39 and 58, respectively. Preferably, the antibody, or the antigen binding fragment thereof, according to the present invention comprises at least one heavy chain CDRH1, CDRH2 and CDRH3 and light chain CDRL1, CDRL2, and CDRL3 amino acid sequences that are at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NO's: 34, 36-38, 40 and 66, respectively, or to the amino acid sequences of SEQ ID NOs: 34, 36-37, 39-40 and 66, respectively. Preferably, the antibody, or the antigen binding fragment thereof, according to the present invention comprises at least one heavy chain CDRH1, CDRH2 and CDRH3 and light chain CDRL1, CDRL2, and CDRL3 amino acid sequences that are at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NO's: 34, 36-38, 58 and 66, respectively, or to the amino acid sequences of SEQ ID NOs: 34, 36-37, 39, 58 and 66, respectively.

It is also preferred that the antibody, or the antigen binding fragment thereof, according to the present invention comprises at least one heavy chain variable region (VH) and at least one light chain variable region (VL) amino acid sequence that is at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NOs: 41-42.

It is also preferred that the antibody, or the antigen binding fragment thereof, according to the present invention comprises at least one heavy chain variable region (VH) and at least one light chain variable region (VL) amino acid sequence that is at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NOs: 41 and 59.

It is also preferred that the antibody, or the antigen binding fragment thereof, according to the present invention comprises at least one heavy chain variable region (VH) and at least one light chain variable region (VL) amino acid sequence that is at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NOs: 41 and 65.

Particularly preferably, the antibody, or the antigen binding fragment thereof, according to the present invention is gHBC34, in particular, the antibody, or the antigen binding fragment thereof, according to the present invention is HBC34.

The present inventors have isolated a monoclonal antibody (mAb) according to the present invention, which is referred to herein as HBC34 (cf. Example 1). Based on that antibody HBC34, in particular on the VH and VL genes of HBC34, the term "gHBC34", as used herein, refer to a respective "generic" antibody, or antigen binding fragments thereof. Namely, "gHBC34" refers to an antibody, or antigen binding fragment thereof, having a CDRH1 amino acid sequence according to SEQ ID NO: 34, a CDRH2 amino acid sequence according to SEQ ID NO: 35, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 40. In particular, "gHBC34" refers to an antibody, or antigen binding fragment thereof, having a CDRH1 amino acid sequence according to SEQ ID NO: 34, a CDRH2 amino acid sequence according to SEQ ID NO: 35 or 66, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 40. The heavy chain variable region ($V_H$) of "gHBC34" has an amino acid sequence according to SEQ ID NO: 41 and the light chain variable region ($V_L$) of "gHBC34" has an amino acid sequence according to SEQ ID NO: 42.

Particularly preferably, the antibody, or the antigen binding fragment thereof, according to the present invention is gHBC34v7, in particular, the antibody, or the antigen binding fragment thereof, according to the present invention is HBC34v7.

The present inventors have identified a further monoclonal antibody (mAb) according to the present invention, which is referred to herein as HBC34v7 (cf. Example 11). Based on that antibody HBC34v7, in particular on the VH and VL genes of HBC34v7, the term "gHBC34v7", as used herein, refer to a respective "generic" antibody, or antigen binding fragments thereof. Namely, "gHBC34v7" refers to an antibody, or antigen binding fragment thereof, having a CDRH1 amino acid sequence according to SEQ ID NO: 34, a CDRH2 amino acid sequence according to SEQ ID NO: 35 or 66, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 58. The heavy chain variable region ($V_H$) of "gHBC34v7" has an amino acid sequence according to SEQ ID NO: 41 and the light chain variable region ($V_L$) of "gHBC34v7" has an amino acid sequence according to SEQ ID NO: 59.

Particularly preferably, the antibody, or the antigen binding fragment thereof, according to the present invention is gHBC34v23, in particular, the antibody, or the antigen binding fragment thereof, according to the present invention is HBC34v23.

The present inventors have identified a further monoclonal antibody (mAb) according to the present invention, which is referred to herein as HBC34v23 (cf. Example 12). Based on that antibody HBC34v23, in particular on the VH and VL genes of HBC34v23, the term "gHBC34v23", as used herein, refer to a respective "generic" antibody, or antigen binding fragments thereof. Namely, "gHBC34v23" refers to an antibody, or antigen binding fragment thereof, having a CDRH1 amino acid sequence according to SEQ ID NO: 34, a CDRH2 amino acid sequence according to SEQ ID NO: 35 or 66, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 58. The heavy chain variable region ($V_H$) of "gHBC34v23" has an amino acid sequence according to SEQ ID NO: 41 and the light chain variable region ($V_L$) of "gHBC34v23" has an amino acid sequence according to SEQ ID NO: 59.

Particularly preferably, the antibody, or the antigen binding fragment thereof, according to the present invention is gHBC34v31, in particular, the antibody, or the antigen binding fragment thereof, according to the present invention is HBC34v31.

The present inventors have identified a further monoclonal antibody (mAb) according to the present invention, which is referred to herein as HBC34v31 (cf. Example 12). Based on that antibody HBC34v31, in particular on the VH and VL genes of HBC34v31, the term "gHBC34v31", as used herein, refer to a respective "generic" antibody, or antigen binding fragments thereof. Namely, "gHBC34v31" refers to an antibody, or antigen binding fragment thereof, having a CDRH1 amino acid sequence according to SEQ ID NO: 34, a CDRH2 amino acid sequence according to SEQ ID NO: 35 or 66, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 40. The heavy chain variable region ($V_H$) of "gHBC34v31" has an amino acid sequence according to SEQ ID NO: 67 and the light chain variable region ($V_L$) of "gHBC34v31" has an amino acid sequence according to SEQ ID NO: 42.

Particularly preferably, the antibody, or the antigen binding fragment thereof, according to the present invention is gHBC34v32, in particular, the antibody, or the antigen binding fragment thereof, according to the present invention is HBC34v32.

The present inventors have identified a further monoclonal antibody (mAb) according to the present invention, which is referred to herein as HBC34v32 (cf. Example 12). Based on that antibody HBC34v32, in particular on the VH and VL genes of HBC34v32, the term "gHBC34v32", as used herein, refer to a respective "generic" antibody, or antigen binding fragments thereof. Namely, "gHBC34v32" refers to an antibody, or antigen binding fragment thereof, having a CDRH1 amino acid sequence according to SEQ ID NO: 34, a CDRH2 amino acid sequence according to SEQ ID NO: 35 or 66, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 40. The heavy chain variable region ($V_H$) of "gHBC34v32" has an amino acid sequence according to SEQ ID NO: 67 and the light chain variable region ($V_L$) of "gHBC34v32" has an amino acid sequence according to SEQ ID NO: 59.

Particularly preferably, the antibody, or the antigen binding fragment thereof, according to the present invention is gHBC34v33, in particular, the antibody, or the antigen binding fragment thereof, according to the present invention is HBC34v33.

The present inventors have identified a further monoclonal antibody (mAb) according to the present invention, which is referred to herein as HBC34v33 (cf. Example 12). Based on that antibody HBC34v33, in particular on the VH and VL genes of HBC34v33, the term "gHBC34v33", as used herein, refer to a respective "generic" antibody, or antigen binding fragments thereof. Namely, "gHBC34v33" refers to an antibody, or antigen binding fragment thereof, having a CDRH1 amino acid sequence according to SEQ ID NO: 34, a CDRH2 amino acid sequence according to SEQ ID NO: 35 or 66, a CDRH3 amino acid sequence according to SEQ ID NO: 36, a CDRL1 amino acid sequence according to SEQ ID NO: 37, a CDRL2 amino acid sequence according to SEQ ID NO: 38 or 39, and a CDRL3 amino acid sequence according to SEQ ID NO: 40. The heavy chain variable region ($V_H$) of "gHBC34v33" has an amino acid sequence according to SEQ ID NO: 67 and the light chain variable region ($V_L$) of "gHBC34v33" has an amino acid sequence according to SEQ ID NO: 65.

Preferably, the antibody according to the present invention, or the antigen binding fragment thereof, is a human antibody, a monoclonal antibody, a human monoclonal antibody, a purified antibody, a single chain antibody, Fab, Fab', F(ab')2, Fv or scFv.

The antibodies of the invention may thus be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody". The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

In another aspect, the present invention provides the antibody, or the antigen binding fragment thereof, according to the present invention as described herein for use as a medicament. Preferably, the antibody, or the antigen binding fragment thereof, according to the present invention as described herein is for use in the prophylaxis, treatment or attenuation of hepatitis B and/or hepatitis D. A detailed description of that aspect is provided below under "Medical treatment and uses" and in the context of the pharmaceutical composition of the present invention.

Nucleic Acid Molecule

In another aspect, the invention also provides a nucleic acid molecule comprising a polynucleotide encoding the antibody, or the antigen binding fragment thereof, according to the present invention as described above. Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA. Nucleic acid sequences encoding part or all of the light and heavy chains and CDRs of the antibodies of the present invention are preferred. Tables 2-8 provide the SEQ ID numbers for the amino acid sequences of the CDRs and VH and VL of exemplary antibodies according to the present invention, which are preferably encoded by the polynucleotides/nucleic acid sequences as described herein. Preferably provided herein are thus nucleic acid sequences encoding part or all of the light and heavy chains, in particular VH and VL sequences and CDRs of the exemplary antibodies of the invention. Table 9 below provides the SEQ ID numbers for the nucleic acid sequences encoding the CDRs and VH and VL an exemplified antibody according to the present invention. Due to the redundancy of the genetic code, the present invention also comprises sequence variants of these nucleic acid sequences and in particular such sequence variants, which encode the same amino acid sequences.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiesterbonds of a sugar/phosphate-backbone. The term "nucleic acid molecule" also encompasses modified nucleic acid molecules, such as base-modified, sugar-modified or backbone-modified etc. DNA or RNA molecules.

Table 9 shows the nucleic acid sequences of the CDR's and the heavy chain variable region (VH) and the light chain variable region (VL) of exemplary antibodies according to the present invention ("HBC34", "HBC34v7", "HBC34v23", "HBC34v31", "HBC34v32" and "HBC34v33"):

| Name | SEQ ID NO. | Nucleic acid sequence |
|---|---|---|
| HBC34 | | |
| CDRH1 | 43 | GGACGCATCTTTAGAAGTTTTTAC |
| CDRH2 | 44 | ATAAACCAAGATGGAAGTGAGAAA |
| CDRH3 | 45 | GCGGCTTGGAGCGGCAATAGTGGGGGTATGGACGTC |
| CDRL1 | 46 | AAATTGGGGAATAAAAAT |
| CDRL2 | 47 | GAGGTTAAA |
| CDRL2 long | 48 | gtcatctatGAGGTTAAAtaccgcccc |
| CDRL3 | 49 | CAGACGTGGGACAGCACCACTGTGGTG |
| VH | 50 | GAACTGCAGCTGGTGGAGTCTGGGGGAGGCTG GGTCCAGCCGGGGGGGTCCCAGAGACTGTCCT GTGCAGCCTCTGGACGCATCTTTAGAAGTTTTT ACATGAGCTGGGTCCGCCAGGCCCCAGGGAAG GGGCTGGAGTGGGTGGCCACTATAAACCAAGA TGGAAGTGAGAAATTATATGTGGACTCTGTGAA GGGCCGATTCACCATCTCCAGAGACAACGCCAA GAACTCACTATTTCTGCAAATGAACAACCTGAGA GTCGAGGACACGGCCGTTTATTACTGCGCGGCT TGGAGCGGCAATAGTGGGGGTATGGACGTCTG GGGCCAGGGGACCACGGTCTCCGTCTCCTCA |
| VL | 51 | TCCTATGAGCTGACTCAGCCACCCTCAGTGTCCGTG TCCCCAGGACAGACAGTCAGCATCCCCTGCTCTGGA GATAAATTGGGGAATAAAAATGTTTGCTGGTTTCAG CATAAGCCAGGCCAGTCCCCTGTGTTGGTCATCTAT GAGGTTAAATACCGCCCCTCGGGGATTCCTGAGCG ATTCTCTGCTCCAACTCTGGGAACACAGCCACTCT GACCATCAGCGGGACCCAGGCTATGGATGAGGCTG CCTATTTCTGTCAGACGTGGGACAGCACCACTGTG GTGTTCGGCGGAGGGACCAGGCTGACCGTCCTA |
| VH codon optimized | 70 | GAACTGCAGCTGGTCGAATCAGGAGGAGGGTGGGT CCAGCCCGGAGGGGAGCCAGAGACTGTCTTGTGCCG CATCAGGGAGGATCTTCAGGAGCTTCTACATGTCCT GGGTGCGCCAGGCACCAGGCAAGGGACTGGAGTG GGTCGCCACCATCAACCAGGACGGATCTGAAAAGC TGTATGTGGATAGTGTCAAAGGCCGGTTCACAATTA GCAGAGACAACGCTAAAATTCTCTGTTTCTGCAGA TGAACAATCTGCGAGTGGAGGATACCGCCGTCTACT ATTGCGCCGCTTGGTCTGGCAACAGCGGCGGGATGG ATGTCTGGGGCAGGGCACAACAGTGAGCGTCTCT TCC |
| VL codon optimized | 71 | TCATACGAACTGACTCAGCCTCCCTCCGTCTCCGTC TCACCTGGACAGACCGTCTCAATCCCCTGCTCCGGC GATAAACTGGGCAACAAGAACGTGTGCTGGTTCCAGCA CAAACCCGGACAGAGTCCTGTGCTGGTCATCTACGA GGTCAAGTATCGGCCAAGCGGCATTCCCGAAAGATT CAGCGGCTCCAACTCTGGGAATACCGCAACACTGAC TATCTCTGGAACCCAGGCAATGGACGAGGCAGCTTA CTTTTGC**CAGACTTGGGATTCAACTACTGTCGTGTT CGGCGGCGGAACTAGACTGACTGTCCTG |
| CRDH1 codon optimized | 72 | GGGAGGATCTTCAGGAGCTTCTAC |
| CDRH2 codon optimized | 73 | ATCAACCAGGACGGATCTGAAAAG |
| CDRH3 codon optimized | 74 | GCCGCTTGGTCTGGCAACAGCGGCGGGATGGATGTC |
| CDRL1 codon optimized | 75 | AAACTGGGCAACAAGAAC |
| CDRL2 codon optimized | 76 | GAGGTCAAG |
| CDRL2 long codon optimized | 77 | GTCATCTACGAGGTCAAGTATCGGCCA |
| CDRL3 codon optimized | 78 | CAGACTTGGGATTCAACTACTGTCGTG |

| Name | SEQ ID NO. | Nucleic acid sequence |
|---|---|---|
| HBC34v7, HBC34v23, HBC34 v31, HBC34 v32 and HBC34 v33 | | |
| CDRL1 v7 and CDRL1 v23 | 60 | AAGCTGGGGAACAAAAAT |
| CDRL2 v7 and CDRL2 v23 | 61 | GAGGTGAAA |
| CDRL2 long v7 and CDRL2 v23 long | 62 | GTCATCTACGAGGTGAAATATCGGCCT |
| CDRL3 v7 and CDRL3 v23 | 63 | CAGACATTCGATTCCACCACAGTGGTC |
| VL v7 | 64 | TCTTACGAGCTGACACAGCCACCTAGCGTGTCCGTC TCTCCAGGACAGACCGTGTCCATCCCTTGCTCTGGC GACAAGCTGGGGAACAAAAATGTCTGTTGGTTCCA GCACAAGCCAGGGCAGAGTCCCGTGCTGGTCATCTA CGAGGTGAAATATCGGCCTTCAGGAATTCCAGAAC GGTTCAGCGGATCAAACAGCGGCAATACTGCAACCC TGACAATTAGCGGGACCCAGGCCATGGACGAAGCC GCTTATTTCTGCCAGACATTCGATTCCACCACAGTG GTCTTTGGCGGGGGAACTAGGCTGACCGTGCTG |
| HBC34 v31, HBC34 v32 and HBC34 v33 VH | 68 | GAGGTGCAGCTGGTGGAATCCGGCGGGGGACTGG TGCAGCCTGGCGGCTCACTGAGACTGAGCTGTGCA GCTTCTGGAAGAATCTTCAGATCTTTTTACATGAG TTGGGTGAGACAGGCTCCTGGGAAGGGACTGGAGT GGGTCGCAAACATCAATCAGGACGGATCAGAAAAGC TGTATGTGGATAGCGTCAAAGGCAGGTTCACTATT TCCCGCGACAACGCCAAAAATTCTCTGTTTCTGCAG ATGAACAATCTGCGGGTGGAGGATACCGCTGTCTA CTATTGTGCAGCCTGGTCTGGCAACAGTGGAGGCA TGGACGTGTGGGGACAGGGAACCACAGTGACAGTC AGCTCC |
| VL v23 | 69 | TCTTACGAGCTGACACAGCCCCCTAGCGTGTCCGTC TCTCCAGGCCAGACAGCATCCATCACTTGCTCTGGC GACAAGCTGGGGAACAAAAATGCCTGTTGGTATCA GCAGAAGCCAGGGCAGAGTCCCGTGCTGGTCATCT ACGAGGTGAAATATCGGCCTTCAGGAATTCCAGAAA GATTCAGTGGATCAAACAGCGGCAATACTGCTACCC TGACAATTAGCGGGACCCAGGCCATGGACGAAGCT GATTACTATTGCCAGACATTCGATTCCACCACAGTG GTCTTTGGCGGGGGAACTAAGCTGACCGTGCTG |

Preferably, the sequence of the nucleic acid molecule according to the present invention comprises or consists of a nucleic acid sequence according to any one of SEQ ID NOs: 43-51 or a functional sequence variant thereof. It is also preferred that the sequence of the nucleic acid molecule according to the present invention comprises or consists of a nucleic acid sequence according to any one of SEQ ID NOs: 43-51, 60-64 and 68-78.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a CDR, a VH sequence and/or a VL sequence used in an (exemplary) antibody according to the present invention, for example to the sequences shown in Table 9. Thus a nucleic acid molecule is preferred, wherein the polynucleotide sequence comprises or consists of a nucleic acid sequence according to any one of SEQ ID NOs: 43-51 or a functional sequence variant thereof.

A nucleic acid molecule, wherein the polynucleotide sequence comprises or consists of a nucleic acid sequence sharing at least 80%, preferably at least 85%, more preferably at least 90%, even more preferably at least 95% and particularly preferably at least 98% or 99% sequence identity with any of SEQ ID NOs: 43-51, 60-64 and 68-78 is also preferred. More preferably, the polynucleotide sequence comprises or consists of a nucleic acid sequence according to any one of SEQ ID NOs: 43-51, 60-64 and 68-78.

More preferably, the polynucleotide sequence comprises or consists of a nucleic acid sequence sharing at least 80%, preferably at least 85%, more preferably at least 90%, even more preferably at least 95% and particularly preferably at least 98% or 99% sequence identity with any of SEQ ID NOs: 70-78. SEQ ID NOs: 70-78 are codon-optimized nucleic acid sequences (cf. Table 9). Particularly preferably the polynucleotide sequence comprises or consists of a nucleic acid sequence according to any one of SEQ ID NOs: 70-78.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, a VH sequence and/or a VL sequence of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Vector

Further included within the scope of the invention are vectors, for example, expression vectors, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Cells

In a further aspect, the present invention also provides cell expressing the antibody, or the antigen binding fragment thereof, according to the present invention; and/or comprising the vector according the present invention.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NS0 cells, human liver cells, e.g. Hepa RG cells, myeloma cells or hybridoma cells.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention, e.g. for expressing the antibody, or the antigen binding fragment thereof, according to the present invention. Preferably, the cells are stably transfected with the vector according to the present invention encoding the antibody, or the antigen binding fragment thereof, according to the present invention. Alternatively, it is also preferred that the cells are transiently transfected with the vector according to the present invention encoding the antibody, or the antigen binding fragment thereof, according to the present invention.

Optional Additional Features of the Antibodies

Antibodies of the invention may be coupled, for example, to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest on HBsAg, in particular on the antigenic loop region of HBsAg, can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. Labeled antibodies according to the present invention may be thus be used in such assays for example as described in U.S. Pat. Nos. 3,766,162; 3,791,932; 3,817,837; and 4,233,402.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention, e.g., as described in U.S. Pat. No. 4,831,175. Antibodies or, antigen-binding fragments thereof may be directly labeled with radioactive iodine, indium, yttrium, or other radioactive particle known in the art, e.g., as described in U.S. Pat. No. 5,595,721. Treatment may consist of a combination of treatment with conjugated and non-conjugated antibodies administered simultaneously or subsequently e.g., as described in WO00/52031; WO00/52473.

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: $R(O-CH_2-CH_2)_nO-R$, wherein R can be hydrogen, or a protective group such as an alkyl or alkanol group. Preferably, the protective group may have between 1 and 8 carbons. For example, the protective group is methyl. The symbol n is a positive integer. In one embodiment n is between 1 and 1,000. In another embodiment n is between 2 and 500. Preferably, the PEG has an average molecular weight between 1,000 and 40,000, more preferably the PEG has a molecular weight between 2,000 and 20,000, even more preferably the PEG has a molecular weight between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. In particular, antibodies of the invention for human use include those that cannot be easily isolated from hosts such as mice, goats, rabbits, rats, non-primate mammals, etc. and cannot generally be obtained by humanization or from xeno-mice.

Production of Antibodies

Antibodies according to the invention can be made by any method known in the art. For example, the general methodology for making monoclonal antibodies using hybridoma technology is well known (Kohler, G. and Milstein, C., 1975; Kozbar et al. 1983). In one embodiment, the alternative EBV immortalization method described in WO2004/076677 is used.

A preferred method is described in WO 2004/076677. In this method B cells producing the antibody of the invention are transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Another preferred method is described in WO 2010/046775. In this method plasma cells are cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fabs, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by (i) expressing a nucleic acid sequence according to the invention in a host cell, e.g. by use of a vector according to the present invention, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention also provides a composition comprising immortalized B memory cells or transfected host cells that produce antibodies according to the present invention.

The immortalized B cell clone or the cultured plasma cells of the invention may also be used as a source of nucleic acid for the cloning of antibody genes for subsequent recombinant expression.

Expression from recombinant sources is more common for pharmaceutical purposes than expression from B cells or hybridomas e.g., for reasons of stability, reproducibility, culture ease, etc.

Thus the invention also provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

Furthermore, the invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NS0 cells, human cells such as PER.C6 or HKB-11 cells, myeloma cells, or a human liver cell, such as Hepa RG), as well as plant cells, whereby mammalian cells are preferred. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of: (i) preparing an immortalized B cell clone or culturing plasma cells according to the invention; (ii) obtaining from the B cell clone or the cultured plasma cells nucleic acid that encodes the antibody of interest. Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention further provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention also comprises a method for preparing an antibody (e.g., for pharmaceutical use) according to the present invention, comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population, e.g. a stably transfected host cell population, under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., in different countries).

Pharmaceutical Compositions

The present invention also provides a pharmaceutical composition comprising one or more of:
(i) the antibody, or the antibody fragment thereof, according to the present invention;
(ii) the nucleic acid encoding the antibody, or antibody fragments according to the present invention;
(iii) the vector comprising the nucleic acid according to the present invention; or
(iv) the cell expressing the antibody according to the present invention or comprising the vector according to the present invention.

In other words, the present invention also provides a pharmaceutical composition comprising the antibody, or the antigen binding fragment thereof, according to the present invention, the nucleic acid according to the present invention, the vector according to the present invention and/or the cell according to the present invention.

The pharmaceutical composition may preferably also contain a pharmaceutically acceptable carrier, diluent and/or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components. Preferably, the pharmaceutically acceptable carrier in a pharmaceutical composition according to the present invention is not an active component in respect to hepatitis B or D.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody may be provided in kit form with sterile water or a sterile buffer.

It is preferred that the active ingredient in the composition is an antibody molecule, an antibody fragment or variants and derivatives thereof, in particular the active ingredient in the composition is an antibody, an antibody fragment or variants and derivatives thereof, according to the present invention. As such, it may be susceptible to degradation in the gastrointestinal tract. Thus, if the composition is to be administered by a route using the gastrointestinal tract, the composition may contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid. A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Preferably, the pharmaceutical composition may be prepared for oral administration, e.g. as tablets, capsules and the like, for topical administration, or as injectable, e.g. as liquid solutions or suspensions, whereby it is particularly preferred that the pharmaceutical composition is an injectable. Solid forms suitable for solution in, or suspension in, liquid vehicles prior to injection are also be preferred, e.g. that the pharmaceutical composition is in lyophilized form.

For injection, e.g. intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule, whereby in the context of the present invention a multiple dose schedule is preferred. Known antibody-based pharmaceuticals, in particular anti-HBV based pharmaceuticals, e.g. Hepatect® CP, provide guidance relating to frequency of administration in particular in respect to different indications, e.g., whether a pharmaceutical should be delivered daily, weekly, monthly, etc. Frequency and dosage may also depend on the severity of symptoms.

For example, the pharmaceutical composition according to the present invention may be administered daily, e.g. once or several times per day, e.g. once, twice, three times or four times per day, preferably once or twice per day, more preferable once per day, for 1, 2, 3, 4, 5, 6, 7, 8, 9, 10, 11, 12, 13, 14, 15, 16, 17, 18, 19, 20 or 21 or more days, e.g. daily for 1, 2, 3, 4, 5, 6 months. Preferably, the pharmaceutical composition according to the present invention may be administered weekly, e.g. once or twice per week, for 1, 2, 3, 4, 5, 6, 7, 8, 9, 10, 11, 12, 13, 14, 15, 16, 17, 18, 19, 20 or 21 or more weeks, e.g. weekly for 1, 2, 3, 4, 5, 6, 7, 8, 9, 10, 11, or 12 months or weekly for 2, 3, 4, or 5 years. Moreover, the pharmaceutical composition according to the present invention may be preferably administered monthly, e.g. once per month or, more preferably, every second month for 1, 2, 3, 4, or 5 or more years. A preferred endpoint of administration is when seroconversion is reached, preferably the endpoint of therapy is the persistent disappearance of HBsAg from serum, accompanied by seroconversion to anti-HBV antibodies. It is also preferred that the administration continues for the lifetime. In addition, also one single administration only is also envisaged, in particular in respect to certain indications, e.g. for prevention of hepatitis B in case of accidental exposure in non-immunised subjects.

In particular, it is preferred that for a single dose, e.g. a daily, weekly or monthly dose, preferably for a weekly dose, the amount of the antibody, or the antigen binding fragment thereof, in the pharmaceutical composition according to the present invention, does not exceed 1 g, preferably does not exceed 500 mg, more preferably does not exceed 250 mg, even more preferably does not exceed 100 mg, and particularly preferably does not exceed 50 mg.

Pharmaceutical compositions typically include an "effective" amount of one or more antibodies of the invention, i.e. an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 50 mg/kg, more preferably from about 0.01 to about 10 mg/kg, and even more preferably from about 0.02 to about 5 mg/kg, of the antibody of the present invention (e.g. amount of the antibody in the pharmaceutical composition) in relation to the bodyweight (e.g., in kg) of the individual to which it is administered.

For example, in the context of liver transplantation, e.g. due to hepatitis B induced liver failure, the amount of the antibody, or the antigen binding fragment thereof, in the pharmaceutical composition according to the present invention, may preferably not exceed 50 mg, more preferably not more than 10 mg, for a single dose on the day of transplantation, peri-operatively then not more than 10-50 mg, preferably not more than 2-10 mg, per day for seven days and not more than 10-50 mg, preferably not more than 2-10 mg, per single dose administered every 1-3 months to maintain anti-HBs serum levels about 100 IU/L.

For the treatment of chronic hepatitis B, for example, the antibody, or the antigen binding fragment thereof, or the pharmaceutical composition according to the present invention, is preferably administered subcutaneously, with a single dose of up to 500 mg, preferably of up to 250 mg, more preferably of up to 100 mg of the antibody according to the present invention. Such a single dose may be administered daily, weekly or monthly as described above.

Moreover, the pharmaceutical composition according to the present invention may also comprise an additional active component, which may be a further antibody or a component, which is not an antibody. The additional active component is preferably selected from polymerase inhibitors, interferons and/or checkpoint inhibitors. Preferred polymerase inhibitors include Lamivudine, Adefovir, Entecavir, Telbivudine and Tenofovir. Polymerase inhibitors suppress reverse transcription and synthesis of the DNA-plus strand. Polymerase inhibitors do not prevent viral spread, formation of cccDNA and does not affect HBsAg release. Interferons include IFNalpha and IFNbeta, whereby IFNbeta is preferred. Preferred checkpoint inhibitors are directed to a blockade of PD-1/PD-L1 and/or of CTLA4 and, thus, include anti-PD-1 antibodies, anti-PD-L1 antibodies and anti-CTLA4 antibodies. The pharmaceutical composition according to the present invention may comprise one or more of the additional active components.

The antibody, or the antigen binding fragment, according to the present invention can be present either in the same pharmaceutical composition as the additional active component or, preferably, the antibody, or the antigen binding fragment, according to the present invention is comprised by a first pharmaceutical composition and the additional active component is comprised by a second pharmaceutical composition different from the first pharmaceutical composition. Accordingly, if more than one additional active component is envisaged, each additional active component and the antibody, or the antigen binding fragment, according to the present invention is preferably comprised by a different pharmaceutical composition. Such different pharmaceutical compositions may be administered either combined/simultaneously or at separate times or at separate locations (e.g. separate parts of the body).

Preferably, antibody, or the antigen binding fragment, according to the present invention and the additional active component provide an additive therapeutic effect or, preferably, a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

A pharmaceutical composition comprising the antibody according to gHCB34 or an antigen binding fragment thereof, and a pharmaceutically acceptable carrier is preferred.

In one embodiment, a composition of the invention may include antibodies of the invention, wherein the antibodies may make up at least 50% by weight (e.g., 60%, 70%, 75%, 80%, 85%, 90%, 95%, 96%, 97%, 98%, 99% or more) of the total protein in the composition. In such a composition, the antibodies are preferably in purified form.

The present invention also provides a method of preparing a pharmaceutical composition comprising the steps of: (i) preparing an antibody of the invention; and (ii) admixing the purified antibody with one or more pharmaceutically-acceptable carriers.

In another embodiment, a method of preparing a pharmaceutical composition comprises the step of admixing an antibody with one or more pharmaceutically-acceptable carriers, wherein the antibody is a monoclonal antibody that was obtained from a transformed B cell or a cultured plasma cell of the invention.

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Pharmaceutical compositions may include an antimicrobial, particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. For example, a concentration of 10±2 mg/ml NaCl is typical.

Further, pharmaceutical compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

The compositions of the invention may also comprise one or more immunoregulatory agents. In one embodiment, one or more of the immunoregulatory agents include(s) an adjuvant.

Medical Treatments and Uses

In a further aspect, the present invention provides the use of an antibody, or an antigen binding fragment thereof, according to the present invention, the nucleic acid according to the present invention, the vector according to the present invention, the cell according to the present invention or the pharmaceutical composition according to the present invention in (i) prophylaxis, treatment or attenuation of hepatitis B and/or hepatitis D; or in (ii) diagnosis of hepatitis B and/or hepatitis D.

Within the scope of the invention are several forms and routes of administration of the antibody, or the antigen binding fragment thereof, the nucleic acid, the vector, the cell or the pharmaceutical composition, as described above in respect to the pharmaceutical composition. This applies also in the context of the use of the antibody, or the antigen binding fragment thereof, the nucleic acid, the vector, and the cell as described herein, in particular regarding preferred forms and routes of administration.

Methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably serum. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

The invention also provides the use of (i) an antibody, an antibody fragment, or variants and derivatives thereof according to the invention, (ii) an immortalized B cell clone according to the invention, (iii) a nucleic acid or a vector according to the present invention or (iv) a pharmaceutical composition of the invention in (a) the manufacture of a medicament for the prevention, treatment or attenuation of hepatitis B and/or hepatitis D or for (b) diagnosis of hepatitis B and/or hepatitis D.

The invention also provides the antibody, or an antigen binding fragment thereof, according to the present invention, the nucleic acid according to the present invention, the vector according to the present invention, the cell according to the present invention or the pharmaceutical composition according to the present invention for use as a medicament, in particular for the prevention or treatment of hepatitis B and/or hepatitis D. It also provides the use of an antibody of the invention in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, or pharmaceutical composition according to the invention is administered to a subject in need of such treatment. Such a subject includes, but is not limited to, one who is particularly at risk of or susceptible to hepatitis B and/or hepatitis D.

Antibodies, or antigen binding fragments thereof, according to the present invention may also be used in a kit for the diagnosis of hepatitis B and/or hepatitis D. Further, the epitope in the antigenic loop region of HBsAg, which is capable of binding an antibody of the invention as described herein may be used in a kit for monitoring the efficacy of application procedures by detecting the presence or determining the titer of protective anti-HBV antibodies.

Preferably, the antibody, or an antigen binding fragment thereof, according to the present invention, the nucleic acid according to the present invention, the vector according to the present invention, the cell according to the present invention or the pharmaceutical composition according to the present invention is used in treatment or attenuation of chronic hepatitis B.

Interestingly, the antibody according to the present invention (i) potently neutralizes HBV infection, (ii) binds to L-HBsAg (the large HBV envelope protein, which is present in infectious HBV particles), thereby preventing spreading of HBV, (iii) binds to S-HBsAg, thereby promoting clearance of subviral particles (SVP) and (iv) can induce seroconversion, i.e. an active immune response to the virus.

Preferably, the antibody, or an antigen binding fragment thereof, according to the present invention, the nucleic acid according to the present invention, the vector according to the present invention, the cell according to the present invention or the pharmaceutical composition according to the present invention is used in prevention of hepatitis B (re-)infection after liver transplantation in particular for hepatitis B induced liver failure.

To this end, preferably a high dose may be administered to the patient receiving a liver transplantation on the day of transplantation and daily doses are given peri-operatively for about a week. Thereafter, preferably further doses may be given every 1-3 months to maintain anti-HBV antibody serum levels above 100 IU/ml.

In another preferred embodiment the antibody, or an antigen binding fragment thereof, according to the present invention, the nucleic acid according to the present invention, the vector according to the present invention, the cell according to the present invention or the pharmaceutical composition according to the present invention is used in prevention/prophylaxis of hepatitis B in non-immunized subjects. This is for example in case of (an assumed) accidental exposure to HBV (post-exposure prophylaxis). The term "non-immunized subjects" includes subjects, who never received a vaccination and are, thus, not immunized, and subjects, who did not show an immune response (no measurable anti-hepatitis B antibodies) after vaccination. In particular in the latter group, the antibody, or an antigen binding fragment thereof, according to the present invention, the nucleic acid according to the present invention, the vector according to the present invention, the cell according to the present invention or the pharmaceutical composition according to the present invention is used in (continuous) prevention of hepatitis B, i.e. in contrast to "post-exposure prophylaxis" (continuous) prevention is preferably for such subjects, who did not show an immune response (no measurable anti-hepatitis B antibodies) after vaccination and for whom continuous prevention is necessary.

Preferably, the antibody, or an antigen binding fragment thereof, according to the present invention, the nucleic acid according to the present invention, the vector according to the present invention, the cell according to the present invention or the pharmaceutical composition according to the present invention is used in prophylaxis of hepatitis B in haemodialysed patients.

Preferably, the antibody, or an antigen binding fragment thereof, according to the present invention, the nucleic acid according to the present invention, the vector according to the present invention, the cell according to the present invention or the pharmaceutical composition according to the present invention is used in prevention of hepatitis B in the newborn. Thereby, in particular newborns of hepatitis B virus carrier-mothers/non-immunized mothers are preferred. Moreover, it is preferred that the antibody, or an antigen binding fragment thereof, according to the present invention, the nucleic acid according to the present invention, the vector according to the present invention, the cell according to the present invention or the pharmaceutical composition according to the present invention is administered at birth or as soon as possible after birth. Preferably, the administration may be repeated until seroconversion following vaccination.

Preferably, the antibody, or an antigen binding fragment thereof, according to the present invention, the nucleic acid according to the present invention, the vector according to the present invention, the cell according to the present invention or the pharmaceutical composition according to the present invention is used in treatment or attenuation of hepatitis D, preferably of hepatitis B and hepatitis D, which is in particular a hepatitis B and hepatitis D comorbidity. Interestingly, the antibody according to the present invention does not only potently neutralize hepatitis B virus, but also hepatitis delta virus. Therefore, the antibody according to the present invention may provide a first treatment of hepatitis D.

Combination Therapy

The administration of the antibody, or an antigen binding fragment thereof, according to the present invention, the nucleic acid according to the present invention, the vector according to the present invention, the cell according to the present invention or the pharmaceutical composition according to the present invention in the methods and uses according to the invention can be carried out alone or in combination with a co-agent (also referred to as "additional active component" herein) useful for treating and/or stabilizing the disease or disorder to be treated or repressed.

The invention encompasses the administration of the antibody, or an antigen binding fragment thereof, according to the present invention, the nucleic acid according to the present invention, the vector according to the present invention, the cell according to the present invention or the pharmaceutical composition according to the present invention, wherein it is administered to a subject prior to, simultaneously or sequentially with other therapeutic regimens or co-agents useful for treating, and/or preventing hepatitis B. Said antibody, nucleic acid, vector, cell or pharmaceutical composition, that is administered simultaneously with said co-agents can be administered in the same or different composition(s) and by the same or different route(s) of administration.

Said other therapeutic regimens or co-agents may be selected from the group consisting of polymerase inhibitors, interferons and/or a checkpoint inhibitors.

Thus, in another aspect of the present invention the antibody, or an antigen binding fragment thereof, according to the present invention, the nucleic acid according to the present invention, the vector according to the present invention, the cell according to the present invention or the pharmaceutical composition according to the present invention is administered in combination with a polymerase inhibitor, an interferon and/or a checkpoint inhibitor for the above described (medical) uses.

Preferred polymerase inhibitors include Lamivudine, Adefovir, Entecavir, Telbivudine and Tenofovir. Lamivudine is the most preferred polymerase inhibitor. Polymerase inhibitors suppress revers transcription and synthesis of the DNA-plus strand. Polymerase inhibitors do not prevent viral spread, formation of cccDNA and does not affect HBsAg release.

Interferons include IFNalpha and IFNbeta, whereby IFNbeta is preferred.

Preferred checkpoint inhibitors are directed to a blockade of PD-1/PD-L1 and/or of CTLA4 and, thus, include anti-PD-1 antibodies, anti-PD-L1 antibodies and anti-CTLA4 antibodies. Thus, the pharmaceutical composition according to the present invention may comprise one or more of the additional active components.

Further preferred co-agent (additional active components) to be administered in combination with the antibody, or an antigen binding fragment thereof, according to the present invention, the nucleic acid according to the present invention, the vector according to the present invention, the cell according to the present invention or the pharmaceutical composition according to the present invention include LTβR agonists.

Preferably, the antibody, or the antigen binding fragment thereof, according to the present invention, the nucleic acid according to the present invention, the vector according to the present invention, the cell according to the present invention or the pharmaceutical composition according to the present invention is administered in combination with a polymerase inhibitor. This applies in particular for a use of such a combination in prophylaxis, treatment or attenuation of hepatitis B and/or hepatitis D. In this context, preferred polymerase inhibitors include Lamivudine, Adefovir, Entecavir, Telbivudine and Tenofovir. The most preferred polymerase inhibitor is lamivudine.

Preferably, the antibody, or the antigen binding fragment thereof, the nucleic acid, the vector, the cell or the pharmaceutical composition is administered via the same or a distinct route of administration as the polymerase inhibitor, the interferon and/or the checkpoint inhibitor.

In a further aspect the present invention thus also provides a combination of
  (i) the antibody, or the antigen binding fragment thereof, according to the present invention, the nucleic acid according to the present invention, the vector according to the present invention, the cell according to the present invention or the pharmaceutical composition according to the present invention; and (ii) a polymerase inhibitor, an interferon and/or a checkpoint inhibitor.

Such a combination is preferably used in prophylaxis, treatment or attenuation of hepatitis B and/or hepatitis D, in particular in treatment or attenuation of chronic hepatitis B and/or chronic hepatitis D. More preferably, the combination is used in HBV mono-infected patients or in HBV/HDV co-infected patients.

Such a combination preferably accelerates HBsAg clearance.

In view thereof, the present invention also provides a kit comprising
  (i) the antibody, or the antigen binding fragment thereof, according to the present invention, the nucleic acid according to the present invention, the vector according to the present invention, the cell according to the present invention or the pharmaceutical composition according to the present invention; and
  (ii) a polymerase inhibitor, an interferon and/or a checkpoint inhibitor.

In addition, the kit may comprise means for administration of the antibody, or an antigen binding fragment thereof, according to the present invention, the nucleic acid according to the present invention, the vector according to the present invention, the cell according to the present invention or the pharmaceutical composition according to the present invention, such as a syringe or a vessel and/or a leaflet, for example with instructions on the use of the antibody, or the antigen binding fragment thereof, according to the present invention, the nucleic acid according to the present invention, the vector according to the present invention, the cell according to the present invention or the pharmaceutical composition according to the present invention and/or the polymerase inhibitor, the interferon and/or the checkpoint inhibitor.

The antibody, or the antigen binding fragment, according to the present invention can be present either in the same pharmaceutical composition as the additional active component (co-agent) or, preferably, the antibody, or the antigen binding fragment, according to the present invention is comprised by a first pharmaceutical composition and the additional active component (co-agent) is comprised by a second pharmaceutical composition different from the first pharmaceutical composition. Accordingly, if more than one additional active component (co-agent) is envisaged, each additional active component (co-agent) and the antibody, or the antigen binding fragment, according to the present invention is preferably comprised by a different pharmaceutical composition. Such different pharmaceutical compositions may be administered either combined/simultaneously or at separate times or at separate locations (e.g. separate parts of the body).

Preferably, antibody, or the antigen binding fragment, according to the present invention and the additional active component (co-agent) provide an additive therapeutic effect or, preferably, a synergistic therapeutic effect. As described above, the term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Uses and Methods

In another aspect the present invention provides the use of the antibody, or an antigen binding fragment thereof, according to the present invention, the nucleic acid according to the present invention, the vector according to the present invention, the cell according to the present invention or the pharmaceutical composition according to the present invention for monitoring the quality of anti-hepatitis-B or anti-hepatitis-D vaccines by checking that the antigen of said vaccine contains the specific epitope in the correct conformation.

Moreover, the present invention also provides the use of the antibody, or an antigen binding fragment thereof, according to the present invention, the nucleic acid according to the present invention, the vector according to the present invention, the cell according to the present invention or the pharmaceutical composition according to the present invention in diagnosis of hepatitis B and/or hepatitis D.

In addition also the use of the antibody, or an antigen binding fragment thereof, according to the present invention, the nucleic acid according to the present invention, the vector according to the present invention, the cell according to the present invention or the pharmaceutical composition according to the present invention in determining whether an isolated blood sample is infected with hepatitis B virus and/or hepatitis delta virus is provided.

As described above, methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably serum. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

The present invention also provides a method of preventing and/or treating hepatitis B and/or hepatitis D in a subject, wherein the method comprises administering to a subject in need thereof the antibody, or an antigen binding fragment thereof, according to the present invention, the nucleic acid according to the present invention, the vector according to the present invention, the cell according to the present invention or the pharmaceutical composition according to the present invention.

The present invention also provides a method of treating a subject who has received a liver transplant comprising administering to the subject who has received the liver transplant, a therapeutically effective amount of the antibody, or an antigen binding fragment thereof, according to the present invention, the nucleic acid according to the present invention, the vector according to the present invention, the cell according to the present invention or the pharmaceutical composition according to the present invention.

In the above methods a subject suffering from chronic hepatitis B is preferred.

Moreover, the previously described details, in particular in the context of the pharmaceutical composition and the medical uses, also apply for the methods described herein. For example, in the methods described above the antibody, or an antigen binding fragment thereof, according to the present invention, the nucleic acid according to the present invention, the vector according to the present invention, the cell according to the present invention or the pharmaceutical composition according to the present invention is preferably administered in combination with a polymerase inhibitor, an interferon and/or a checkpoint inhibitor as described herein.

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 5 shows for Example 3 the amino acid sequences of the antigenic loop of HBsAg of the 10 HBV genotypes A, B. C. D, E, F, G, H, I and J. Those sequences comprise the epitope recognized by the HBC34 antibody (highlighted in grey). The sequence on the top (HBV-D J02203) was used to design the peptide library in Example 5, FIG. 7.

FIG. 17 (part 2-5) show for Example 9 the magnitude of binding (ELISA intensities) of HBC34 to 16 different sets of peptides. HBC34 is binding to a conformational epitope as demonstrated by the binding to peptides of sets 13-16 composed of combinatorial CLIPS constructs, representing two parts of a discontinuous epitope (part 2) and to peptides of sets 9-12 composed of looped peptides (part 3). No binding of HBC34 is observed with sets of linear peptides 1-4 (part 4) and 5-8 (part 5) further supporting the notion that HBC34 binds to a discontinuous conformational epitope.

FIG. 18 shows binding of HBC34 to sets 1-3 where residues at the boxed positions were substituted with by one of 13 amino acids selected from series AEFGHKLPQRSVY_ (SEQ ID NO:92), where "_" stands for residue deletion. The original residue at the permutated position is indicated on the left of each panel as well as either (i) in the horizontally boxed sequence (when the original amino acid is part of the permutation series) or (ii) below the sequence (when the original amino acid is not part of the permutation series).

FIG. 20 shows for Examples 11 and 12 the alignments of the two sets of VH (panel A) and VL (panel B) sequences generated to obtain the antibody variants 1-32. CDRs (defined according to IMGT) are highlighted in grey.

FIG. 21 shows for Example 11 the binding of 18 engineered HBC34 variants (obtained by combining the mutated VH and VL sequences as indicated in columns 2 and 3) to HBsAg (adw subtype) as determined by ELISA. In columns 4, loss of binding is indicated with "−", strongly reduced binding is indicated with "+/−", reduced binding is indicated with "+/−", binding similar or equal to the original antibody is indicated with "+".

FIG. 23 shows for Example 11 the summary of the characteristics of the 8 antibodies described in FIG. 22. EC50 were determined by fitting the curves in FIG. 22 using Graphpad prism. Productivity was determined by (ELISA) quantification of secreted IgG in the supernatant of a 300 ml transfection of 293 Expi cells with each of the 8 variants as well as the parental antibody.

FIG. 24 shows for Examples 11 and 12 a table summarizing the characteristics of 15 variants, among which are 12 additional engineered variants of HBC34, designed based on the results of the previous set by introducing additional mutations in the frameworks (panel A). Binding curves were obtained by titrating the antibodies in antigen-based ELISA assay and EC50 were calculated by fitting the curves with Graphpad prism. Productivities were calculated based on quantification of the IgG secreted in the supernatant of a 30 ml transfection of 293 Expi cells with each of the 15 variants and the parental antibody. Fold-changes were plotted and are shown in panel B.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Identification and Characterization of Human Monoclonal Antibody HBC34

A human monoclonal antibody was isolated in a similar manner as described in Traggiai E. et al., 2004, Nat Med 10(8): 871-5 from a human patient. The antibody was characterized by determining the nucleotide and amino acid sequences of its variable regions (Tables 2 and 3) and the complementarity determining regions (CRDs) therein and termed "HBC34". Accordingly, HBC34 is an IgG1-type fully human monoclonal antibody having the CDR, VH and VL sequences as shown above in Tables 2 and 3.

Figure 1:
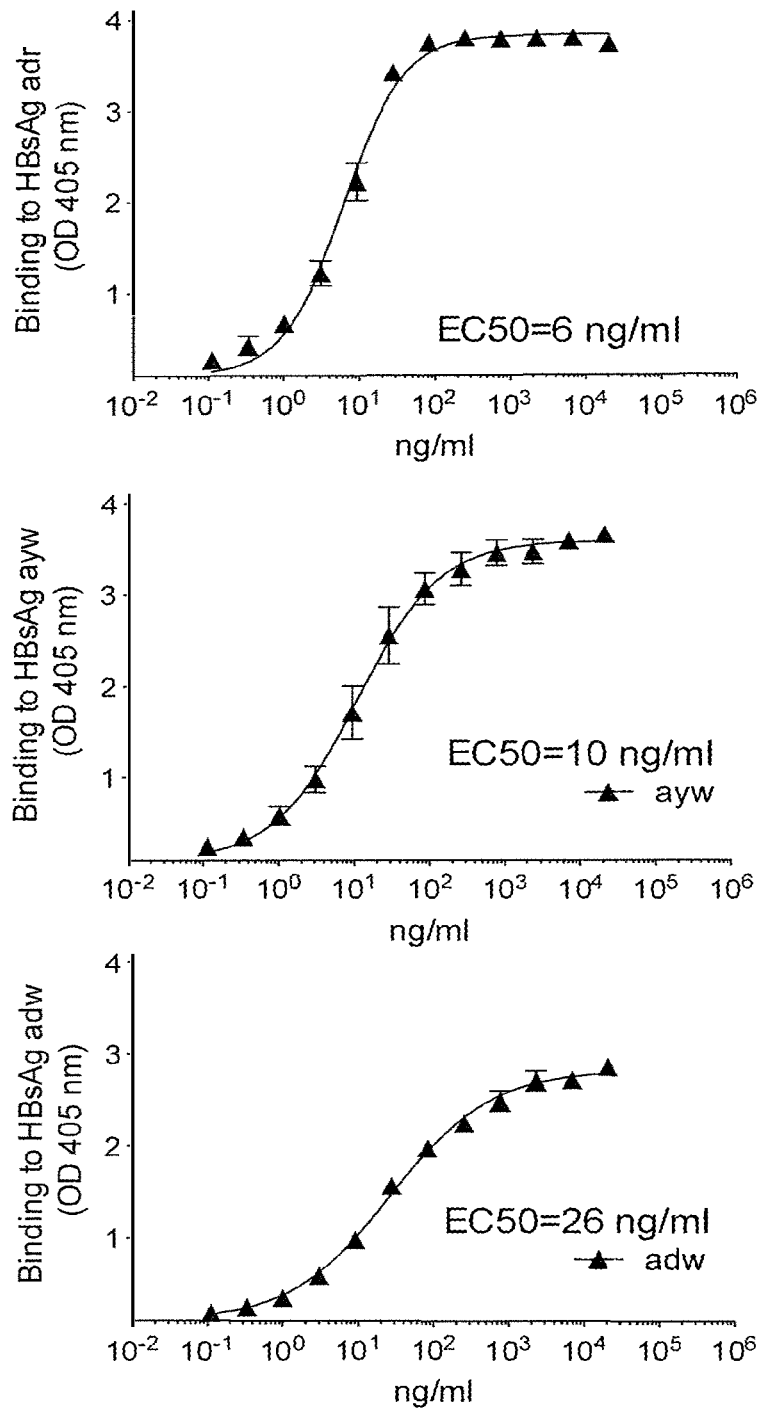
FIG. 1 shows for Example 1 the binding of HBC34 monoclonal antibody to three different HBsAg serotypes (adw, ady, and ayw) as measured by ELISA.

Next, it was determined to which of the three HBsAg serotypes adw, ady, and ayw the human monoclonal antibody HBC34 binds to. Interestingly, HBC34 binds with high affinity to three HBsAg serotypes (adw, ady and ayw) with similar and low EC50 values, as measured by ELISA (FIG. 1).

Protective titers of HBV antibodies are expressed in International Units (IU) which allows standardization over different assays. In 1977, an International Reference Preparation for anti-HBs immunoglobulin (W1042) was established. The plasma used in the preparation of this standard was derived from individuals who had been naturally infected with hepatitis B virus (Barker, L. F., D. Lorenz, S. C. Rastogi, J. S. Finlayson, and E. B. Seligmann. 1977. Study of a proposed international reference preparation for antihepatitis B immunoglobulin. WHO Expert Committee on Biological Standardization technical report series. WHO Expert Committee on Biological Standardisation 29th Report BS 77.1 164. Geneva, Switzerland, World Health Organization, 1977; World Health Organization: Anti-hepatitis B immunoglobulin. WHO Tech Rep Ser 1978; 626:18). The activity of HBC34, as measured diagnostically with an immunoassay (Abbott Architect diagnostic immunoassay), is 5000 IU/mg. As a comparison the activity of HBIG is ~1 IU/mg.

Example 2: Antibody HBC34 Potently Neutralizes Infectious HBV and HDV

The first object of Example 2 was to determine whether HBC34 neutralizes infectious HBV and to compare the neutralization activity of HBC34 to that of other anti-HB antibodies. To this end, differentiated HepaRG cells were incubated with a fixed amount of HBV in the presence or absence of antibodies (HBC34, 18/7, Ab2, Ab3 and HBIG) in medium supplemented with 4% PEG 8000 (Sigma-Aldrich) for 16 hours at 37° C. At the end of the incubation, the cells were washed and further cultivated. Medium was changed every 3 days. Infection was detected by measuring in enzyme-linked immunosorbent assay (ELISA) the levels of hepatitis B surface antigen (HBsAg) and hepatitis B e antigen (HBeAg) secreted into the culture supernatant from day 7 to 11 post-infection and by detecting HBcAg staining in an immunofluorescence assay.

Figure 2:
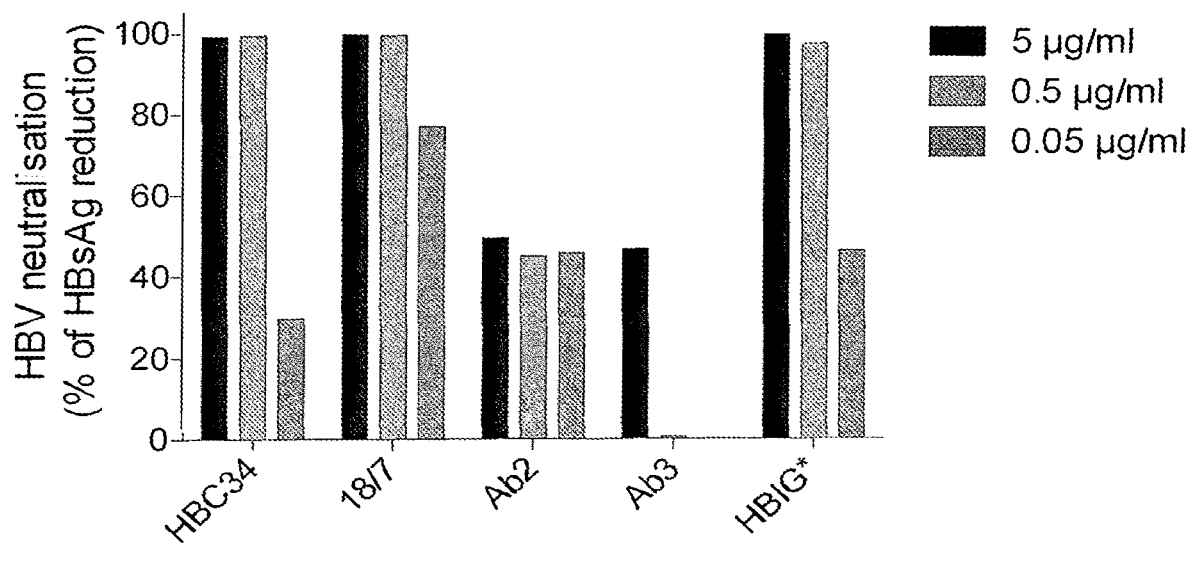
FIG. 2 shows for Example 2 the ability of various anti-HB antibodies, namely HBV immunoglobulins (HBIG), HBC34, and further monoclonal antibodies against PreS1 (18/7) or HBsAg to neutralize HBV infection of HepaRG cell in vitro. Each antibody was tested at three different concentrations, namely 5 µg/ml, 0.5 µg/ml and 0.05 µg/ml, except for HBIG, which was tested at 5000 µg/ml, 500 µg/ml and 50 µg/ml.
Figure 3:
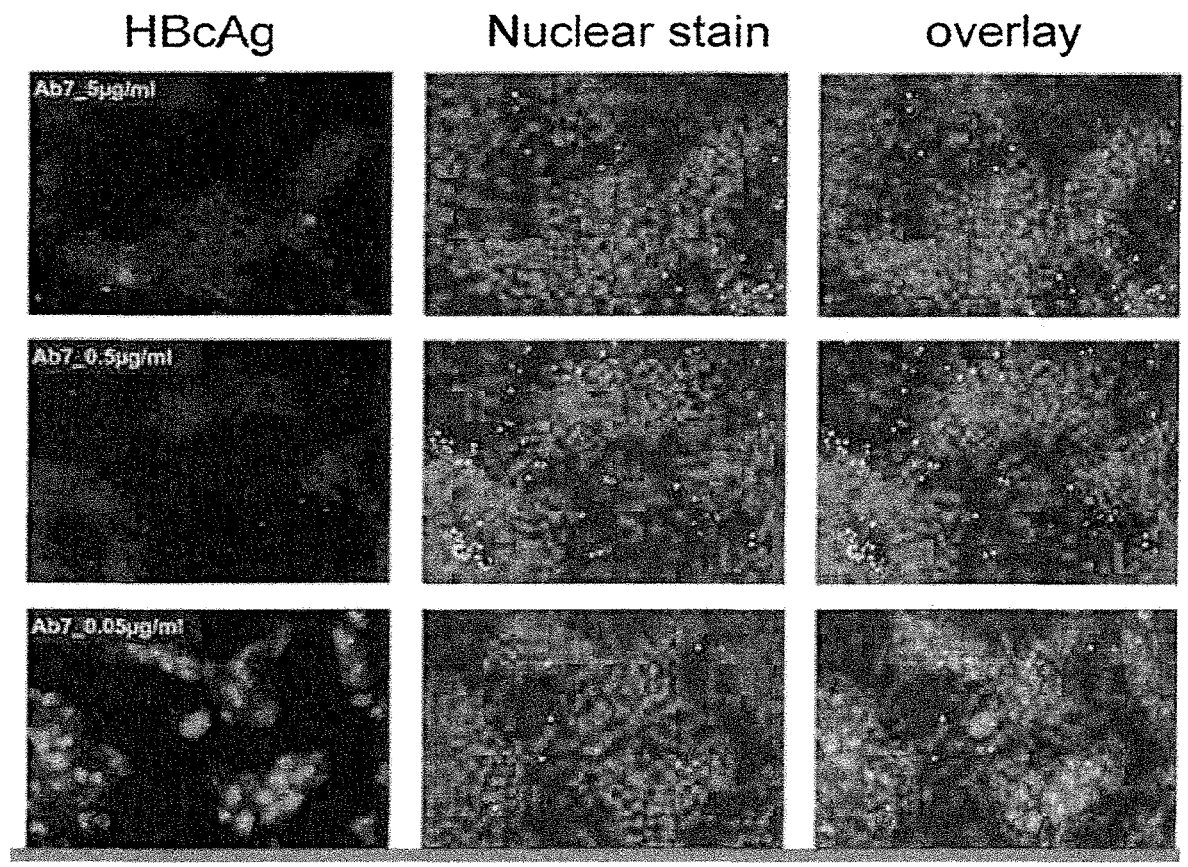
FIG. 3 shows for Example 2 the staining of HBcAg in HepaRG cells infected in the presence of three different concentrations (5 µg/ml, 0.5 µg/ml or 0.05 µg/ml) of HBC34 monoclonal antibody and, as a reference, the nuclear staining.

As shown in FIGS. 2 and 3, HBC34 neutralized completely HBV infection when tested at 5 and 0.5 µg/ml, whereas comparative human monoclonal anti-HB antibodies Ab2 and Ab3, which are also binding to HBsAg, did not result in complete neutralization. This indicates that not all antibodies binding to HBsAg are able to neutralize HBV infection (e.g. Ab2 and Ab3). Of note, HBIG neutralized HBV infection only when tested at 5000 and 500 µg/ml, i.e. with a 1000 fold lower potency as compared to HBC34. 18/7 is a murine monoclonal antibody against the pre-S1 region of HBsAg.

Figure 4:
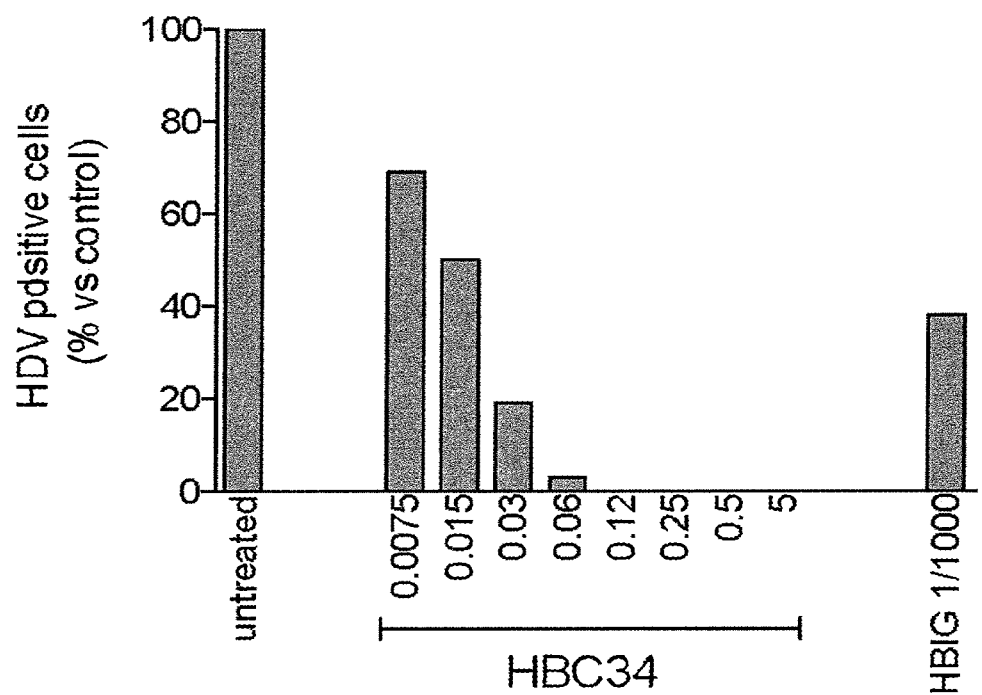
FIG. 4 shows for Example 2 the neutralization activity of different concentrations of HBC34 on infectious HDV. At a concentration of 0.12 µg/ml HBC34 no HDV-positive cells were detectable, indicating potent neutralization of HDV. HBIG, in contrast, did not neutralize HDV (tested in 1:1000 dilution, i.e. 50 µg/ml).

The second object of Example 2 was to determine the neutralizing activity of HBC34 against HDV on differentiated HepaRg cells. Sera from HDV carriers were used as HDV infection inoculum. Delta antigen immunofluorescence staining was used as a readout. As shown in FIG. 4, HBC34 completely blocked HDV infection when tested at 0.12 µg/ml. As a comparison, HBIG were also tested and were ineffective (tested at 1/1000, i.e. 50 µg/ml).

Figure 6:
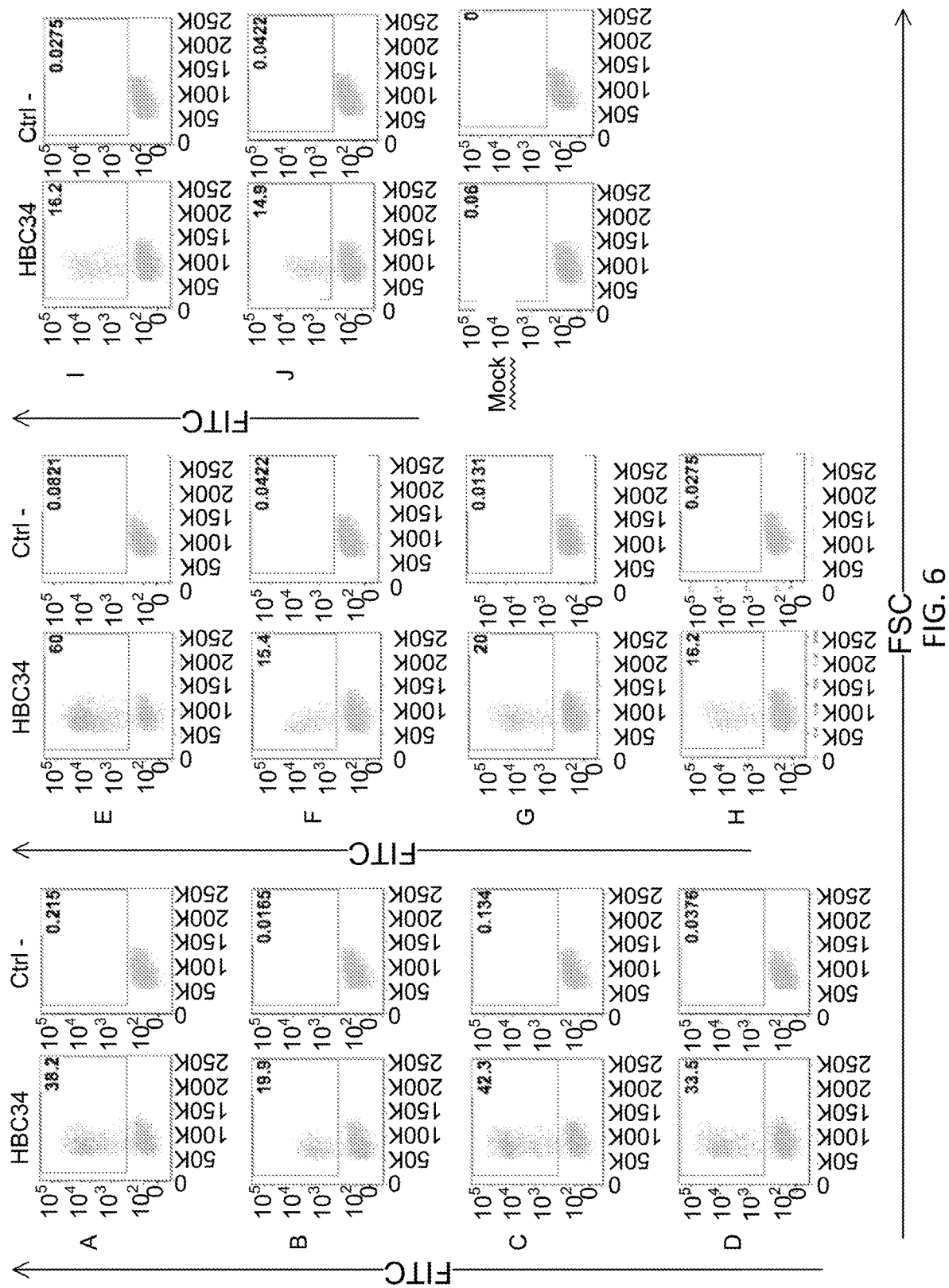
FIG. 6 shows for Example 3 the binding, as determined by cytofluorimetric analysis, of the human monoclonal antibody HBC34 and a control antibody (both at 5 µg/ml) to permeabilized Hep2 cells transiently transfected with plasmids expressing the different HBsAg genotypes A, B, C, D, E, F, G, H, I and J as indicated in the Figure.

Example 3: Antibody HBC34 Recognizes all 10 HBV Genotypes A, B, C, D, E, F, G, H, I, and J HBC34 was tested for its ability to recognize the 10 HBV genotypes A, B, C, D, E, F, G, H, I, and J (as shown in FIG. 5) by flow cytometry analysis. In particular, human epithelial cells (Hep2 cells) were transfected with plasmids expressing each of the HBsAg of the 10 HBV genotypes A, B, C, D, E, F, G, H, I, and J (as shown in FIG. 5). Human monoclonal antibody HBC34 (5 µg/ml) and a control antibody (5 µg/ml) were used for staining of transiently transfected permeabilized cells. Two days after transfection, Hep2 cells were collected, fixed and permeabilized with saponin for immunostaining with HBC34 or a control Ab. Binding of antibodies to transfected cells was analysed using a Becton Dickinson FACSCanto2 (BD Biosciences) with FlowJo software (TreeStar). As shown in FIG. 6 HBC34 recognized all 10 HBV HBsAg genotypes with similar patterns of staining.

Example 4: Antibody HBC34 Recognizes all Functional HBsAg Mutants

Figure 7:
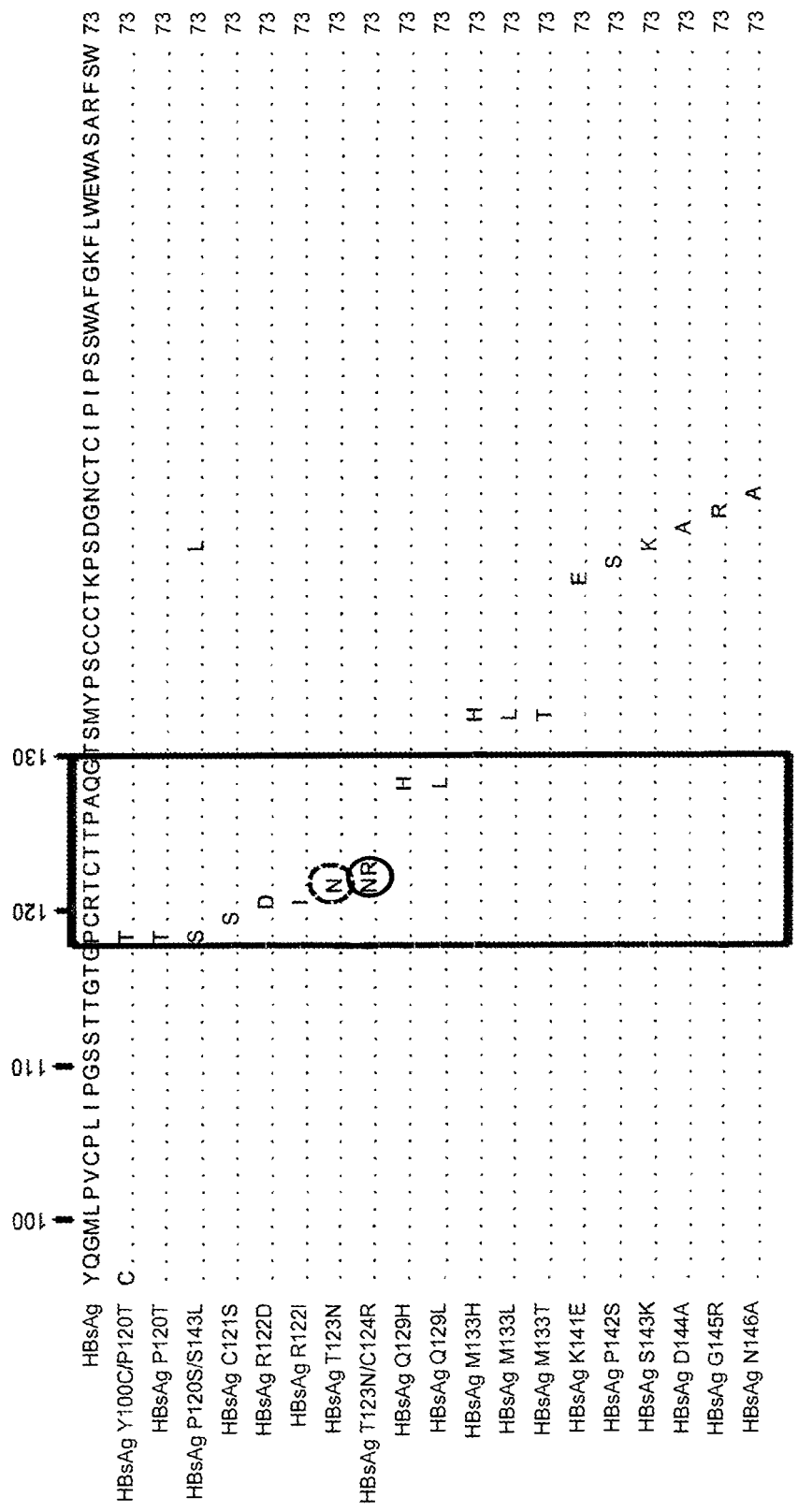
FIG. 7 shows for Example 4 the amino acid sequences of the antigenic loop of the 19 HBsAg mutants tested. Circled are the residues of the HBsAg mutants that were weakly (dotted circle) or not bound by HBC34 antibody.

HBC34 was tested for its ability to bind to the 19 different HBsAg genotype D mutants (based on HBsAg Genotype D, Genbank accession no. FJ899792, as shown in FIG. 7) HBsAg Y100C/P120T, HBsAg P120T, HBsAg P120T/S143L, HBsAg C121S, HBsAg R122D, HBsAg R122I, HBsAg T123N, HBsAg T123N/C124R, HBsAg Q129H, HBsAg Q129L, HBsAg M133H, HBsAg M133L, HBsAg M133T, HBsAg K141E, HBsAg P142S, HBsAg S143K, HBsAg D144A, HBsAg G145R and HBsAg N146A (see SEQ ID NO's 16-33 for the amino acid sequences of the antigenic loop regions of those mutants) by flow cytometry analysis. In particular, human epithelial cells (Hep2 cells) were transfected with plasmids expressing the different HBsAg mutants and analyzed as in Example 3. 5 µg/ml of human monoclonal antibody HBC34 and two other HBsAg-specific antibodies (Ab5 and Ab6) were used for testing the binding of HBC34 to the transfected Hep2 cells.

Figure 8A:
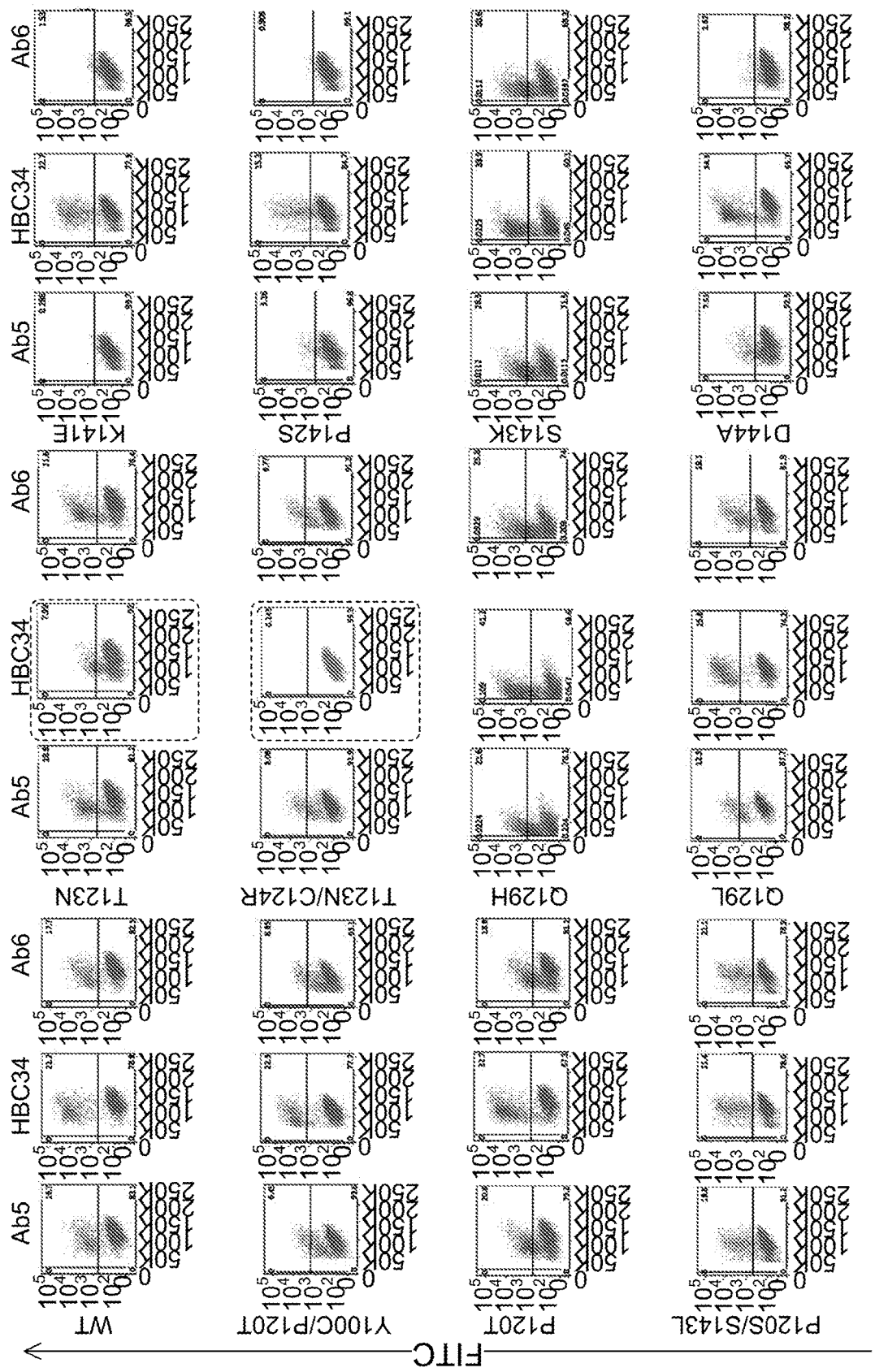
FIGS. 8A and 8B show for Example 4 the binding of the human monoclonal antibody HBC34 and two other HBsAg-specific antibodies (Ab5 and Ab6) all tested at 5 µg/ml on Hep2 cells transfected with plasmids expressing the different HBsAg genotype D mutants as indicated in the Figure ("WT": HBsAg Genotype D, Genbank accession no. FJ899792).
Figure 8B:
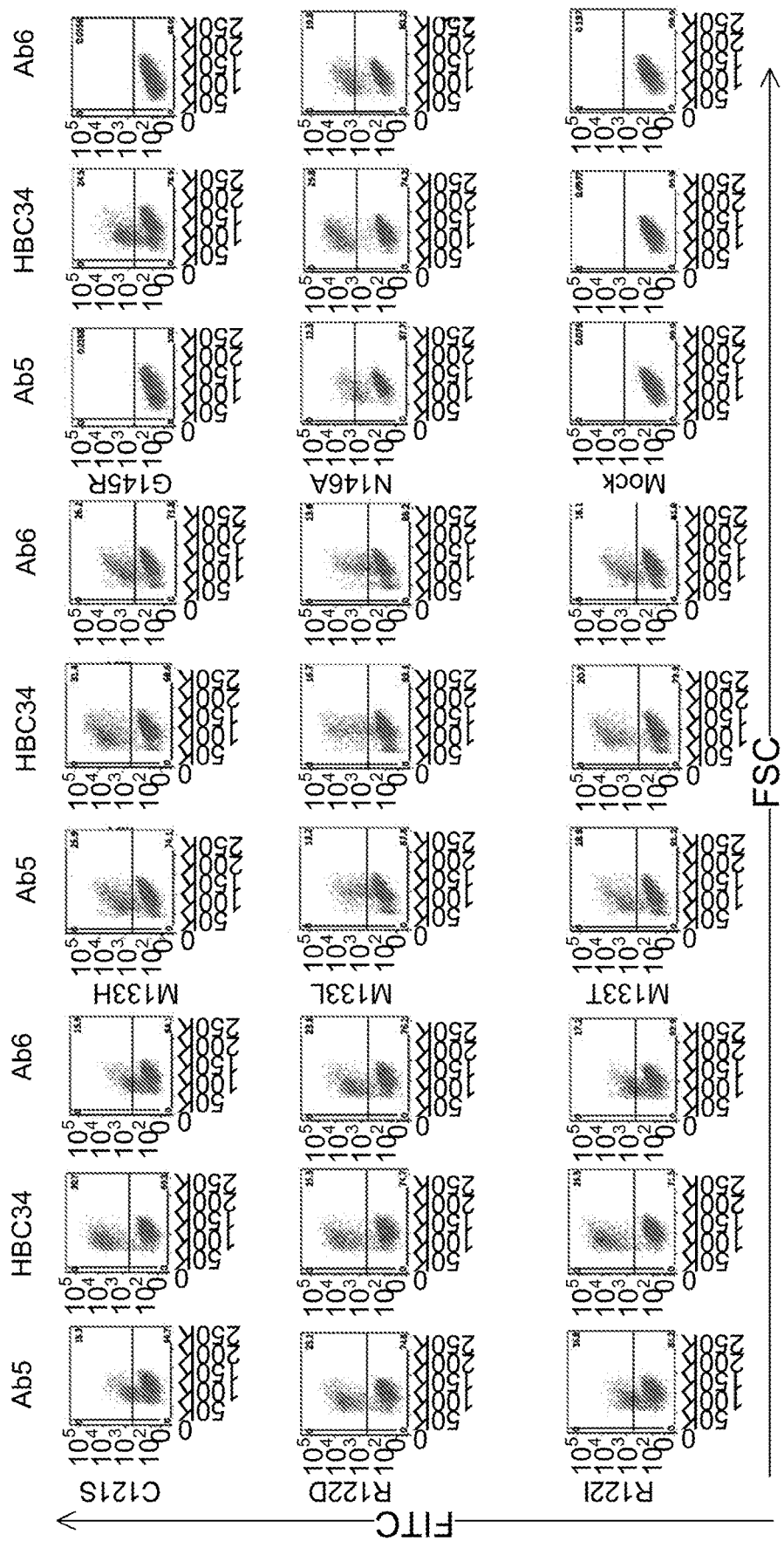

As shown in FIGS. 8A-8B, HBC34 was found to bind to 18 of the 19 HBsAg mutants. HBC34 binding, but not Ab5 and Ab6 binding, was completely abolished only in the mutant HBsAg T123N/C124R, i.e. when residues 123 and 124 were both mutated. Of note, the mutation of these two residues (i.e. T123 and C124) into alanine was shown to be associated with a loss of HBV infectivity, which is most likely due to the loss of the disulphide bridge formed by C124 that could result in a conformational change in the antigenic loop (Salisse J. and Sureau C., 2009, *Journal of Virology* 83: 9321-9328). Thus, human monoclonal antibody HBC34 binds to 18 HBsAg mutants.

Example 5: Antibody HBC34 Binds to a Conserved Conformational Epitope in the Antigenic Loop The epitope recognized by HBC34 was identified by using a library of 650 linear and looped peptides ("CLIPS Discontinuous Epitope Mapping" technology from Pepscan, Lelystad, The Netherlands) designed to cover the entire antigenic loop region of the HBsAg. The linear and CLIPS peptides are synthesized based on standard Fmoc-chemistry. The looped peptides are synthesized on chemical scaffolds in order to reconstruct conformational epitopes, using the Chemically Linked Peptides on Scaffolds, CLIPS, technology as described in Timmerman et al., 2007, Journal of Molecular Recognition 20: 283-99. For example the single looped peptides are synthesized containing two cysteines and the size of the loop is varied by introducing the cysteine residues at variable spacing. If other cysteines besides the newly introduced cysteines are present, they are replaced by alanine. The side-chains of the multiple cysteines in the peptides are coupled to CLIPS templates by reacting onto credit-card format polypropylene PEPSCAN cards (455 peptide formats/card) with a 0.5 mM solution of CLIPS template such as 1,3-bis (bromomethyl)benzene in ammonium bicarbonate. The binding of antibody to each peptide is tested in a PEPSCAN-based ELISA. The 455-well credit card format polypropylene cards containing the covalently linked peptides are incubated with the test antibody (at 1 µg/ml) in blocking solution. After washing the peroxidase substrate 2,2'-azino-di-3-ehylbenzthiazoline sulfonate (ABTS) and 2 µl of 3% $H_2O_2$ are added. After one hour, the color development is measured with a charge coupled device (CCD)-camera and an image processing system. The raw data are optical values and range from 0 to 3000 (a log scale similar to 1 to 3 of a standard 96-well plate ELISA reader).

Figure 9:
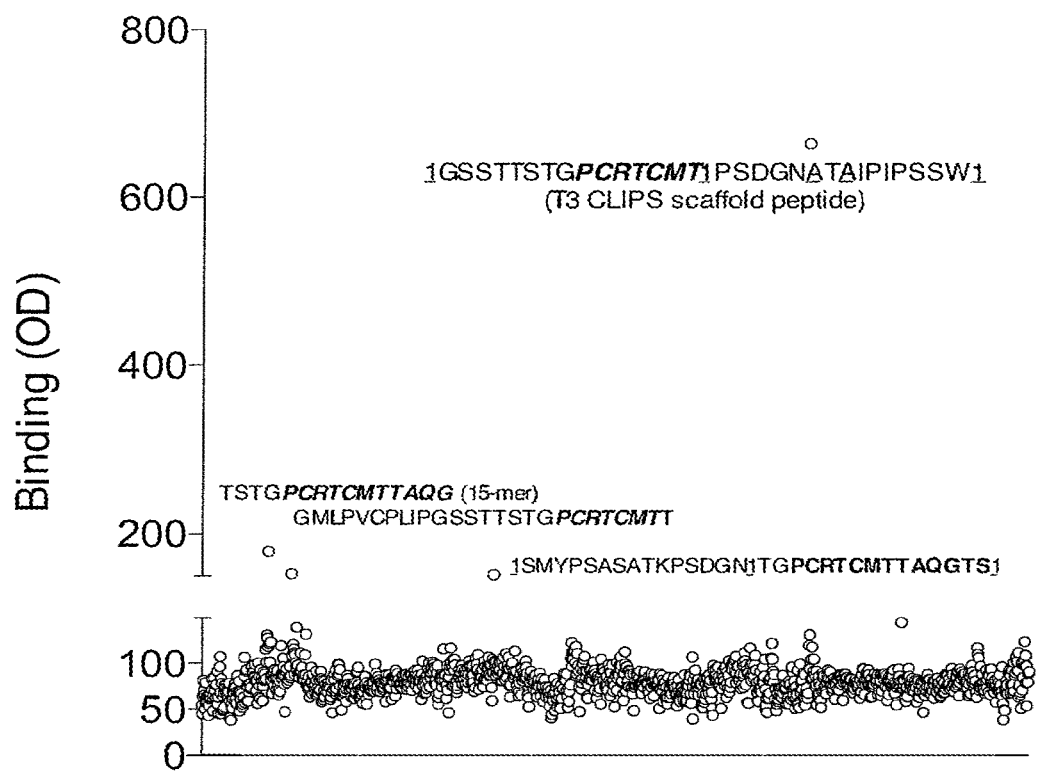
FIG. 9 shows for Example 5 the binding of HBC34 to a library of 650 linear and looped peptides as determined using the Pepscan technology as well as the sequences of the four peptides bound by HBC34. Residues indicate as 1 are cysteines that were introduced to allow the chemical linking to scaffolds in order to reconstruct conformational epitopes. If other cysteines besides the newly introduced cysteines are present, they are replaced by alanine (underlined alanine residues).

As shown in FIG. 9, HBC34 was found to recognize a double looped peptide having an amino acid sequence according to SEQ ID NO 52:

XGSSTTSTGPCRTCMTXPSDGNATAIPIPSSWX wherein the residues coded as X were substituted with Cysteines and the underlined residues were substituted from C to A (SEQ ID NO 52).

Three additional peptides were recognized with a lower signal:

(a) a linear 15-mer peptide having an amino acid sequence according to SEQ ID NO 53:

```
                                (SEQ ID NO 53)
         TSTGPCRTCMTTAQG,
```

(b) another linear peptide having an amino acid sequence according to SEQ ID NO 54:

```
                                (SEQ ID NO 54)
    GMLPVCPLIPGSSTTSTGPCRTCMTT,
``` and (c) a double looped peptide having an amino acid sequence according to SEQ ID NO 55:

XSMYPSASATKPSDGNXTGPCRTCMTTAQGTSX wherein the residues coded as X were substituted with Cysteines and the underlined residues were substituted from C to A (SEQ ID NO 55).

This analysis indicated that the core epitope of HBC34 is formed by a conformational epitope formed by an amino acid sequence according to SEQ ID NO: 56:

```
PCRTCMTTAQG
(SEQ ID NO 56; amino acids 120   130 of the
S domain of HBsAg (HBV D J02203).
```

Figure 10:
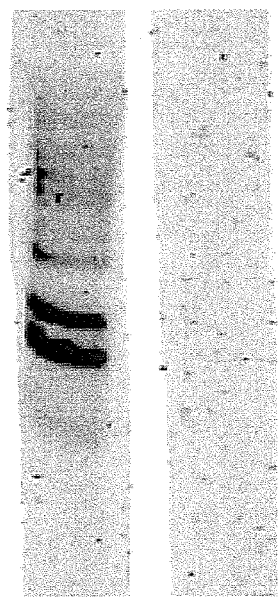
FIG. 10 shows for Example 5 a western blot staining by Ab4 and HBC34 on HBV viral particles under reducing conditions. Ab4 is a comparative antibody, which is also reactive against the antigenic loop.

Moreover, as shown in FIG. 10 the human monoclonal antibody HBC34 does not react at all in a western blot on HBV viral particles under reducing conditions.

These results confirm that the epitope of HBsAg, to which HBC34 binds to, is a conformational epitope.

These results are consistent with what observed in Example 4 where HBC34 binding was lost in the presence of the T123N/C124R mutations.

Figure 11:
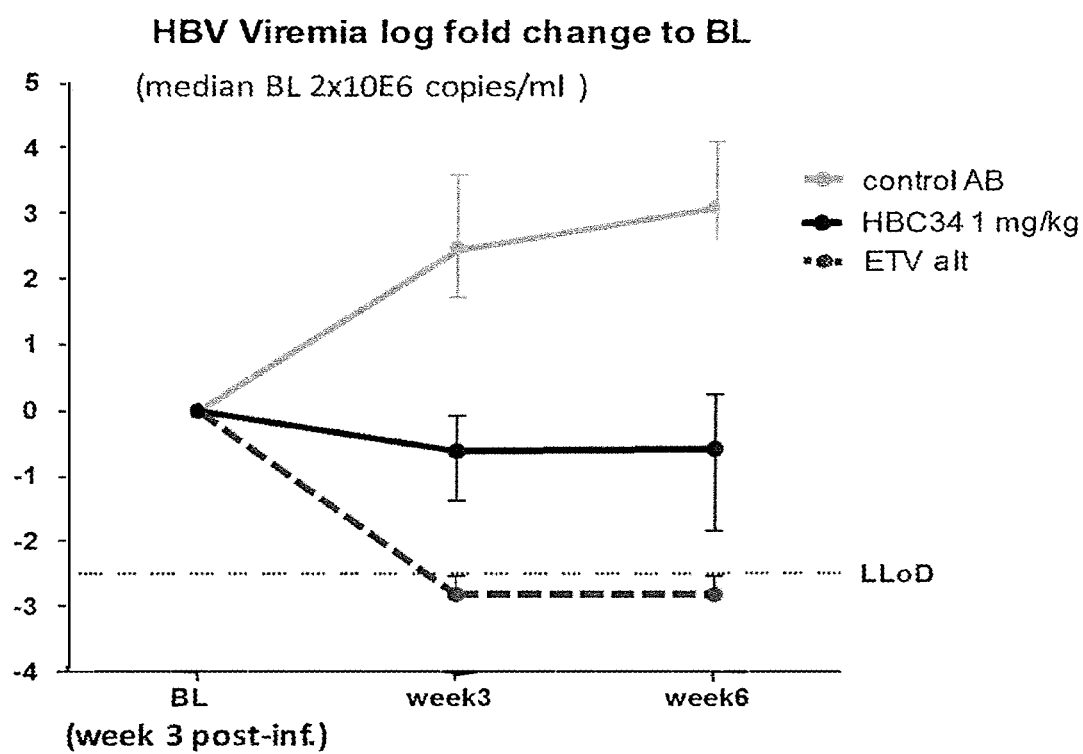
FIG. 11 shows for Example 6 the levels of HBV viremia in humanized uPA/SCID mice inoculated with $5 \times 10^7$ copies of HBV genome equivalents (genotype D), which received from three weeks post-infection treatment with either HBC34 (at 1 mg/kg administered i.p. twice per week), a control antibody (control AB) or entecavir (ETV; administered orally at 1 µg/ml) for 6 weeks. In the spreading phase of HBV infection (weeks 3 to week 6 p.i. (post infection)) viremia increased >2 log in the group which received the control antibody, while HBV titers decreased in mice treated with HBC34 or entecavir.

The region of HBsAg, which comprises the conformational epitope, to which HBC34 binds to, is polymorphic in the different HBV genotypes. In the following generic sequence of the epitope region of HBsAg the residues mutated in the different genotypes are indicated with an X:

(SEQ ID NO: 57)

$PCX_1TCX_2X_3X_4AQG$, wherein $X_1$ is preferably R or K, $X_2$ is preferably M or T, $X_3$ is preferably T or I, and $X_4$ is preferably T, P or L.

Moreover, an additional comparison of the above sequence to the 18 HBsAg mutants, to which the human monoclonal antibody HBC34 binds to, indicates that HBC34 binds to an epitope formed by an amino acid sequence according to SEQ ID NO: 2:

$X_1$ $X_2$ $X_3$ TC $X_4$ $X_5$ $X_6$A $X_7$G wherein $X_1$ is P, T or S, $X_2$ is C or S, $X_3$ is R, K, D or I, -continued $X_4$ is M or T, $X_5$ is T, A or I, $X_6$ is T, P or L, and $X_7$ is Q, H or L.

Example 6: Administration of HBC34 Starting 3 Weeks Post HBV Infection Prevents Viral Spreading in Humanized uPA Mice The object of Example 6 was to investigate whether human monoclonal antibody HBC34 is able to prevent spreading of HBV. In other words, it was the aim to investigate the capacity of the entry inhibitor HBC34 antibody to inhibit infection of the human hepatocytes in vivo by treating mice after the initial infection establishment. To this end, naïve uPA/SCID mice repopulated with primary human hepatocytes (see Petersen et al. Nature Biotechnology, 2008, 26:335-341) were used. These mice were engrafted with cryopreserved human hepatocytes by intrasplenic injection. Eight weeks later successful repopulation of human hepatocytes in the host liver was determined measuring human serum albumin, which is exclusively expressed by transplanted human hepatocytes. Mice with appropriate human albumin levels were inoculated i.p. with $5\times10^7$ copies of HBV genome equivalents (genotype D, HBeAg positive) to permit viral entry. Three weeks after infection, the treatment protocol started whereby mice received either HBC34 treatment (at 1 mg/kg administered i.p. twice per week), a control antibody or entecavir (ETV; administered orally at 1 μg/ml in water, Baraclude Solution, Bristol-Myers Squibb) for 6 weeks. Liver specimens removed at sacrifice were snap-frozen in liquid nitrogen for immunofluorescence analysis.

HBV DNA was extracted from serum samples using the QiAmp MinElute Virus spin kit (Qiagen, Hilden, Germany). HBV-specific primers and hybridization probes were used to determine HBV DNA viremia and cccDNA loads quantitatively as described previously (Volz T et al., Gastroenterology 2007; 133: 843-852). DNA and RNA were extracted from liver specimens using the Master Pure DNA purification kit (Epicentre, Biozym, Germany) and RNeasy RNA purification kit (Qiagen, Hilden, Germany). Intrahepatic HBV DNA values were normalized for cellular DNA contents using the beta-globin gene kit (Roche DNA control Kit; Roche Diagnostics). Levels of rcDNA were estimated by subtracting cccDNA amounts from total HBV DNA. Viral RNAs and genomic RNAs were reverse transcribed using oligo-dT primers and the Transcriptor Kit (Roche Applied Science) and quantified by using primers specific for total viral RNAs. HBV RNA levels were normalized to human specific GAPDH RNA. HBsAg quantification from blood samples was performed using the Abbott Architect platform (quant. HBsAg kit, Abbott, Ireland, Diagnostic Division), as recommended by the manufacturer. Cryostat sections of chimeric mouse livers were immunostained using humans pecific cytokeratin-18 monoclonal (Dako, Glostrup, Denmark) to stain human hepatocytes. For the detection of the HBV core antigen (HBcAg), the polyclonal rabbit anti-HBcAg was used. Specific signals were visualized by employing the Alexa-labeled secondary antibodies (Invitrogen, Darmstadt, Germany) or TSA-Fluorescein (HBcAg) System (Perkin Elmer, Jugesheim, Germany), while nuclear staining was obtained with Hoechst 33342 (Invitrogen). Stained sections were analyzed by fluorescence microscope.

The median baseline level of HBV DNA at the beginning of the treatment was $2\times10^6$ DNA copies/ml. In the spreading phase of HBV infection (weeks 3 to week 6 p.i. (post infection)) viremia increased >2 log in the group which received the control antibody, while HBV titers decreased in mice treated with HBC34 or entecavir (FIG. 11).

Figure 12:
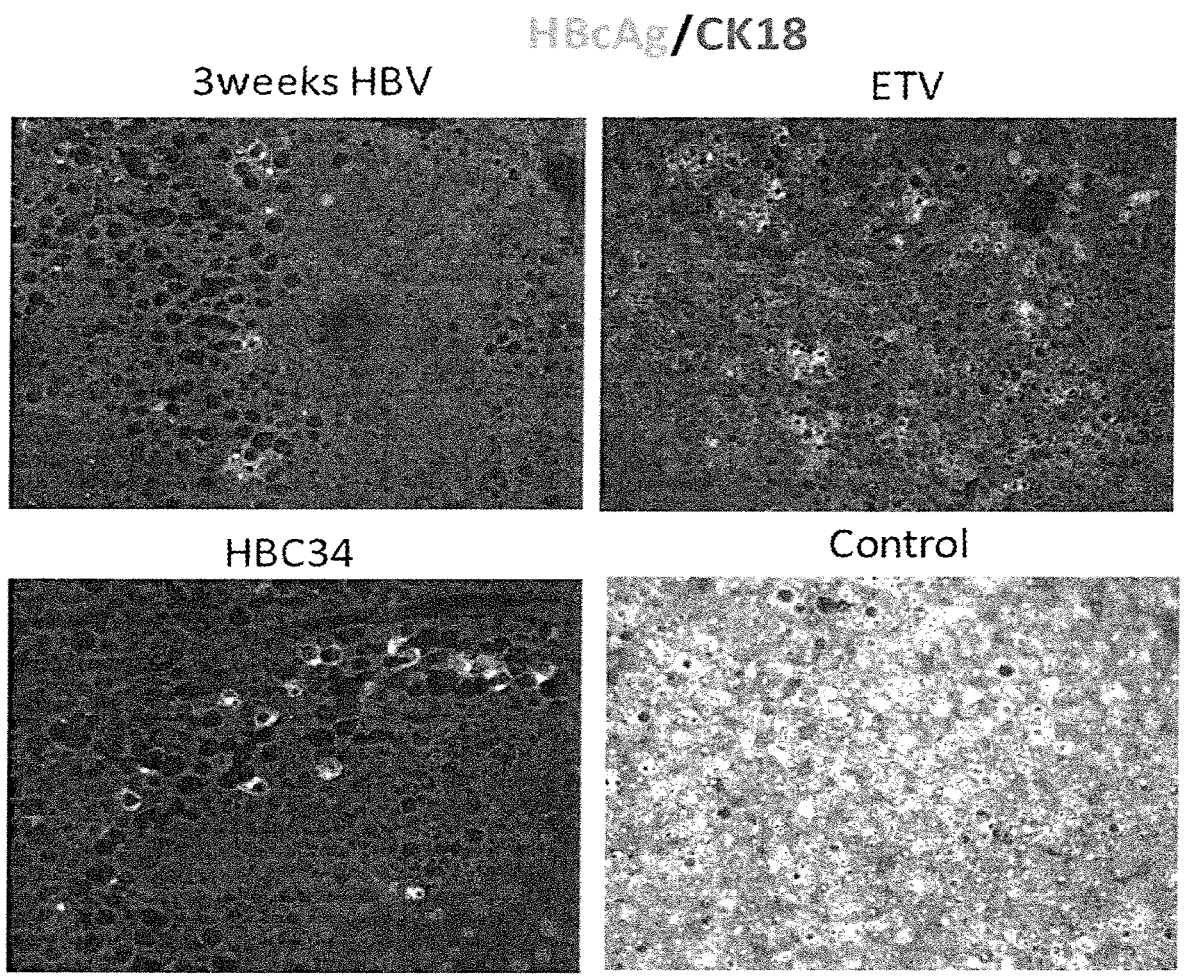
FIG. 12 shows for Example 6 staining of hepatocytes for the presence of HBsAg (intrahepatical analysis) in mice of Example 6 at the end of the experiment (week 9). Nearly all hepatocytes stained HBsAg positive in mice which received the control antibody, while spreading was efficiently blocked by both, treatment with entecavir and treatment with HBC34 (ca. 1-5% HBsAg-positive cells).

Mice were also analyzed intrahepatically at the end of the experiment (i.e. week 9) by staining hepatocytes for the presence of HBcAg. Nearly all hepatocytes stained HBcAg positive in mice which received the control antibody, while spreading was efficiently blocked by both, treatment with entecavir and treatment with HBC34 (ca. 1-5% HBcAg-positive cells). These results indicate that HBC34 can efficiently block viral spreading during the ramp-up phase of HBV infection (FIG. 12).

Figure 13:
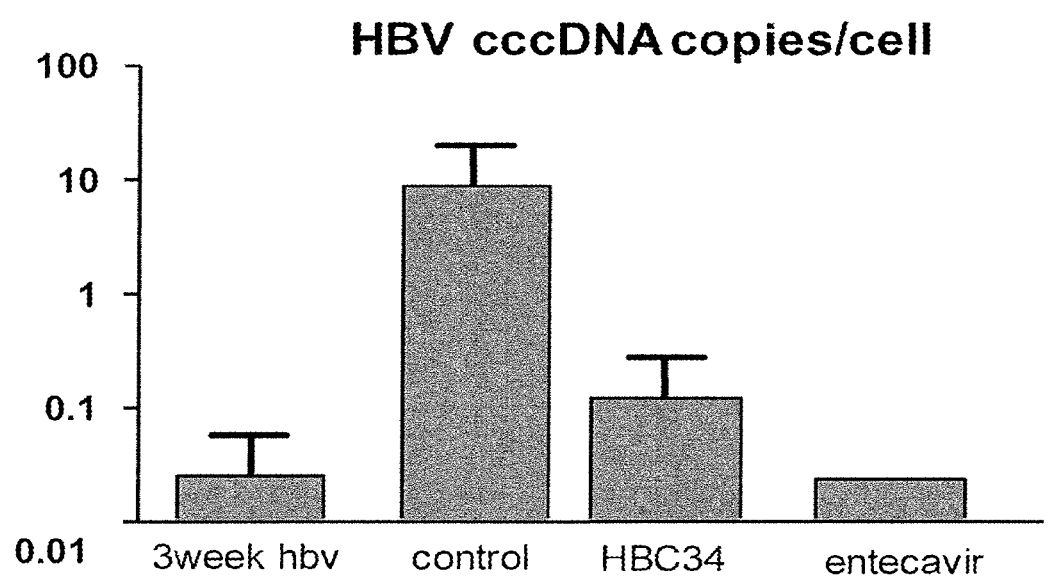
FIG. 13 shows for Example 6 cccDNA measurements, which did not differ significantly between mice that were sacrificed 3 weeks post HBV infection ("3 week hbv"; i.e. no treatment) and mice that were treated from week 3 to week 9 post-infection with HBC34 or entecavir. In contrast, the estimated amount of cccDNA/cell increased up to 2 logs in the group receiving the control antibody when sacrificed 9 weeks post-infection.

In line with the histological and serological data, cccDNA measurements showed that intrahepatic cccDNA loads did not differ significantly between mice that were sacrificed 3 weeks post HBV infection and mice that were treated from week 3 to week 9 post-infection. In comparison, the estimated amount of cccDNA/cell increased up to 2 logs in the control group sacrificed 9 weeks post-infection, suggesting that newly formed rcDNAs could not be efficiently converted into cccDNA in treated mice (FIG. 13). The same tendency was also found by measuring other intrahepatic viral parameters, such as the levels of relaxed circular DNA (rcDNA) and HBV RNA transcripts.

Figure 14:
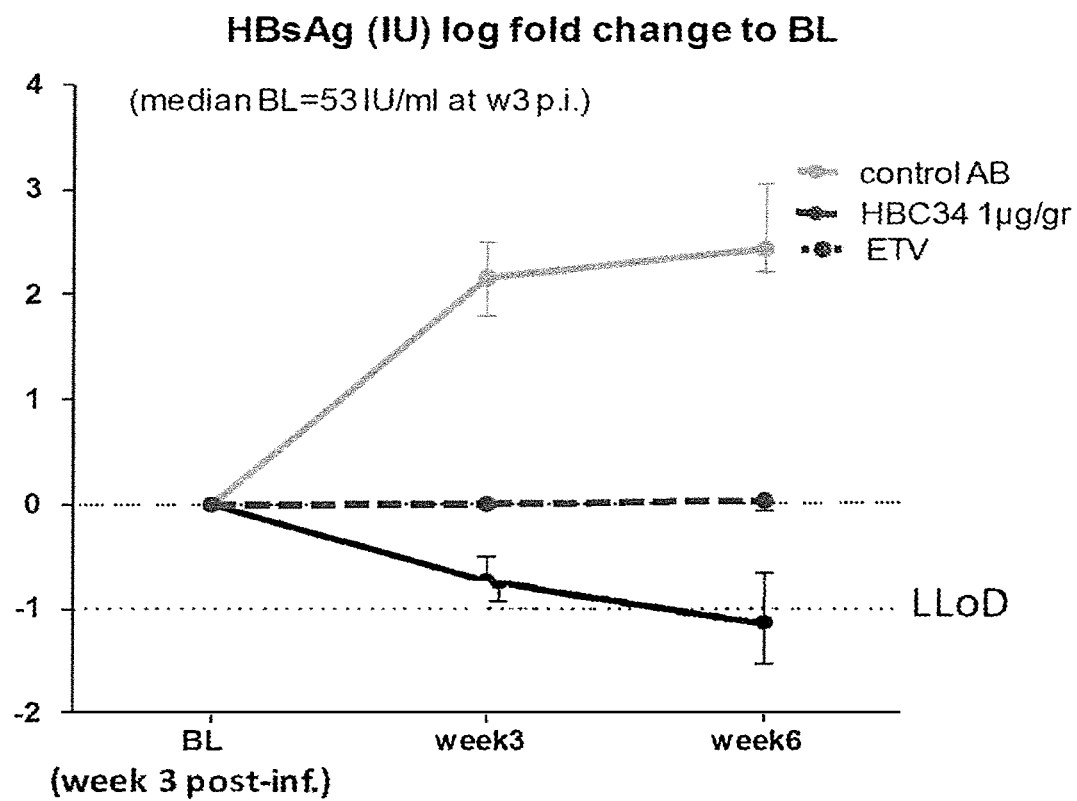
FIG. 14 shows for Example 6 levels of circulating HBsAg at baseline (BL), week 3 of treatment (week 6 post-infection) and week 6 of treatment (week 9 post-infection). Levels of circulating HBsAg decreased >1 log (and below the limit of detection) in mice receiving HBC34, but not in mice treated with entecavir, while HBsAg levels increased >2 logs (reaching levels of 5000-10000 IU/ml) in the control group.

Moreover, levels of blood circulating HBsAg were measured at baseline (BL), week 3 of treatment (week 6 post-infection) and week 6 of treatment (week 9 post-infection). It is of note that the levels of circulating HBsAg decreased >1 log (and below the limit of detection) in mice receiving HBC34, but not in mice treated with entecavir, while HBsAg levels increased >2 logs (reaching levels of 5000-10000 IU/ml) in the control group (FIG. 14). The measurement of HBsAg was not influenced by the presence of the HBC34 antibody as determined in a spike-in experiment where the addition of HBC34 antibody to HBsAg positive mouse sera did not alter the expected measurement using the Abbott Architect diagnostic immunoassay.

These results indicate that HBC34 can block HBV viral spread and promote the clearance of HBsAg.

Example 7: Administration of HBC34 in Chronically HBV Infected Humanized uPA Mice Promoted HBV and HBsAg Clearance To mimic the hepatitis B chronic setting, naïve humanized uPA/SCID mice were infected with HBV and after 12 weeks post infection, a median level of HBV DNA of $2 \times 10^9$ copies/ml and a level of HBsAg of 10000 IU/ml was reached. These levels are as high as the levels that are commonly observed in human patients with chronic HBV infection.

Figure 15:
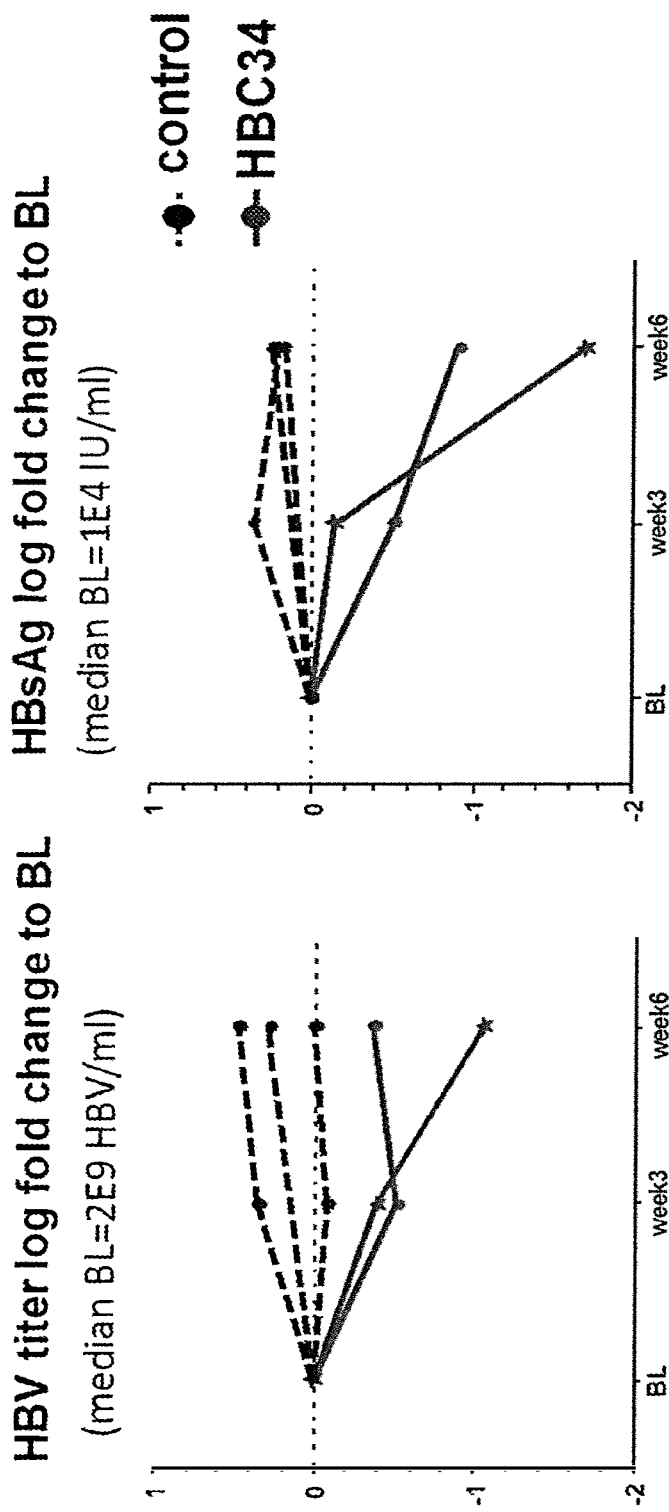
FIG. 15 shows for Example 7 HBV titer (left panel) and levels of circulating HBsAg (right panel) in a chronic hepatitis B setting at baseline (BL), week 3 of treatment (week 15 post-infection, "week 3") and week 6 of treatment (week 18 post-infection, "week 6"). HBV titer and levels of circulating HBsAg were decreased in mice receiving HBC34 at week 3 and week 6 of treatment. Individual curves represent individual animals. Control antibody: dotted lines, HBC34: continuous lines.

Thereafter, the mice were treated starting from week 12 post-infection either with HBC34 or with a control antibody for 6 weeks (1 mg/kg i.p. twice per week). As shown in FIG. 15 HBV titer and levels of blood circulating HBsAg were decreased in mice receiving HBC34 for 3 weeks (week 15 post-infection) and 6 weeks (week 18 post-infection). Thus, HBC34 promoted a clear reduction of both HBV viremia and HBsAg levels after 6 weeks of treatment. HBeAg and human albumin levels were not altered in HBC34-treated mice, which indicates the absence of liver toxicity.

Example 8: Administration of HBC34 Blocks HDV Infection In Vivo

Naïve humanized uPA/SCID mice were co-infected with a patient-derived serum containing HDV-RNA and HBV-DNA. Five weeks after infection (when HBV titers reached levels between $10^7$ to $10^9$, and HDV RNA reached levels between 103 to $10^6$ copies/ml) mice were treated with HBC34 or a control antibody for 6 weeks (1 mg/kg i.p. twice per week).

HBV DNA viremia was measured as described in Examples 6 and 7. HDV viremia was determined via reverse transcription of viral RNA (extracted from serum samples using the QiAmp MinElute Virus Spin Kit, Qiagen, Venlo, Netherlands) and quantitative RT-PCR using the ABI Fast 1-Step Virus Master (Applied Biosystems, Carlsbad, USA), HDV specific primers and probes on a ABI Viia7 (Applied Biosystems, Carlsbad, USA).

Figure 16:
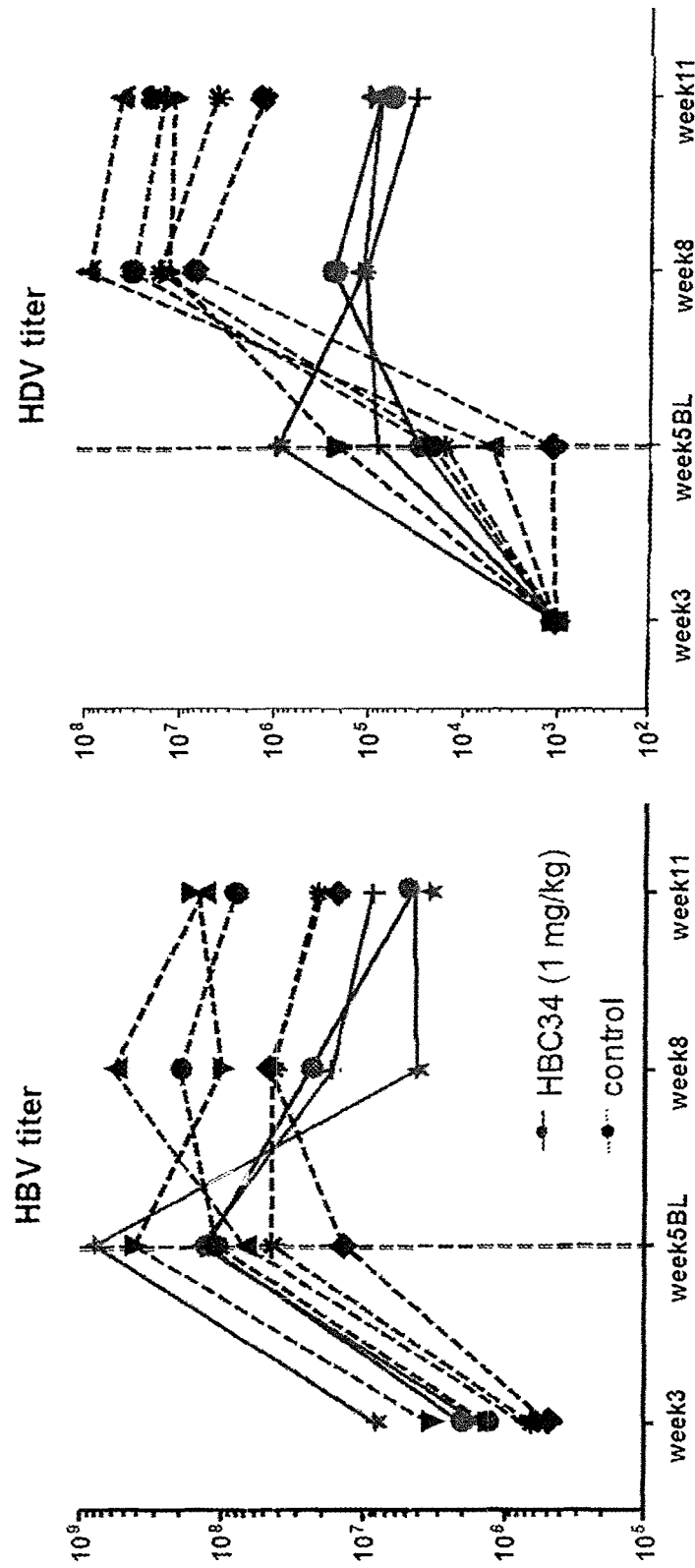
FIG. 16 shows for Example 8 HBV titer (left panel) and HDV titer (right panel) in uPA/SCID mice repopulated with primary human hepatocytes and co-infected with a patient-derived serum containing HDV-RNA and HBV-DNA. Five weeks after infection treatment with HBC34 or a control antibody ("control") was started. HBV titer (left panel) and HDV titer (right panel) are shown at baseline (week 3, week 5BL), at week 3 of treatment (week 8 post-infection—"week 8") and at week 6 of treatment (week 11 post-infection—"week 11"). Individual curves represent individual animals. Control antibody: dotted lines, HBC34: continuous lines.

As shown in FIG. 16, HBC34 efficiently blocked HDV viral spread both 3 weeks and 6 weeks after treatment (weeks 8 and 11, respectively). Similarly to what was observed in HBV chronically infected mice, HBC34 promoted a HBV viral DNA titers reduction of 2 logs (FIG. 13).

Example 9: Fine Epitope Mapping of the HBC34 Discontinuous Epitope

In order to further refine the epitope recognized by HBC34 antibody described in Example 5 a new library of 1520 peptides composed of 16 different sets was generated:

Set 1 (dubbed LIN15): Linear 15-mer peptides derived from the target sequence (SEQ ID NO: 5: QGMLPVCPLIPGSSTTSTGPCRTCMTTAQGT-SMYPSCCCTKPSDGNCTCIP IPSSWAFGKFLWE-WASARFSW; J02203 (D, ayw3)) with an offset of one residue. Native Cys residues are protected by an acet-amidomethyl group (also referred to as "Acm"; denoted as "2" in the respective amino acid sequences).

Set 2 (dubbed LIN22): Linear 22-mer peptides derived from the target sequence (SEQ ID NO: 5: QGMLPVCPLIPGSSTTSTGPCRTCMTTAQGT-SMYPSCCCTKPSDGNCTCIP IPSSWAFGKFLWE-WASARFSW; J02203 (D, ayw3)) with an offset of one residue. Native Cys residues are protected by Acm (denoted "2").

Set 3 (dubbed LIN30): Linear 30-mer peptides derived from the target sequence (SEQ ID NO: 5: QGMLPVCPLIPGSSTTSTGPCRTCMTTAQGT-SMYPSCCCTKPSDGNCTCIP IPSSWAFGKFLWE-WASARFSW; J02203 (D, ayw3)) with an offset of one residue. Native Cys residues are protected by Acm (denoted "2").

Set 4 (dubbed LIN15.AA): Peptides of set 1, but with residues on positions 9 and 10 replaced by Ala. When a native Ala occurred on either position, it was replaced by Gly.

Set 5 (dubbed LIN22.AA): Peptides of set 2, but with residues on positions 12 and 13 replaced by Ala. When a native Ala occurred on either position, it was replaced by Gly.

Set 6 (dubbed LIN30.AA): Peptides of set 3, but with residues on positions 16 and 17 replaced by Ala. When a native Ala occurred on either position, it was replaced by Gly.

Set 7 (dubbed CYS.A): Combinatorial peptides of length 27. On positions 1-11 and 17-27 are linear sequences, which contain pairing Cys residues. These 11-mer sequences joined via "GGSGG" (SEQ ID NO: 79) linker. Cys residues, which do not participate in disulfide bridge formation are protected by Acm (denoted "2").

Set 8 (dubbed as CYS.B): Linear 22-mer sequences, which contain two Cys forming a disulfide bridge. Cys residues, which do not participate in disulfide bridge formation are protected by Acm (denoted "2").

Set 9 (dubbed LOOP12): Constrained peptides of length 12. On positions 2-11 are 10-mer sequences derived from the target sequence of Antigenic Loop of HBV-S-Ag. On positions 1 and 12 are Cys residues, which are joined by mP2 CLIPS. Native Cys residues are protected by Acm (denoted "2").

Set 10 (dubbed as LOOP15): Constrained peptides of length 15. On positions 2-14 are 13-mer sequences derived from the target sequence of Antigenic Loop of HBV-S-Ag. On positions 1 and 15 are Cys residues, which are joined by mP2 CLIPS. Native Cys residues are protected by Acm (denoted "2").

Set 11 (dubbed LOOP21): Constrained peptides of length 21. On positions 2-20 are 19-mer sequences derived from the target sequence of Antigenic Loop of HBV-S-Ag. On positions 1 and 21 are Cys residues, which are joined by mP2 CLIPS. Native Cys residues are protected by Acm (denoted "2").

Set 12 (dubbed LOOP31): Constrained peptides of length 31. On positions 2-30 are 29-mer sequences derived from the target sequence of Antigenic Loop of HBV-S-Ag. On positions 1 and 31 are Cys residues, which are joined by mP2 CLIPS. Native Cys residues are protected by Acm (denoted "2").

Set 13 (dubbed MAT.A): Combinatorial peptides of length 25. On positions 2-12 and 14-24 are 11-mer peptides derived from the target sequence of Antigenic Loop of HBV-S-Ag. On positions 1, 13 and 25 are Cys residues, which are joined by T3 CLIPS. Native Cys residues are protected by Acm (denoted "2").

Set 14 (dubbed MAT.B): Combinatorial peptides of length 28. On positions 2-12 and 14-27 are 11-mer and 14-mer peptides respectively. On positions 1, 13 and 28 are Cys residues, which are joined by T3 CLIPS. Native Cys residues are protected by Acm (denoted "2").

Set 15 (dubbed MAT.C): Combinatorial peptides of length 28. On positions 2-15 and 17-27 are 14-mer and 11-mer peptides respectively. On positions 1, 16 and 28 are Cys residues, which are joined by T3 CLIPS. Native Cys residues are protected by Acm (denoted "2").

Set 16 (dubbed MAT.D): Combinatorial peptides of length 31. On positions 2-15 and 17-30 are 14-mer peptides derived from the target sequence of Antigenic Loop of HBV-S-Ag. On positions 1, 16 and 31 are Cys residues, which are joined by T3 CLIPS. Native Cys residues are protected by Acm (denoted "2").

Figure 17:
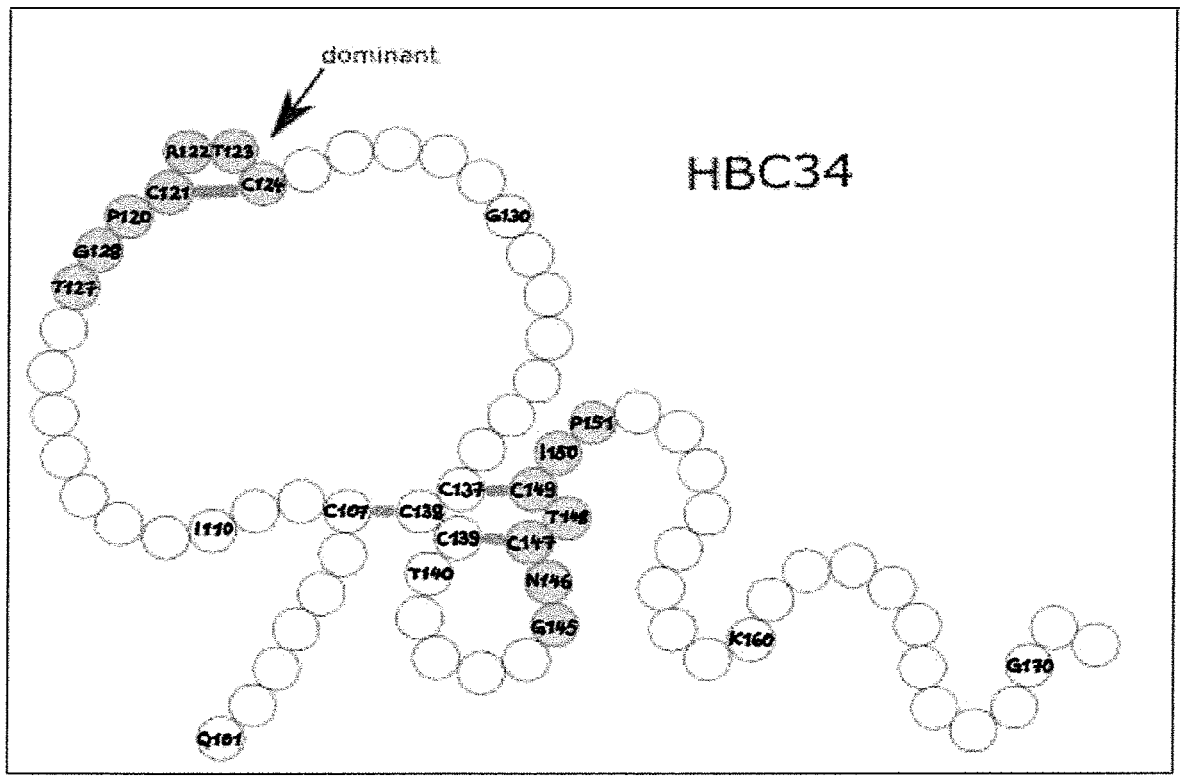
FIG. 17 (part 1) shows for Example 9 a schematics of the antigenic loop of HBV-s-Antigen, the epitope of HBC34 is highlighted in grey. To map the epitope of HBC34 a library of 1520 different peptides was tested as determined using the Pepscan technology.
Figure 17:
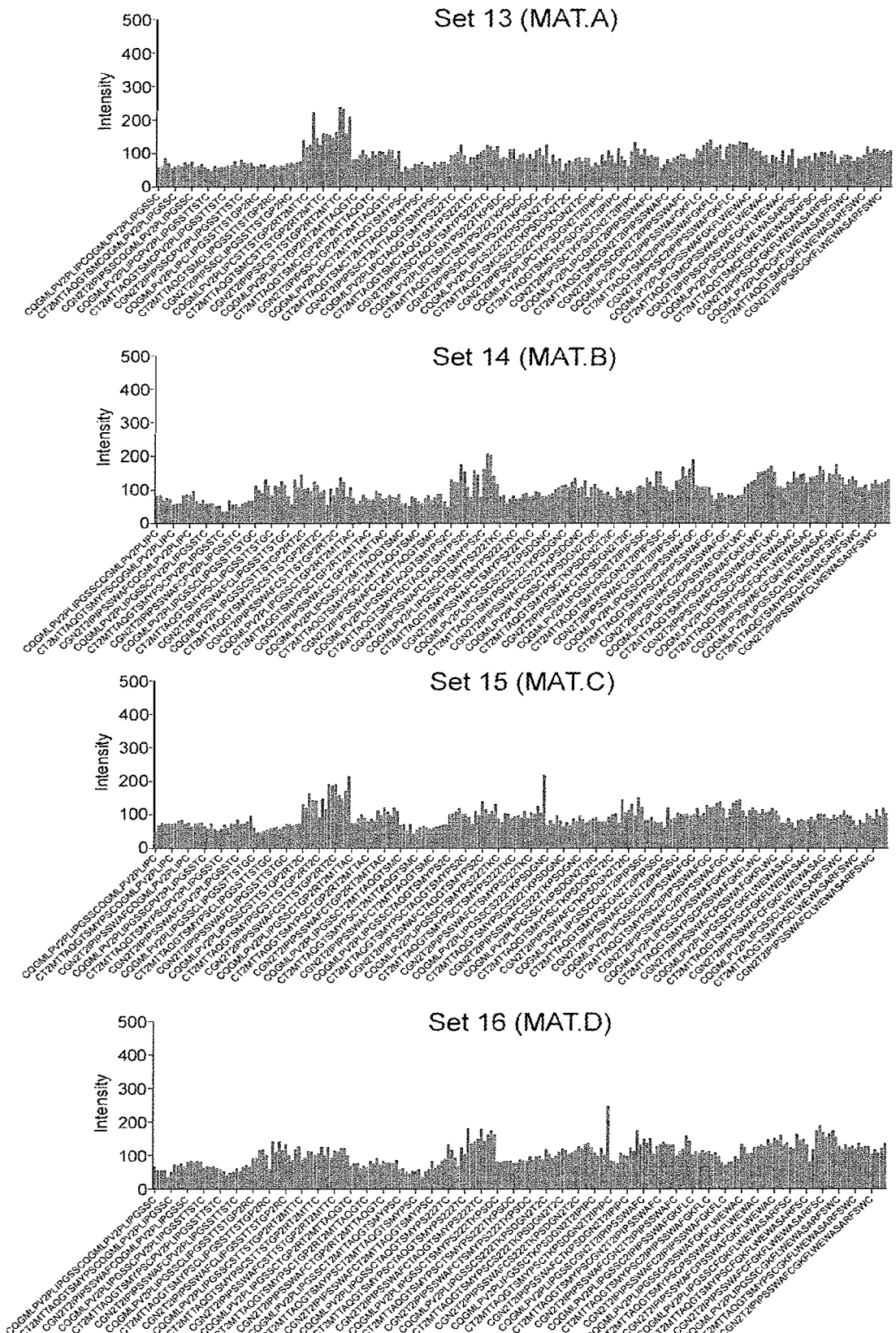
Figure 17:
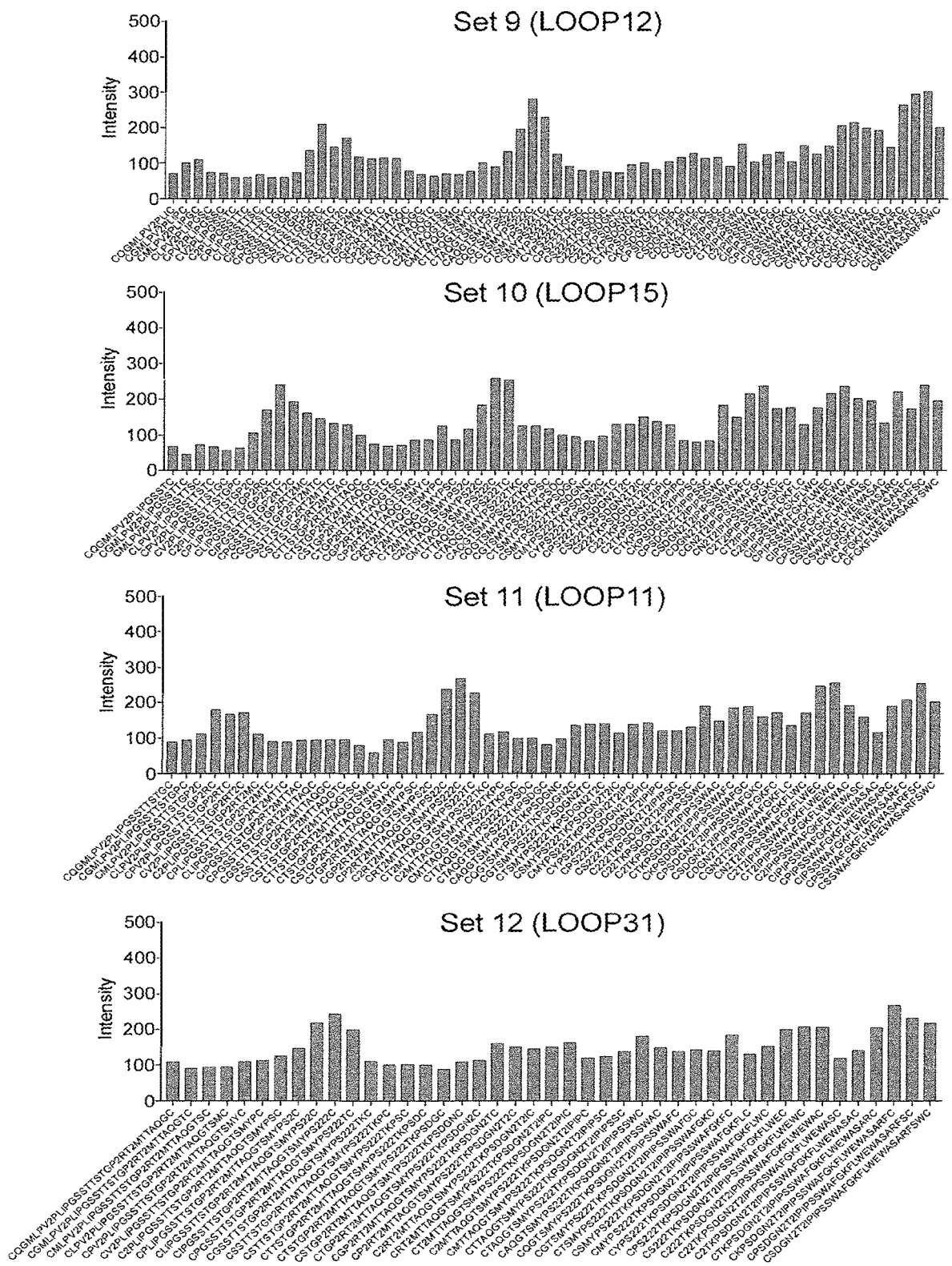
Figure 17:
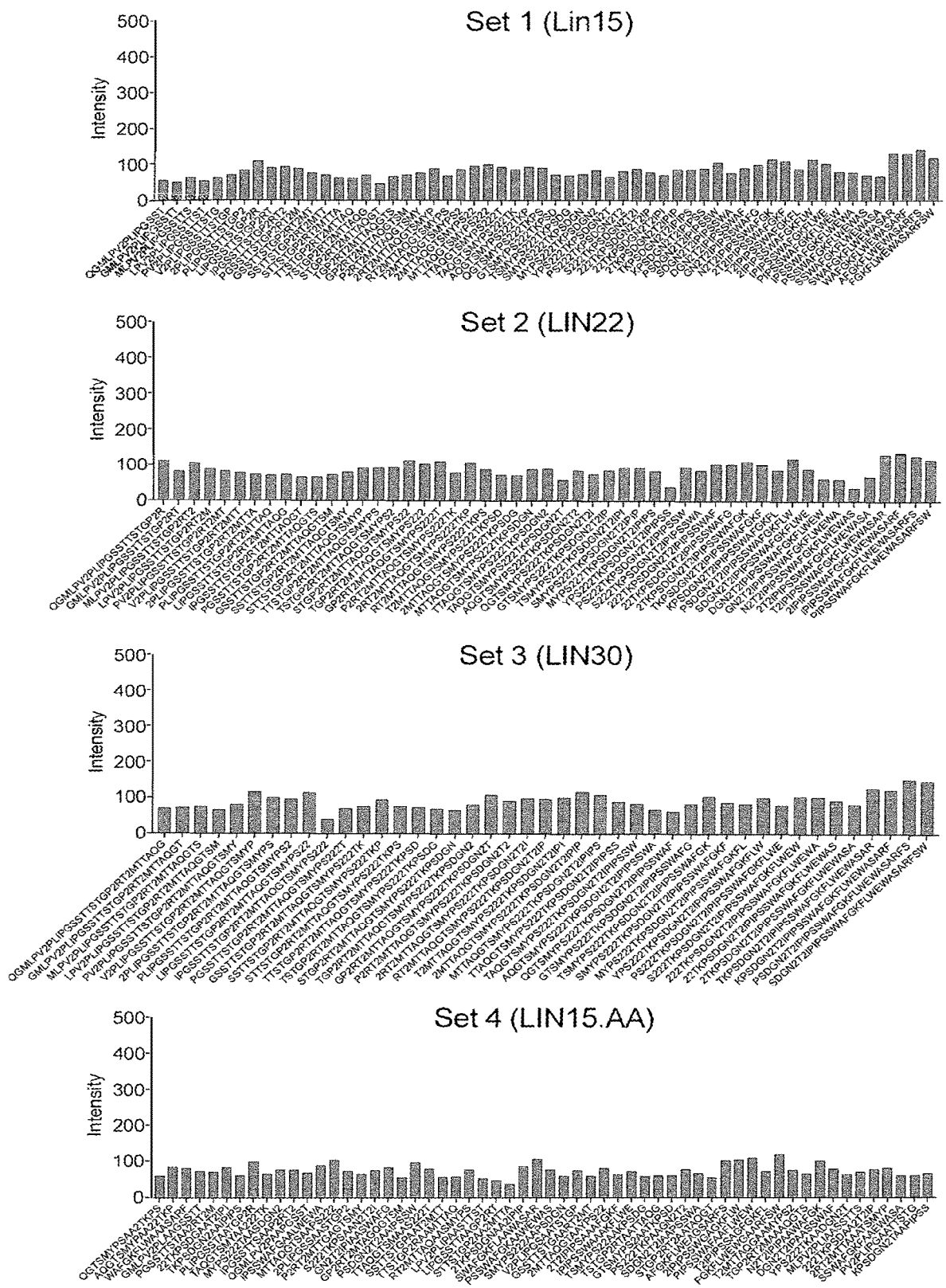
Figure 17:
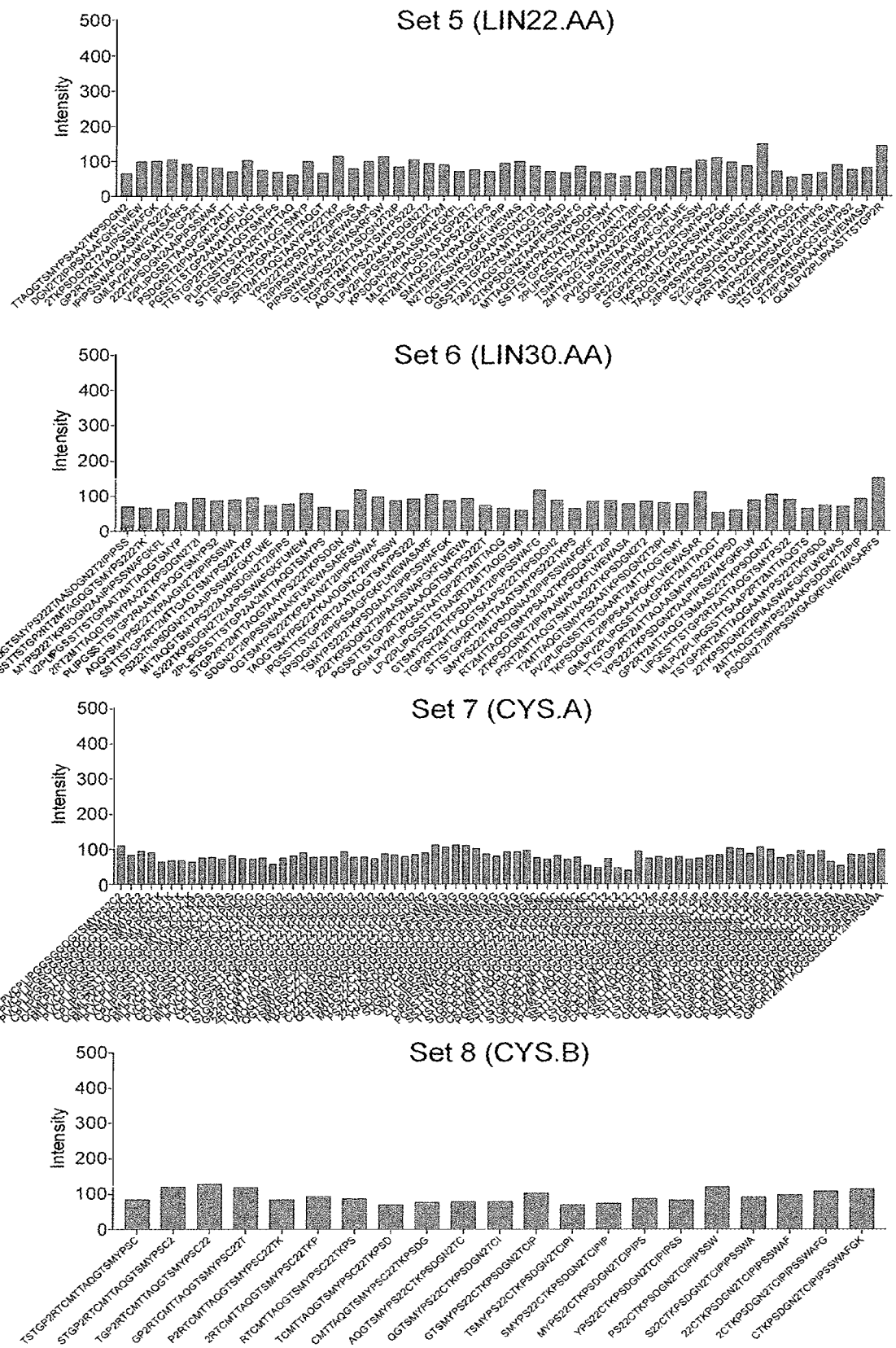

When tested under high stringency conditions antibody HBC34 did not bind any peptide present on the arrays. When tested under low stringency conditions (5 µg/ml in 0.1% Pepscan buffer and preconditioning containing a combination of horse serum and ovalbumin) the antibody bound constrained and combinatorial peptides—binding to peptides from set 14 and set 16 was somewhat lower as compared to set 13 and set 15. No binding was recorded on linear epitope mimics. Data are shown in FIG. 17. These data show that antibody HBC34 recognizes a conformational discontinuous epitope composed of peptide stretches $_{18}TGPCRTC_{24}$ (SEQ ID NO: 80) and $_{45}GNCTCIP_{5i}$ (SEQ ID NO: 81), where peptide stretch $_{18}TGPCRTC_{24}$ (SEQ ID NO: 80) is the dominant part of the epitope (FIG. 17).

To fine map the epitope of antibody HBC34 by means of full substitution analysis based on the results described above, 812 discontinuous or looped T3 CLIPS peptides composed of three different set were synthesized:

Set 1 (dubbed RN1; Discontinuous T3 CLIPS): Epitope mutant series derived from the discontinuous mimic C2IPIPSSWAFGCSTTSTGP2RT2C (SEQ ID NO: 82). For each position of this sequence, a substitution analysis was performed. In other words, for each position of the peptide sequence, variants were made in which the original amino acid at such position was replaced by one of the 13 amino acids selected from the group consisting of alanine (A), glutamic acid (E), phenylalanine (F), glycine (G), histidine (H), lysine (K), leucine (L), proline (P), glutamine (Q), arginine (R), serine (S), valine (V), tyrosine (Y), and " "; where "_" stands for residue deletion. Native Cys residues are protected by Acm (denoted "2").

Set 2 (dubbed RN2; Discontinuous T3 CLIPS): Epitope mutant series derived from the discontinuous mimic CGN2T2IPIPSSWAFCSTTSTGP2RT2C (SEQ ID NO: 83). For each position of this sequence, a substitution analysis was performed in the same manner as for Set 1 (i.e., GN2T residues were not mutated). Native Cys residues are protected by Acm (denoted "2").

Set 3 (dubbed RNs; Loop T3 CLIPS): Epitope mutant series derived from the looped mimic CGGGCSTTSTGP2RT2C_ (SEQ ID NO: 84). For positions 6-16 of this sequence, a substitution analysis was performed in the same manner as for set 1. Native Cys residues are protected by Acm (denoted "2").

HBC34 antibody was tested in the PEPSCAN-based ELISA at 20 µg/ml on the peptide array pre-conditioned with 0.1% SQ (Pepscan buffer containing 0.1% of a combination of horse serum and ovalbumin). The peptide arrays were incubated with HBC34 antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 20 µl/ml of 3 percent $H_2O_2$ were added. After one hour, the color development was measured. The color development was quantified with a charge coupled device (CCD)-camera and an image processing system.

Figure 18:
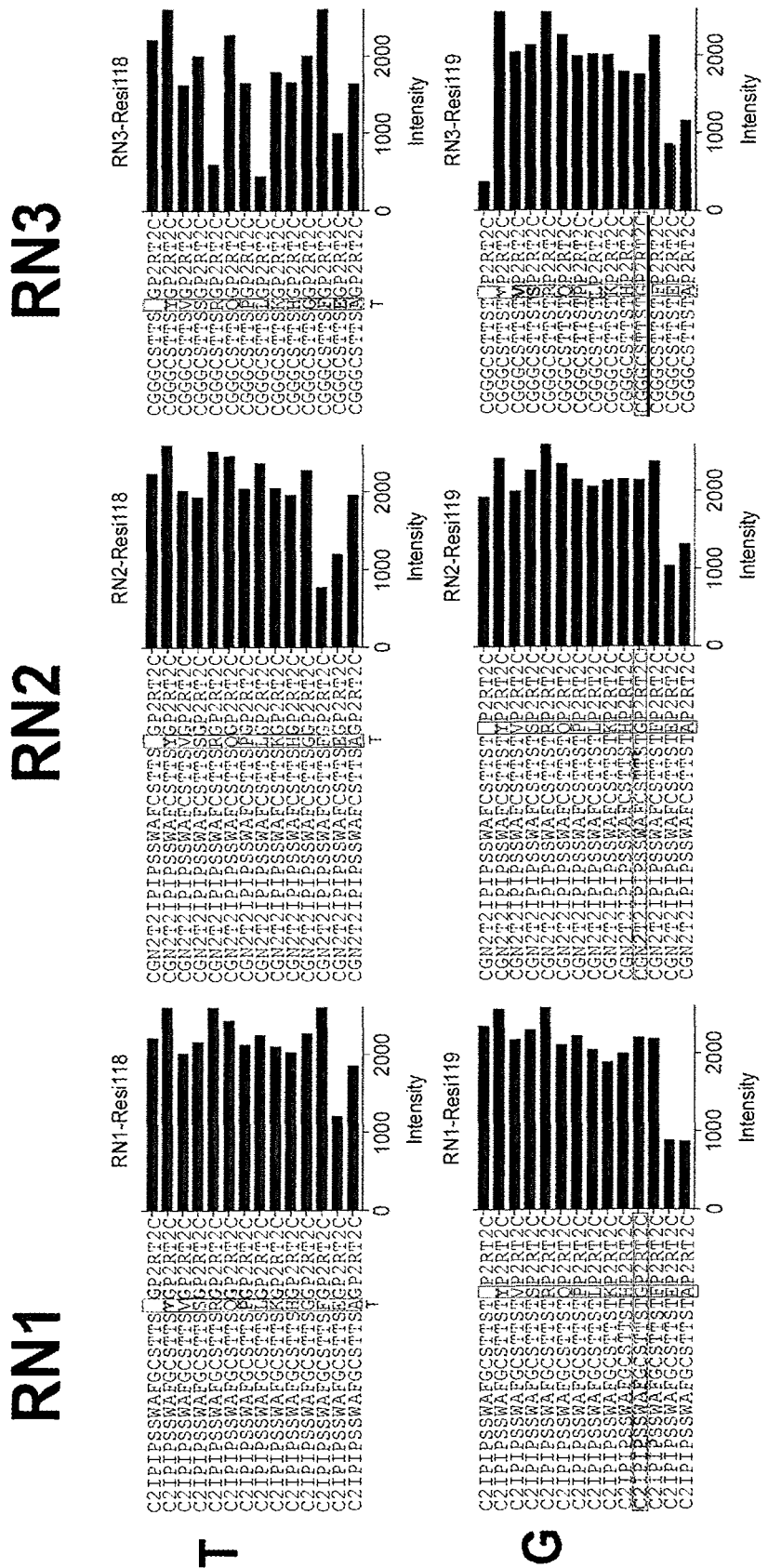
FIG. 18 shows for Example 9 the binding of HBC34 to a peptide library composed of 812 discontinuous or looped T3 CLIPS peptides. In order to fine tune the epitope mapping described in FIG. 17, 3 sets of peptides (dubbed RN1, RN2 and RN3) were generated based on the previous sets (FIG. 17) by means of full substitution analysis.
Figure 18:
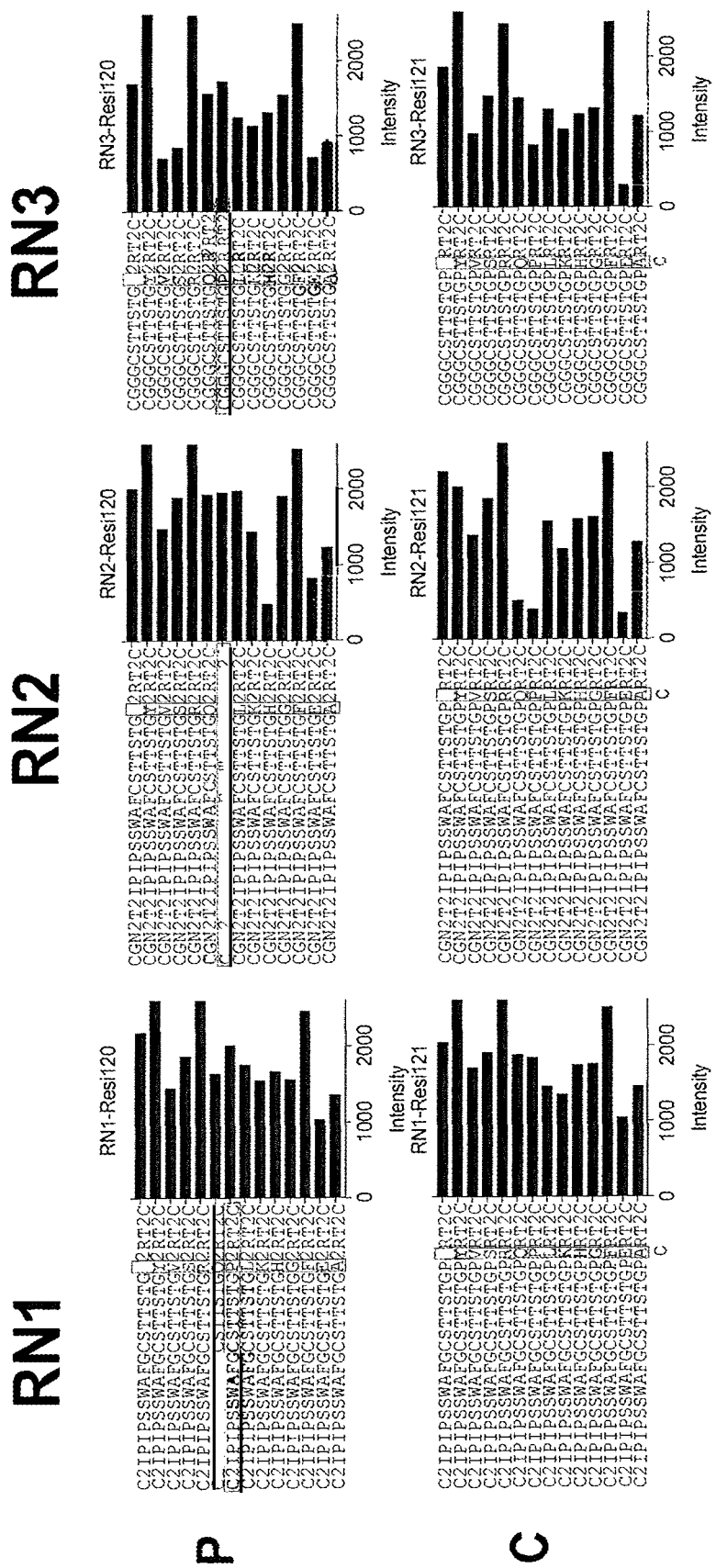
Figure 18:
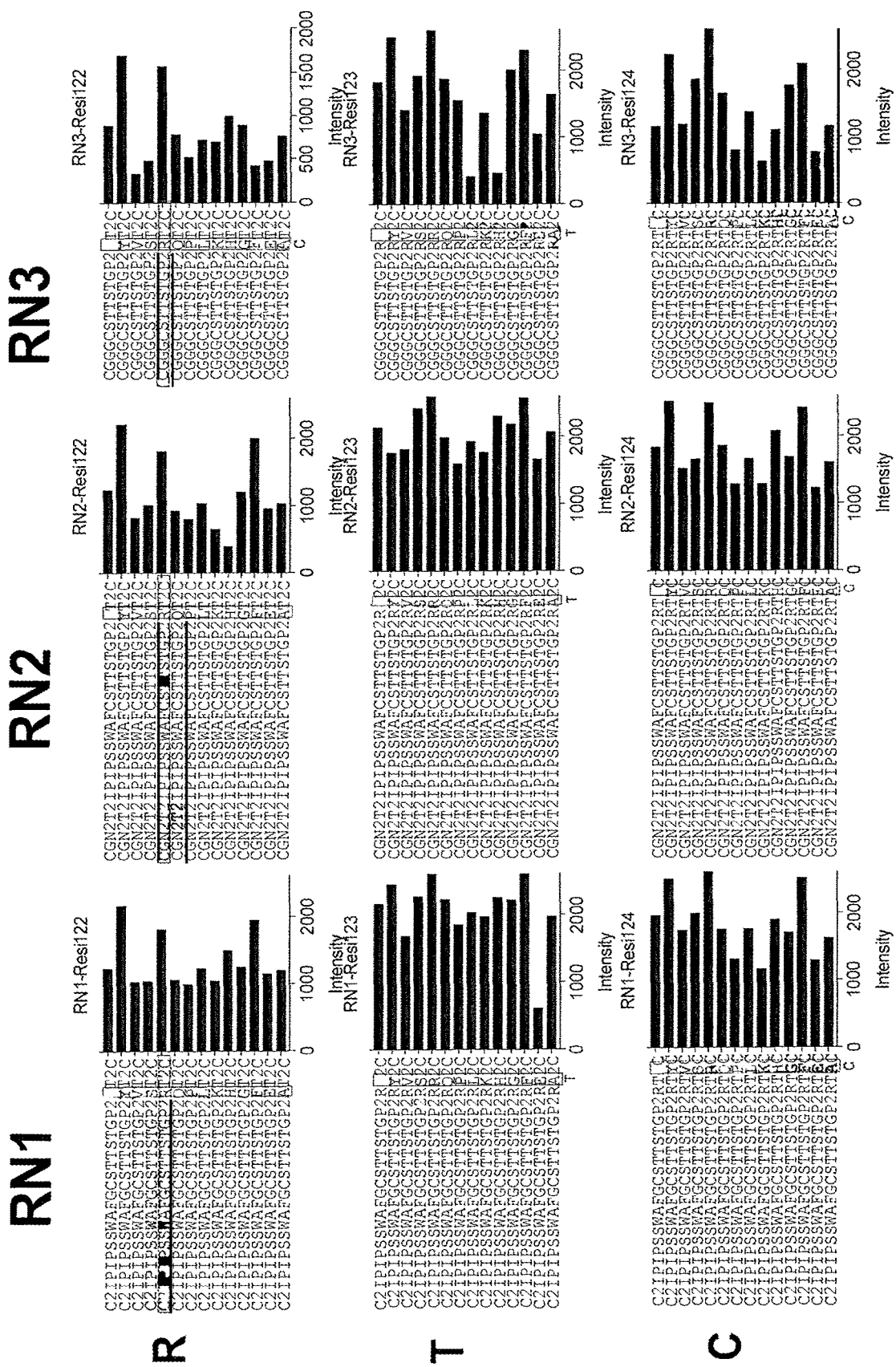
Figure 18:
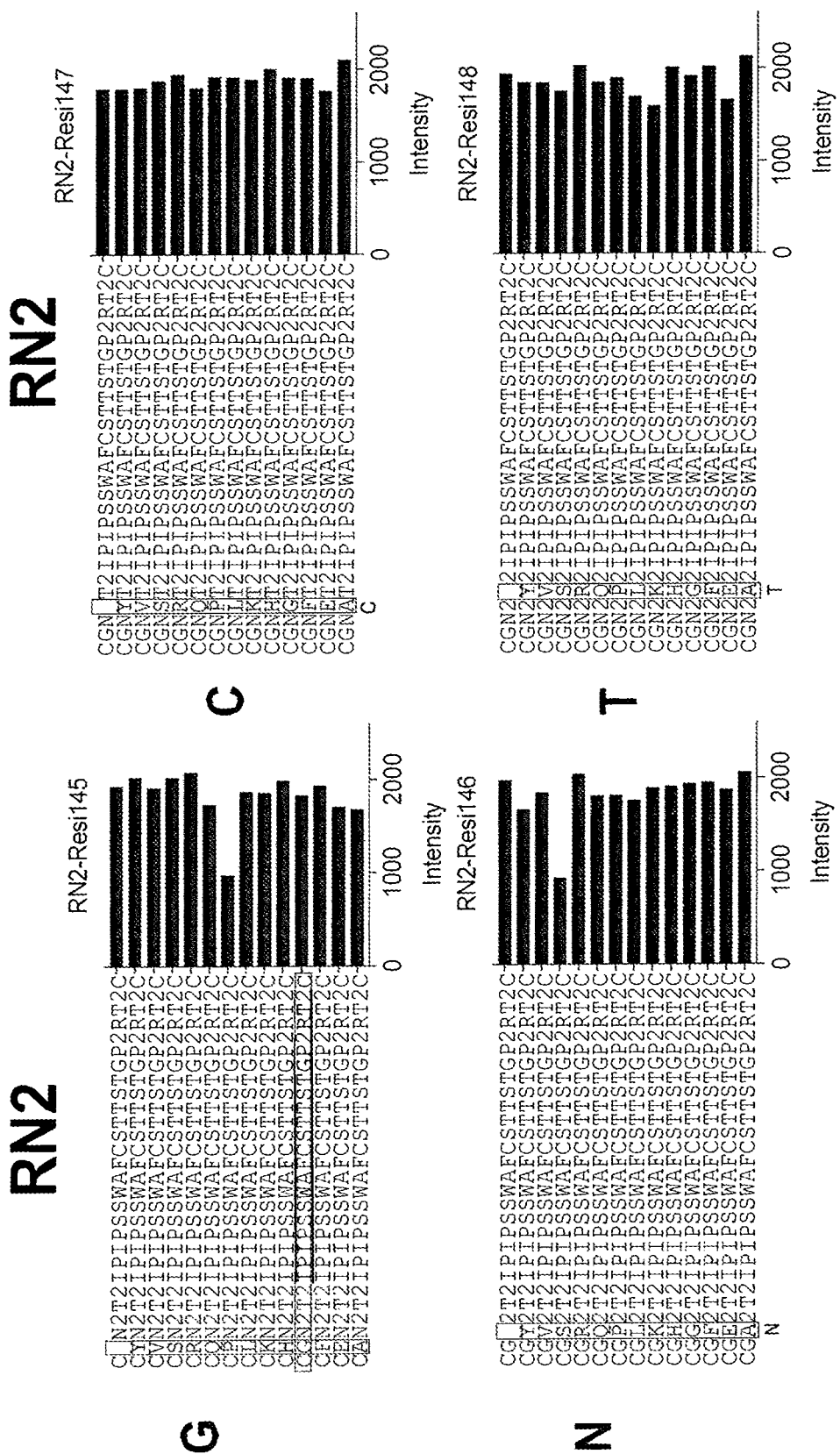
Figure 18:
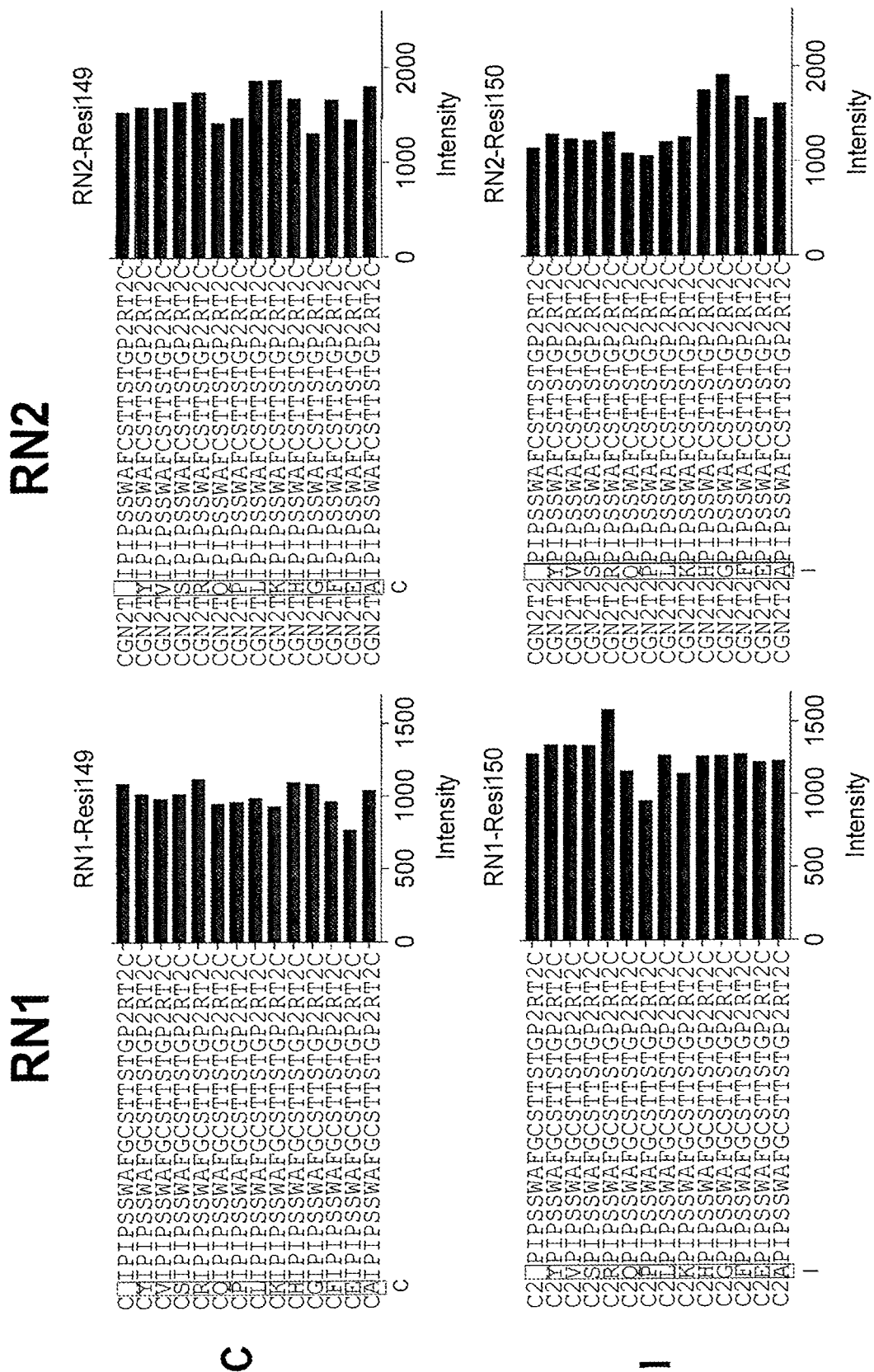
Figure 18:
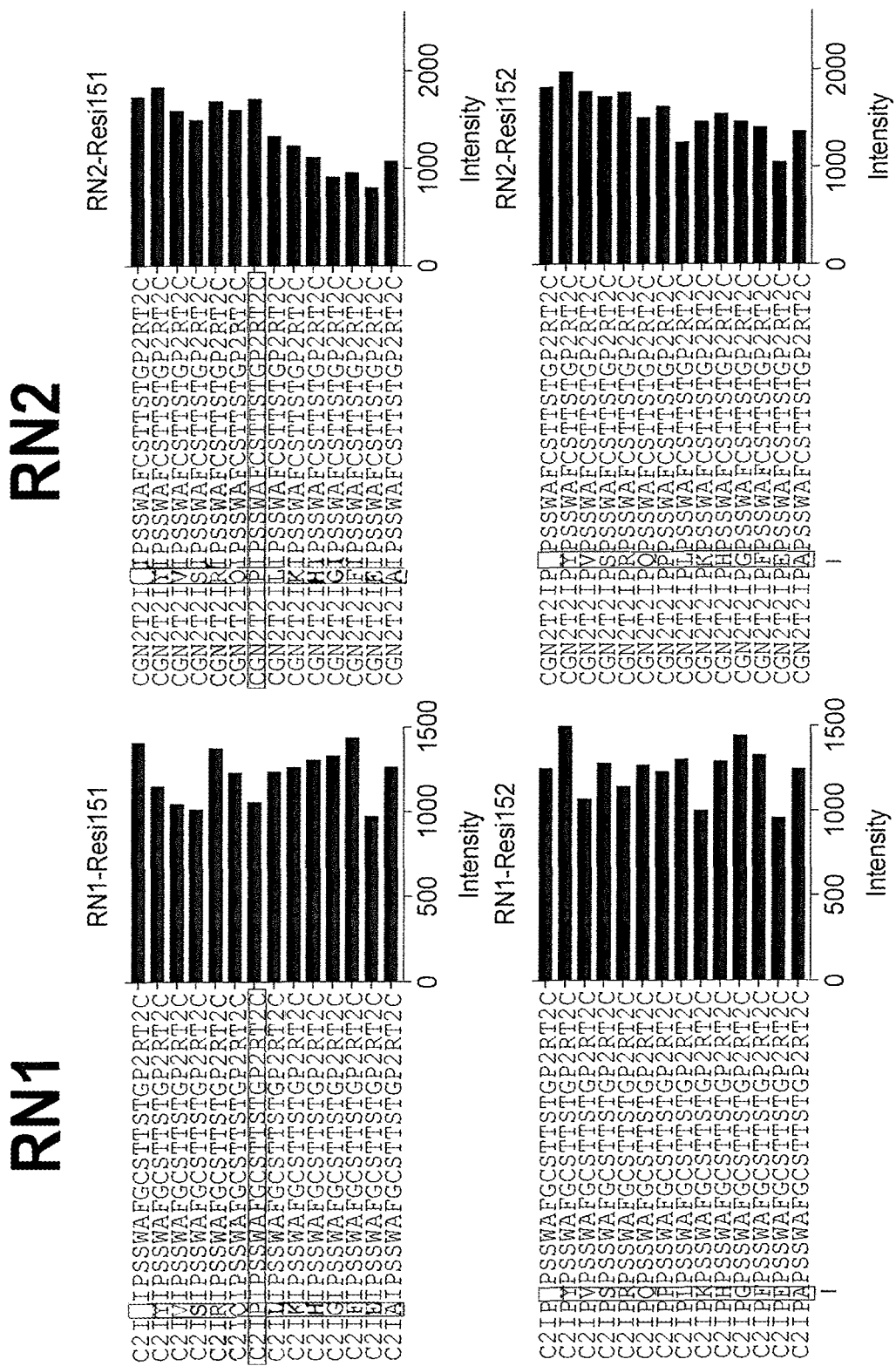
Figure 18:
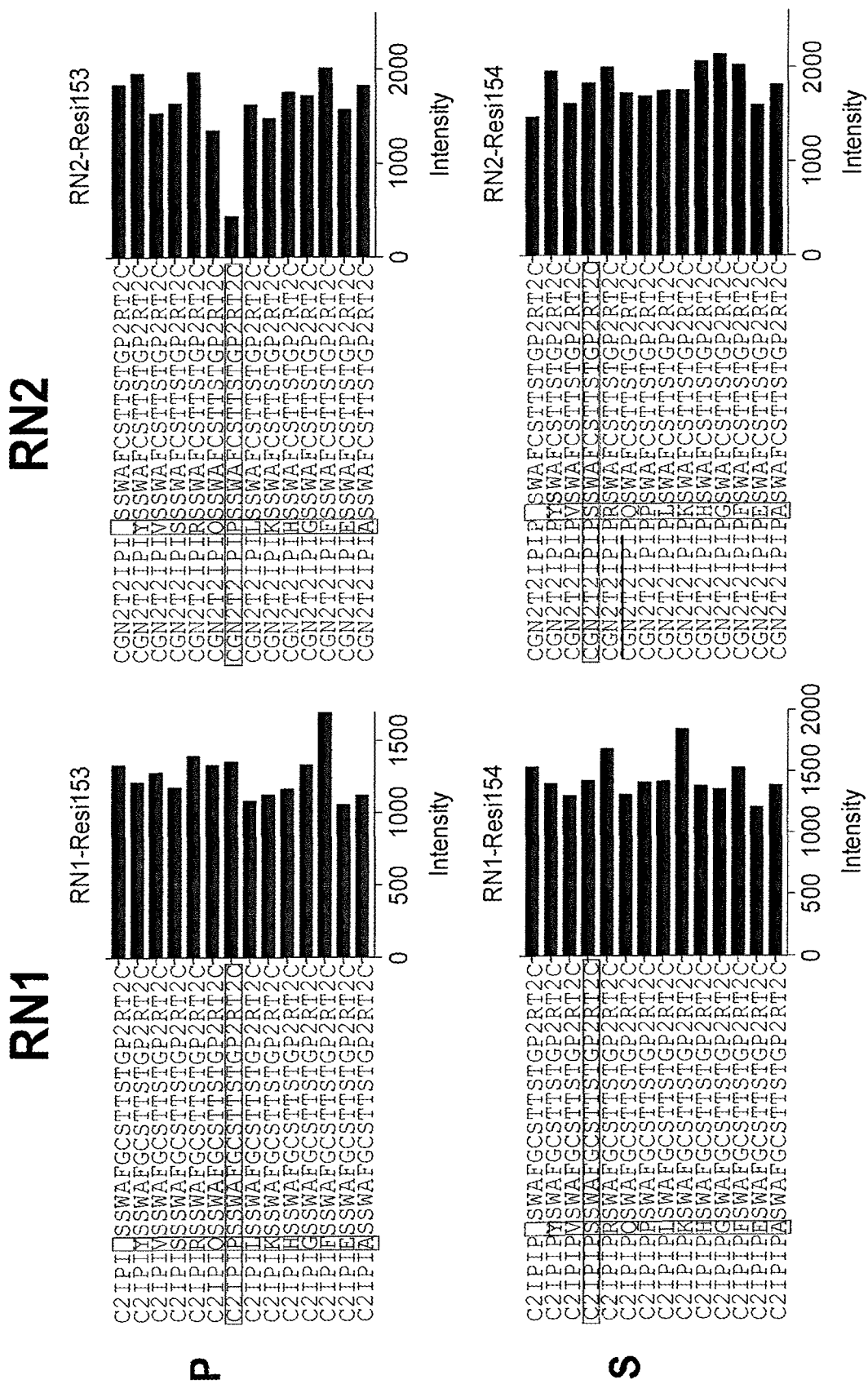
Figure 18:
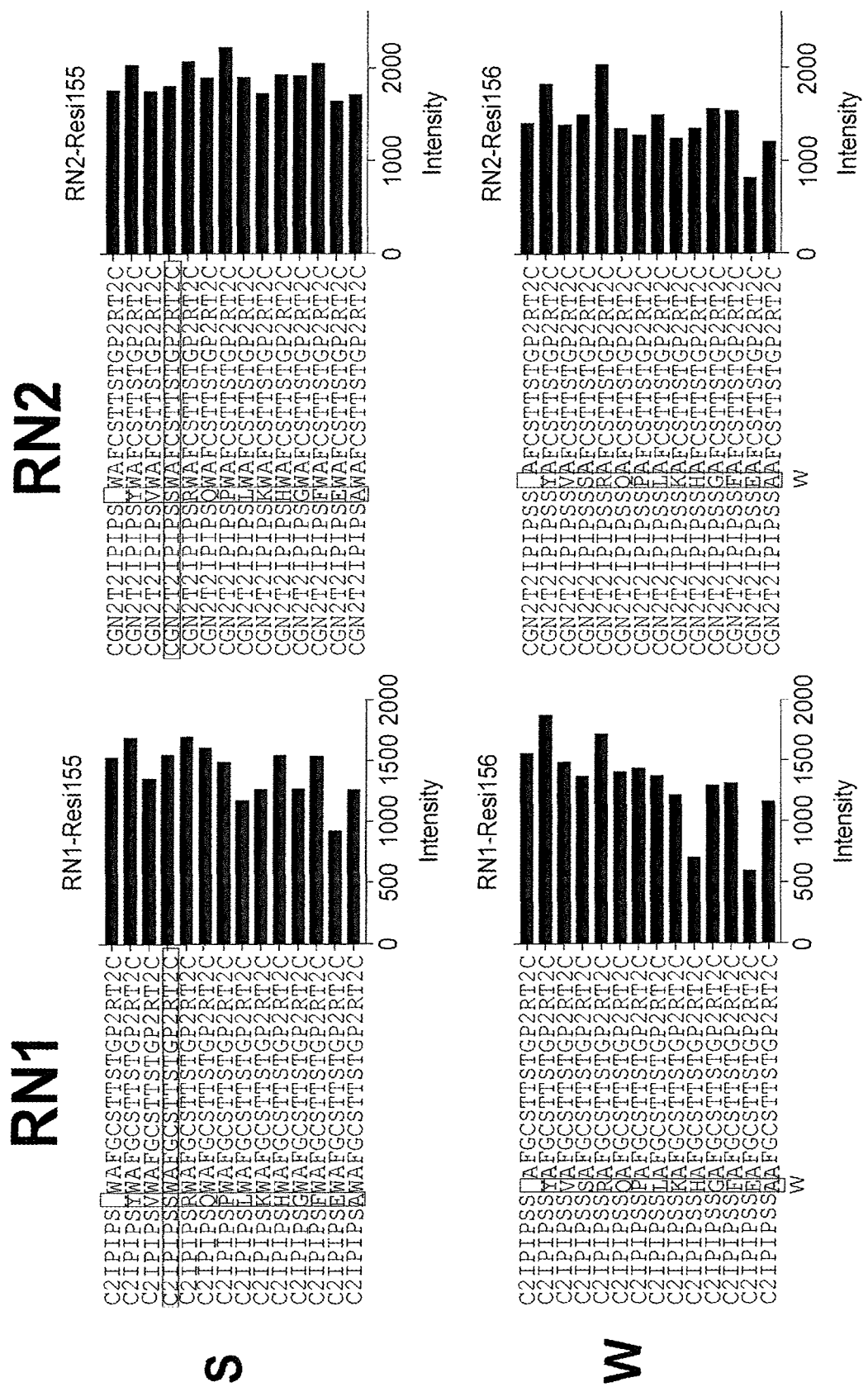
Figure 18:
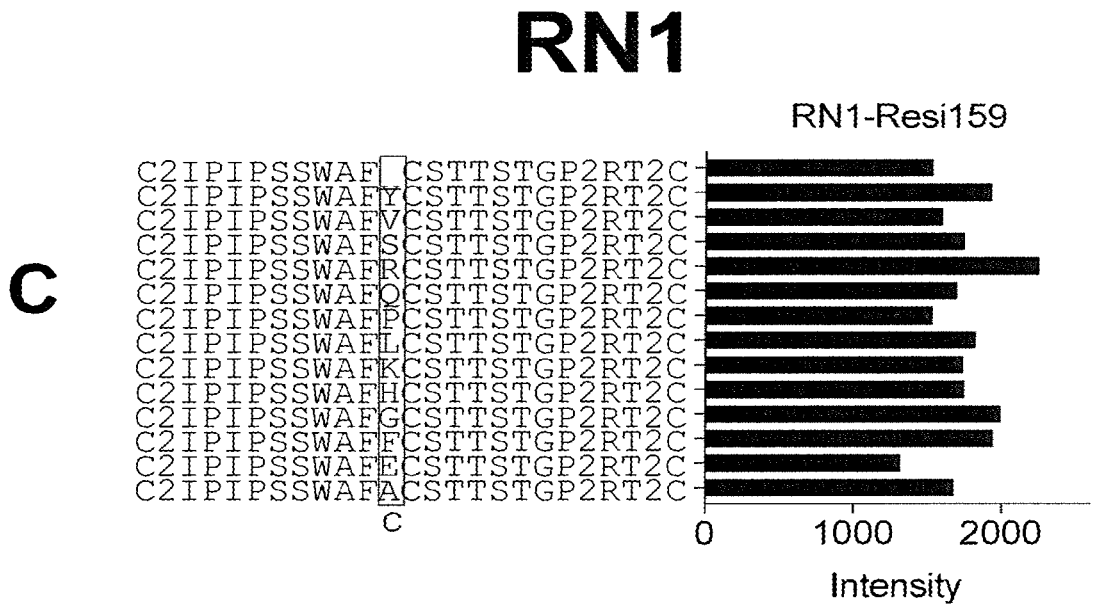

As expected, when tested under low stringency conditions antibody HBC34 bound peptides from all sets. Results of the experiment show that residues $_{120}PCR_{122}$ and $C_{124}$ are critical for the binding, while only certain replacements of residues 1150, 1152, W156 and F158 notably decrease the binding (FIG. 18). Moreover, data recorded on all three arrays coherently have shown that replacements of any residue within region $_{114}STTSTGPCRTC_{124}$ (SEQ ID NO: 85) with E would decrease the binding, while inverse replacements with R or Y increase binding. However, the same was not observed for region $_{145}GNCTCIPIPSS$-$WAFC_{159}$ (SEQ ID NO: 86).

Taken together these results suggest that antibody HBC34 recognizes a discontinuous epitope with residues $_{120}PCR_{122}$ and $C_{124}$ being crucial for the binding. Presence of residues $_{145}GNCTCIPIPSSWAF_{158}$ (SEQ ID NO: 87) was shown to provide structural context for establishing and stabilizing epitope-paratope interactions. This conclusion arose from the observation that discontinuous epitope mimics (when $_{145}GNCTCIPIPSSWAF_{158}$ (SEQ ID NO: 87) and $_{114}STTSTGPCRTC_{124}$ (SEQ ID NO: 85) are present in one mimic) are more tolerant to the replacements than sequence $_{114}STTSTGPCRTC_{124}$ (SEQ ID NO: 85) alone (set 3, RNS). Additionally, P151 which fixes the torsion angles thereby providing conformational rigidity was shown to impact the binding especially when replaced by G known for inversed properties. Replacement G145P similarly impacts binding of HBC34. It was repeatedly observed that R/Y replacements improve the binding to any position within motif $_{114}$STTSTGPCRTC$_{124}$ (SEQ ID NO: 85), but not within motif $_{145}$GNCTCIPIPSSWAF$_{158}$ (SEQ ID NO: 87), while E replacements decrease binding. This observation may suggest that residues $_{114}$STTSTGPCRTC$_{124}$ (SEQ ID NO: 85) bind to a negatively charged paratope within the antibody HBC34 (or close to a cluster of negative charges) and improvement of the binding as well as the decreased result from electrostatic forces and rather characterize the paratope features than those of the epitope.

Example 10: Increased Reduction of HBsAg in Chronically HBV Infected Humanized uPA Mice Treated with a Combination of HBC34 and Lamivudine In a further study, the efficacy of a combination therapy including the antibody HBC34 was investigated. For combination with HBC34, a polymerase inhibitor, namely lamivudine, was selected.

To mimic the chronic hepatitis B setting, naïve humanized uPA/SCID mice were infected with HBV and after 8 weeks post infection, a median level of HBV DNA of $2\times10^9$ copies/ml and a level of HBsAg of 9000 IU/ml was reached. These levels are as high as the levels that are commonly observed in human patients with chronic HBV infection.

Thereafter, mice were treated starting from week 8 post-infection either with antibody HBC34 alone, with the polymerase inhibitors lamivudine alone, with a combination of HBC34 and lamivudine, or with a control antibody for 4 weeks (HBC34 at 1 mg/kg i.p. twice per week; lamivudine supplemented in drinking water at 0.4 mg/ml).

HBV viremia and HBsAG levels in serum were assessed in treatment week 0 (before treatment), treatment week 2, treatment week 4, and treatment week 6, or in treatment week 0 (before treatment), treatment week 3 and treatment week 6. Results are shown in FIGS. 19 A (HBV viremia) and B (HBsAG).

Figure 19:
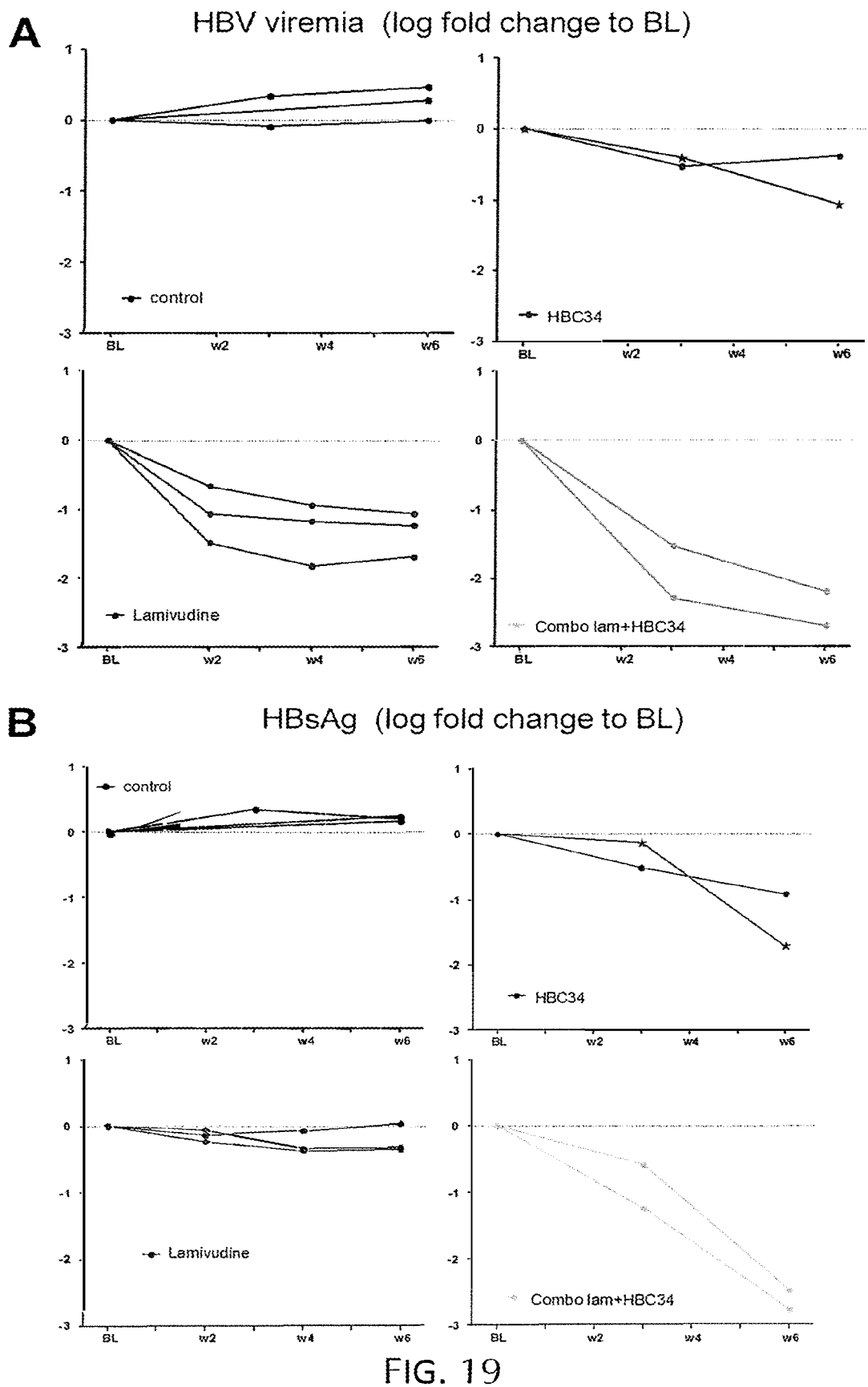
FIG. 19 shows for Example 10 the effect of a combination therapy with HBC34 (I mg/kg i.p twice a week) and Lamivudine (supplemented at 0.4 mg/ml in drinking water) in reducing the levels of HBV viremia (panel A) and circulating HBV-s-Antigen (panel B) in humanized uPA/SCID mice inoculated with $2 \times 10^9$ copies of HBV genome equivalents (genotype D), which received for 4 weeks starting from 8 weeks post-infection, treatment with either a control antibody (control), HBC34 alone (HBC34), lamivudine alone (Lamivudine) or a combination treatment (HBC34 and lamivudine). Combination therapy caused higher reduction of viremia compared with either drugs alone.

As shown in FIG. 19 treatment with HBC34, lamivudine or both drugs in combination caused mean 0.7 log, 1.3 log and 2.4 log reduction of viremia (A), respectively. Notably, HBsAg (B) dropped 1.3 log (mean BL=15,600 IU/ml) in mice receiving HBC34 alone and 2.6 log (mean BL=2,600 IU/ml) in the combination group, whereas no significant HBsAg reduction (0.2 log; mean BL=9,000 IU/ml) was detected in mice treated with lamivudine alone.

In summary, the combination of HBC34 and lamivudine clearly achieved the strongest effect. Interestingly, such a strong effect of the combination of HBC34 and lamivudine was observed, even if lamivudine alone was not effective. In view thereof, the observed strong effect of the combination of HBC34 and lamivudine is clearly an unexpected synergistic effect.

In summary, the surprisingly strong HBsAg reduction achieved in combination therapy proves that HBC34 antibody can be used, e.g. in chronic settings, in combination with polymerase inhibitors to accelerate HBsAg clearance both in HBV mono-infected and HBV/HDV co-infected patients.

Example 11: Sequence Engineering of HBC34 Antibody: CDR3 of VH and VL

Figure 20:
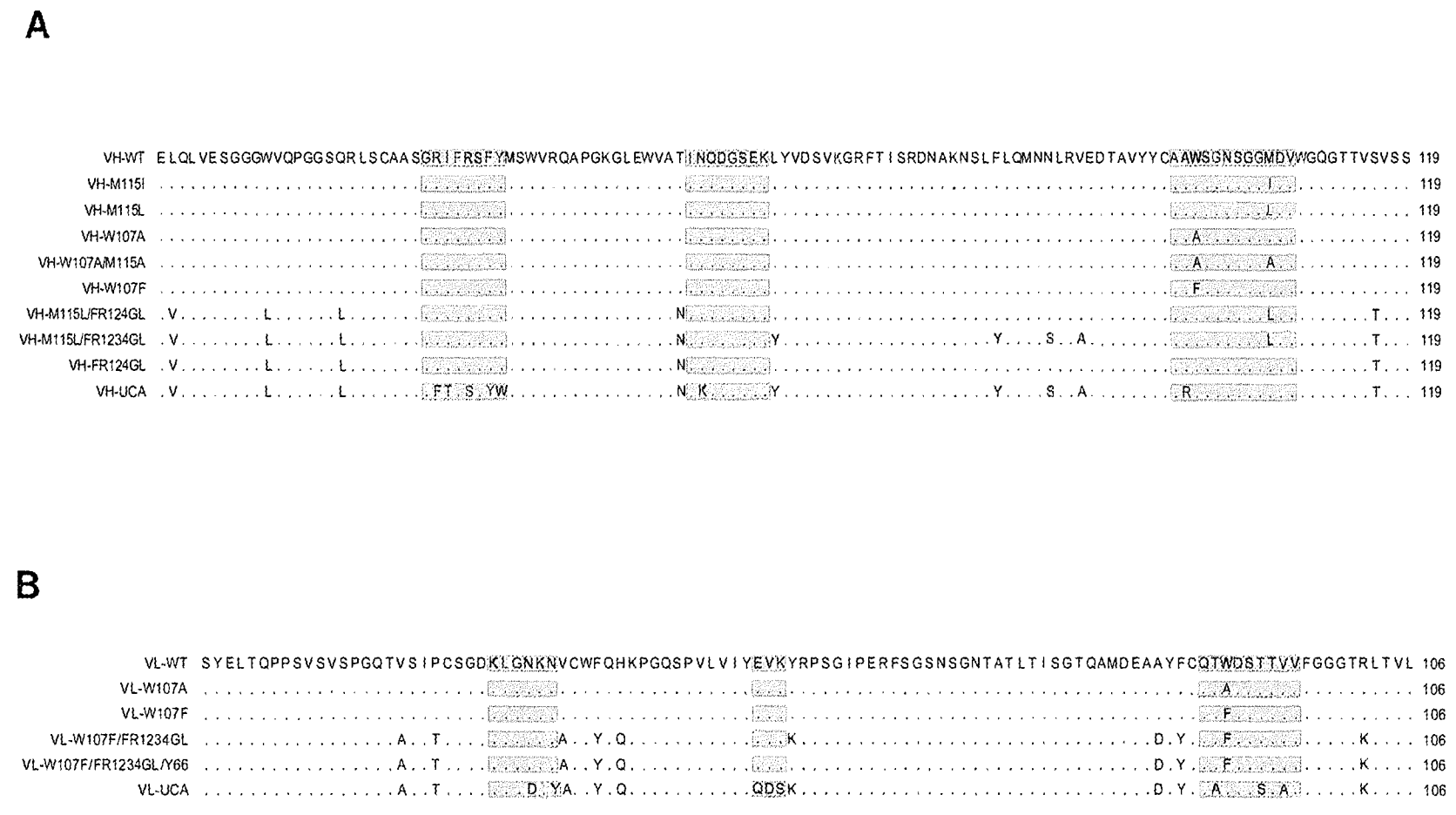

A first series of HBC34 mutants was generated with mutations in the CDR3 of VH and VL by mutating (i) residue W107 of the VH CDR3 into either A or F, (ii) residue M115 of the VH CDR3 into I or L, and/or (iii) residue W107 of the VL CDR3 into either A or F. A total of 18 HBC34 variants were produced by combining the un-mutated VH or VL of HBC34 (hereafter referred as WT, wild type or parental antibody) with different combinations of VH and VL mutants as illustrated in FIG. 20 and FIG. 21.

The produced HBC34 antibody variants were tested by ELISA for binding to HBsAg adw antigen, similarly as in Example 1. Results are shown in FIG. 21.

Of note, the mutation of W107 of the VH CDR3 into A (in HBC34-V5, HBC34-V8, HBC34-V9, HBC34-V10, HBC34-V12 and HBC34-V17 variants, FIG. 21) completely abolished HBC34 binding to HBsAg. This indicates that W107 is a key residue in the HBC34 paratope for antigen recognition. The mutation of W107 of the VH CDR3 into F (an amino acid with similar aromatic characteristic as W) partially affected HBC34 binding (HBC34-V1), indicating that W cannot be mutated without compromising HBC34 binding affinity to HBsAg.

The mutation of M115 of the VH CDR3 into L did not affect HBC34 binding (HBC34-V13), while the mutation into I (HBC34-V11) partially reduced HBC34 binding, indicating that M115 could be substituted by L, but not by I, without compromising HBC34 binding. Consistently with the results obtained with the single mutation W107A, the double mutation W107A and M115A (HBC34-V10) completely abolished HBC34 binding.

The mutation of W107 of the VL CDR3 into F did not affect HBC34 binding (HBC34-V7), while the mutation into A (HBC34-V15) partially reduced HBC34 binding, indicating that W107 of the VL CDR3 could be substituted by F, but not by A, without compromising HBC34 binding. As expected the combination of the mutations W107F in the CDR3 of the VH and W107A in the CDR3 of the VL completely abolished binding (HBC34-v2). The combination of the mutations M115L in VH CDR3 and W107F in VL CDR3s (HBC34-V6), of the mutations M115I in the VH CDR3 with W107F in the VL CDR3 (HBC34-v4) and of the mutations W107F in the VH CDR3 and W107F in the VL CDR3, partially affected HBC34 binding to HBsAg, indicating that the combination of these two mutations, but not the individual mutations, is not compatible to retain the binding affinity of the parental HBC34 antibody.

Figure 22:
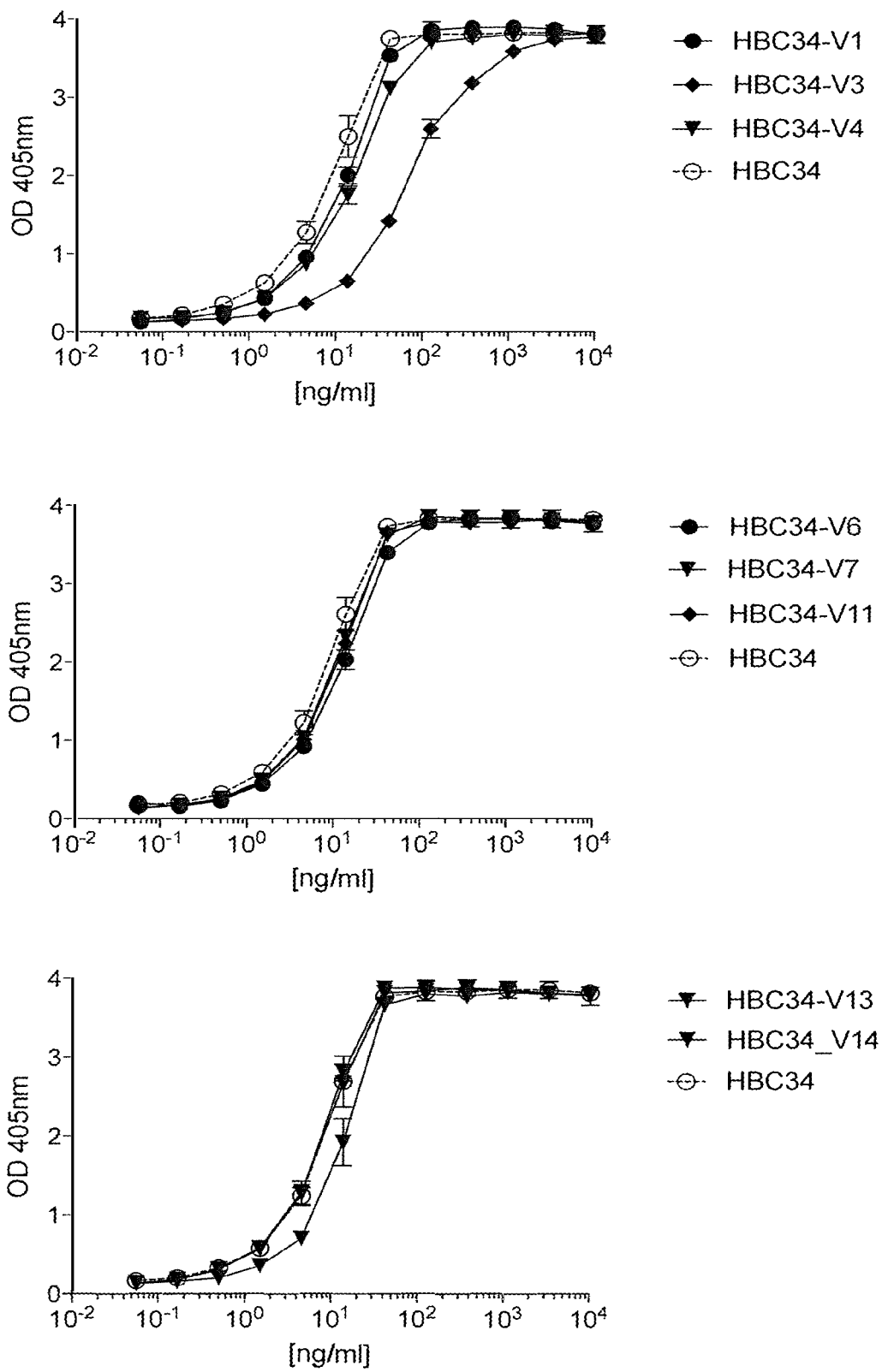
FIG. 22 shows for Example 11 binding of 8 different engineered variants of HBC34 to HBsAg (adw) as determine in direct antigen-based ELISA assay. These 8 variants were select among the 18 HBC34 mutants described in FIG. 21; in order to better characterize the affinity for HBsAg the 8 antibodies were titrated and compared with the parental antibody sequence.

In a next step, six of the 18 HBC34 variants described above were selected for further characterization (HBC34-V1, V3, V4, V6, V7, V11 and Vis) in order (i) to confirm the initial results; (ii) to measure the binding affinity by ELISA (i.e. to determine the EC50 of binding); and (iii) to assess the productivity of these HBC34 variants from transiently transfected 293-Expi cells (FIG. 22 and FIG. 23).

As observed in the first experiment, HBC34-V3 variant (carrying the double mutation W107F of the VH CDR3 and W107F of the VL CDR3) bound to HBsAg (adw serotype) with an EC50 9 fold higher as compared to the parental HBC34 antibody. In addition, HBC34-V3 is produced at a concentration almost 5 times lower as compared to HBC34. HBC34-V11 and HBC34-V13 variants carrying the single mutation M115I and M115L, respectively, bound to HBsAg with EC50 identical or slightly superior to that of HBC34. However, both variants were produced less efficiently than HBC34 (0.6× and 0.5× lower productivity when compared to HBC34). These results indicate that HBC34-V11, and even more HBC34-V13 variants, bind with high affinity to HBsAg but are produced less efficiently in mammalian cells. Similarly, HBC34-V1 variant carrying the single mutation W107F in the VH CDR3 bound to HBsAg comparably with HBC34 (1.6-fold higher EC50), but was produced 4-fold less efficiently (i.e. 0.25×) as compared to HBC34. The combination of W107 of the VL CDR3 with either W107, M115I or M115L of the VH CDR3 (HBC34-V3, HBC34-V4 and HBC34-V6) reduced both binding affinity (1.6-9.0 fold higher EC50) and productivity (0.20-0.35× lower antibody concentration in the culture supernatants). Surprisingly, the single mutation W107F of the VL CDR3 (HBC34-V7) bound to HBsAg similarly to HBC34 and was produced even more efficiently (up to 1.7×) than HBC34, reaching the remarkably high concentration in the culture supernatant of 533 µg/ml (FIG. 23).

Example 12: Sequence Engineering of HBC34 Antibody: Framework Regions

Twelve additional HBC34 variants were produced (HBC34-V19 to HBC34-V30; FIG. 24A) in which several mutations were introduced in the framework regions (FRs) of both VH and VL that corresponded to the residues found in the HBC34 unmutated common ancestor (HBC34-UCA) (FIG. 20) and combined with the VH CDR3 mutation M115L and with the VL CDR3 mutation W107F.

Results are shown in FIG. 24. The introduction of 9 mutations in the FRs of VL (HBC34-27, HBC34-V28, HBC34-V29 and HBC34-V30) in the presence of the W107 mutation in the VL CDR3, combined with the WT, M115L reduced significantly HBC34 binding to HBsAg, thus indicating an important role for the mutated residues in VL (FIG. 24A-B). HBC34 variants, wherein the same VL variant described above (i.e. W107F/FR1234-GL) was combined with the VH carrying the M115L mutation and additional 9 mutations in FRs, did not bind to HBsAg, indicating that mutations in both VH and VL contribute essentially to HBsAg binding.

Importantly, the removal of only one of the 9 mutations introduced in the FRs of VL (i.e. K66Y) in HBC34-V23 and HBC34-V24 increased significantly the binding (100× fold lower EC50) to HBsAg as compared to the corresponding variants carrying the Y66K mutation (HBC34-V27 and HBC34-V28). Similarly, the removal of the K66Y mutation in HBC34-V25 and HBC34-V26 restored HBsAg binding as compared to the corresponding non-binding variants carrying the Y66K mutation (HBC34-V27 and HBC34-V28).

Of these, the HBC34-V23 variant retained high affinity binding (1.5× higher EC50 as compared to HBC34) and was produced similarly to the parental HBC34 antibody. Of note, the HBC34-V24 variant differing for only one amino acid from HBC34-V23 variant (i.e. M115L in VH), bound to HBsAg with a EC50 similar to that of HBC34-V23 but was not produced efficiently (only 0.14× productivity as compared to HBC34). These results indicate that, while not affecting significantly the binding of HBC34 variants to HBsAg, the presence of L at position 115 has a negative impact on the productivity of HBC34 variants carrying this mutation. Indeed, on average all HBC34 variants carrying the M115L mutation (HBC34-V6, HBC34-V13, HBC34-V19, HBC34-V20, HBC34-V21, HBC34-V22, HBC34-V24, HBC34-V25, HBC34-V26, HBC34-V28, HBC34-V29 and HBC34-V30) have a mean productivity which is 0.3× as compared to that of the parental HBC34 antibody.

Remarkably, the introduction of 5 or 9 mutations in the FRs of VH in the presence of the M115L mutation in VH CDR3 (HBC34-V19 and HBC34-V20 variants, respectively) did not decrease appreciably the binding to HBsAg, suggesting that the mutated residues do not have an important role in the high affinity antigen recognition by HBC34 antibody. The introduction of the W107F mutation on the backbone of HBC34V19 and HBC34-V20 variants in HBC34-V21 and HBC34-V22 reduced the binding to HBsAg of 20-30×. Interestingly, the same mutation (i.e. W107 in the VL CDR3) did not affect the binding of other variants not carrying the same 5 or 9 mutations in the FRs of the VH, a result which might indicate that residues in the VH FRs have a cooperative role (e.g. by stabilizing a certain conformation of the variable region scaffold) in binding to HBsAg with residue 107 of the VH.

Finally and consistently with the results of Example 11 shown in FIG. 23, the HMB34-V7 antibody carrying the single mutation W107 in the VL CDR3 showed a comparable binding to HBsAg (i.e. 1.4×) as compared to HBC34 and was produced more efficiently (1.2×) than HBC34 (on average in the two experiments performed HBC34-V7 was produced 1.5×, i.e. 50%, more efficiently than HBC34 antibody. This result suggests that the W107F mutation in VL CDR3, while not affecting appreciably the binding affinity to HBsAg, has a positive impact on HBC34 antibody productivity.

Figure 25:
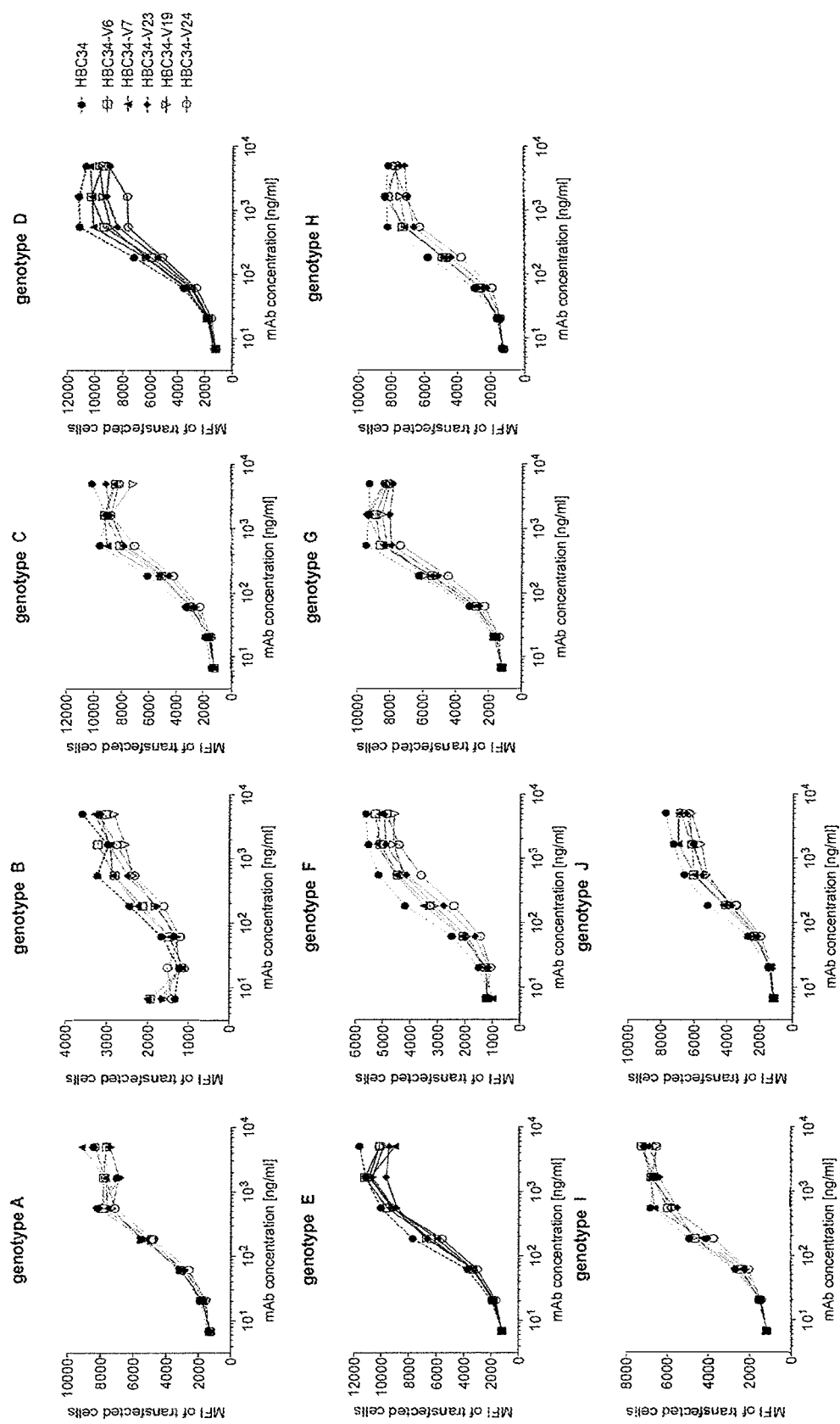
FIG. 25 shows for Examples 11 and 12 the binding, as determined by cytofluorimetric analysis, of HBC34 and variants 6, 7, 19, 23 and 24. All antibodies were titrated starting from 5 µg/ml and bound to permeabilized Hep2 cells transiently transfected with plasmids expressing the different HBsAg genotypes A, B, C, D, E, F, G, H, I and J.

Finally, HBC34 and the variants HBC34-V6, HBC34-V7, HBC34-V19, HBC34-V23 and HBC34-V24 were tested for their ability to recognize the 10 HBV genotypes A, B, C, D, E, F, G, H, I, and J (as shown in FIG. 25) by flow cytometry analysis. In particular, human epithelial cells (Hep2 cells) were transfected with plasmids expressing each of the HBsAg of the 10 HBV genotypes A, B, C, D, E, F, G, H, I, and J. All antibodies were tested at multiple concentrations (8 serial dilutions from 5000 ng/ml to 7 ng/ml) for staining of transiently transfected permeabilized cells. Two days after transfection, Hep2 cells were collected, fixed and permeabilized with saponin for immunostaining with HBC34 and the five selected variants. Binding of antibodies to transfected cells was analysed using a Becton Dickinson FACSCanto2 (BD Biosciences) with FlowJo software (TreeStar). As shown in FIG. 25, HBC34 and all of the five variants tested recognized all 10 HBV HBsAg genotypes at a similar level.

TABLE OF SEQUENCES AND SEQ ID NUMBERS (SEQUENCE LISTING):

| SEQ ID NO | Sequence | Remarks |
|---|---|---|
| 1 | $X_1X_2X_3TCX_4X_5X_6AX_7G$<br>wherein $X_1$, $X_2$, $X_3$, $X_4$, $X_5$, $X_6$ and $X_7$ may be any amino acid | epitope |
| 2 | $X_1X_2X_3TCX_4X_5X_6AX_7G$<br>wherein $X_1$, is P, T or S,<br>$X_2$ is C or S,<br>$X_3$ is R, K, D or I,<br>$X_4$ is M or T, | |

-continued

TABLE OF SEQUENCES AND SEQ ID NUMBERS (SEQUENCE LISTING):

| SEQ ID NO | Sequence | Remarks |
|---|---|---|
| | $X_5$ is T, A or I,<br>$X_6$ is T, P or L, and<br>$X_7$ is Q, H or L. | |
| 3 | MENITSGFLGPLLVLQAGFFLLTRILTIPQSLDSWWTSL<br>NFLGGTTVCLGQNSQSPTSNHSPTSCPPTCPGYRWMCL<br>RRFIIFLFILLLCLIFLLVLLDYQGMLPVCPLIPGSSTTST<br>GPCRTCMTTAQGTSMYPSCCCTKPSDGNCTCIPIPSSW<br>AFGKFLWEWASARFSWLSLLVPFVQWFVGLSPTVWLS<br>VIWMMWYWGPSLYSILSPFLPLLPIFFCLWVYI | S domain of HBsAg (GenBank acc. no. J02203) |
| 4 | MENVTSGFLGPLLVLQAGFFLLTRILTIPQSLDSWWTS<br>LNFLGGTTVCLGQNSQSPTSNHSPTSCPPTCPGYRWMC<br>LRRFIIFLFILLLCLIFLLVLLDYQGMLPVCPLIPGSSTTG<br>TGPCRTCTTPAQGTSMYPSCCCTKPSDGNCTCIPIPSSW<br>AFGKFLWEWASARFSWLSLLVPFVQWFVGLSPTVWLS<br>VIWMMWYWGPSLYSTLSPFLPLLPIFFCLWVYI | S domain of HBsAg (GenBank acc. no. FJ899792) |
| 5 | QGMLPVCPLIPGSSTTSTGPCRTCMTTAQGTSMYPSCC<br>CTKPSDGNCTCIPIPSSWAFGKFLWEWASARFSW | J02203 (D, ayw3) |
| 6 | QGMLPVCPLIPGSSTTGTGPCRTCTTPAQGTSMYPSCC<br>CTKPSDGNCTCIPIPSSWAFGKFLWEWASARFSW | FJ899792 (D, adw2) |
| 7 | QGMLPVCPLIPGTTTTSTGPCKTCTTPAQGNSMFPSCC<br>CTKPSDGNCTCIPIPSSWAFAKYLWEWASVRFSW | AM282986 (A) |
| 8 | QGMLPVCPLIPGSSTTSTGPCKTCTTPAQGTSMFPSCCC<br>TKPTDGNCTCIPIPSSWAFAKYLWEWASVRFSW | D23678 (B1) |
| 9 | QGMLPVCPLLPGTSTTSTGPCKTCTIPAQGTSMFPSCCC<br>TKPSDGNCTCIPIPSSWAFARFLWEWASVRFSW | AB117758 (C1) |
| 10 | QGMLPVCPLIPGSSTTSTGPCRTCTTLAQGTSMFPSCCC<br>SKPSDGNCTCIPIPSSWAFGKFLWEWASARFSW | AB205192 (E) |
| 11 | QGMLPVCPLLPGSTTTSTGPCKTCTTLAQGTSMFPSCC<br>CSKPSDGNCTCIPIPSSWALGKYLWEWASARFSW | X69798 (F4) |
| 12 | QGMLPVCPLIPGSSTTSTGPCKTCTTPAQGNSMYPSCCC<br>TKPSDGNCTCIPIPSSWAFAKYLWEWASVRFSW | AF160501 (G) |
| 13 | QGMLPVCPLLPGSTTTSTGPCKTCTTLAQGTSMFPSCC<br>CTKPSDGNCTCIPIPSSWAFGKYLWEWASARFSW | AY090454 (H) |
| 14 | QGMLPVCPLIPGSSTTSTGPCKTCTTPAQGNSMYPSCCC<br>TKPSDGNCTCIPIPSSWAFAKYLWEWASARFSW | AF241409 (I) |
| 15 | QGMLPVCPLLPGSTTTSTGPCRTCTITAQGTSMFPSCC<br>CTKPSDGNCTCIPIPSSWAFAKFLWEWASVRFSW | AB486012 (J) |
| 16 | CQGMLPVCPLIPGSSTTGTGTCRTCTTPAQGTSMYPSC<br>CCTKPSDGNCTCIPIPSSWAFGKFLWEWASARFSW | HBsAg Y100C/P120T |
| 17 | QGMLPVCPLIPGSSTTGTGTCRTCTTPAQGTSMYPSCC<br>CTKPSDGNCTCIPIPSSWAFGKFLWEWASARFSW | HBsAg P120T |
| 18 | QGMLPVCPLIPGSSTTGTGTCRTCTTPAQGTSMYPSCC<br>CTKPLDGNCTCIPIPSSWAFGKFLWEWASARFSW | HBsAg P120T/S143L |
| 19 | QGMLPVCPLIPGSSTTGTGPSRTCTTPAQGTSMYPSCC<br>CTKPSDGNCTCIPIPSSWAFGKFLWEWASARFSW | HBsAg C121S |
| 20 | QGMLPVCPLIPGSSTTGTGPCDTCTTPAQGTSMYPSCC<br>CTKPSDGNCTCIPIPSSWAFGKFLWEWASARFSW | HBsAg R122D |
| 21 | QGMLPVCPLIPGSSTTGTGPCITCTTPAQGTSMYPSCCC<br>TKPSDGNCTCIPIPSSWAFGKFLWEWASARFSW | HBsAg R122I |
| 22 | QGMLPVCPLIPGSSTTGTGPCRNCTTPAQGTSMYPSCC<br>CTKPSDGNCTCIPIPSSWAFGKFLWEWASARFSW | HBsAg T123N |

TABLE OF SEQUENCES AND SEQ ID NUMBERS (SEQUENCE LISTING):

| SEQ ID NO | Sequence | Remarks |
|---|---|---|
| 23 | QGMLPVCPLIPGSSTTGTGPCRTCTTPAHGTSMYPSCC CTKPSDGNCTCIPIPSSWAFGKFLWEWASARFSW | HBsAg Q129H |
| 24 | QGMLPVCPLIPGSSTTGTGPCRTCTTPALGTSMYPSCC CTKPSDGNCTCIPIPSSWAFGKFLWEWASARFSW | HBsAg Q129L |
| 25 | QGMLPVCPLIPGSSTTGTGPCRTCTTPAQGTSHYPSCC CTKPSDGNCTCIPIPSSWAFGKFLWEWASARFSW | HBsAg M133H |
| 26 | QGMLPVCPLIPGSSTTGTGPCRTCTTPAQGTSLYPSCCC TKPSDGNCTCIPIPSSWAFGKFLWEWASARFSW | HBsAg M133L |
| 27 | QGMLPVCPLIPGSSTTGTGPCRTCTTPAQGTSTYPSCC CTKPSDGNCTCIPIPSSWAFGKFLWEWASARFSW | HBsAg M133T |
| 28 | QGMLPVCPLIPGSSTTGTGPCRTCTTPAQGTSMYPSCC CTEPSDGNCTCIPIPSSWAFGKFLWEWASARFSW | HBsAg K141E |
| 29 | QGMLPVCPLIPGSSTTGTGPCRTCTTPAQGTSMYPSCC CTKSSDGNCTCIPIPSSWAFGKFLWEWASARFSW | HBsAg P142S |
| 30 | QGMLPVCPLIPGSSTTGTGPCRTCTTPAQGTSMYPSCC CTKPKDGNCTCIPIPSSWAFGKFLWEWASARFSW | HBsAg S143K |
| 31 | QGMLPVCPLIPGSSTTGTGPCRTCTTPAQGTSMYPSCC CTKPSAGNCTCIPIPSSWAFGKFLWEWASARFSW | HBsAg D144A |
| 32 | QGMLPVCPLIPGSSTTGTGPCRTCTTPAQGTSMYPSCC CTKPSDRNCTCIPIPSSWAFGKFLWEWASARFSW | HBsAg G145R |
| 33 | QGMLPVCPLIPGSSTTGTGPCRTCTTPAQGTSMYPSCC CTKPSDGACTCIPIPSSWAFGKFLWEWASARFSW | HBsAg N146A |
| 34 | GRIFRSFY | CDRH1 aa |
| 35 | NQDGSEK | CDRH2 aa |
| 36 | AAWSGNSGGMDV | CDRH3 aa |
| 37 | KLGNKN | CDRL1 aa |
| 38 | EVK | CDRL2 aa |
| 39 | VIYEVKYRP | CDRL2 long aa |
| 40 | QTWDSTTVV | CDRL3 aa |
| 41 | ELQLVESGGGWVQPGGSQRLSCAASGRIFRSFYMSWVR QAPGKGLEWVATINQDGSEKLYVDSVKGRFTISRDNAK NSLFLQMNNLRVEDTAVYYCAAWSGNSGGMDVWGQ GTTVSVSS | VH aa |
| 42 | SYELTQPPSVSVSPGQTVSIPCSGDKLGNKNVCWFQHKP GQSPVLVIYEVKYRPSGIPERFSGSNSGNTATLTISGTQA MDEAAYFCQTWDSTTVVFGGGTRLTVL | VL aa |
| 43 | GGACGCATCTTTAGAAGTTTTTAC | CDRH1 nuc |
| 44 | ATAAACCAAGATGGAAGTGAGAAA | CDRH2 nuc |
| 45 | GCGGCTTGGAGCGGCAATAGTGGGGGTATGGACGT C | CDRH3 nuc |
| 46 | AAATTGGGGAATAAAAAT | CDRL1 nuc |
| 47 | GAGGTTAAA | CDRL2 nuc |
| 48 | gtcatctatGAGGTTAAAtaccgcccc | CDRL2 long nuc |
| 49 | CAGACGTGGGACAGCACCACTGTGGTG | CDRL3 nuc |

TABLE OF SEQUENCES AND SEQ ID NUMBERS (SEQUENCE LISTING):

| SEQ ID NO | Sequence | Remarks |
|---|---|---|
| 50 | GAACTGCAGCTGGTGGAGTCTGGGGGAGGCTGGGTC CAGCCGGGGGGGTCCCAGAGACTGTCCTGTGCAGCC TCTGGACGCATCTTTAGAAGTTTTTACATGAGCTGGG TCCGCCAGGCCCCAGGGAAGGGGCTGGAGTGGGTG GCCACTATAAACCAAGATGGAAGTGAGAAATTATAT GTGGACTCTGTGAAGGGCCGATTCACCATCTCCAGA GACAACGCCAAGAACTCACTATTTCTGCAAATGAACA ACCTGAGAGTCGAGGACACGGCCGTTTATTACTGCG CGGCTTGGAGCGGCAATAGTGGGGGTATGGACGTC TGGGGCCAGGGGACCACGGTCTCCGTCTCCTCA | VH nuc |
| 51 | TCCTATGAGCTGACTCAGCCACCCTCAGTGTCCGTGT CCCCAGGACAGACAGTCAGCATCCCTGCTCTGGAG ATAAATTGGGGAATAAAAATGTTTGCTGGTTTCAGCA TAAGCCAGGCCAGTCCCCTGTGTTGGTCATCTATGAG GTTAAATACCGCCCCTCGGGGATTCCTGAGCGATTCT CTGGCTCCAACTCTGGGAACACAGCCACTCTGACCAT CAGCGGGACCCAGGCTATGGATGAGGCTGCCTATTT CTGTCAGACGTGGGACAGCACCACTGTGGTGTTCGG CGGAGGGACCAGGCTGACCGTCCTA | VL nuc |
| 52 | XGSSTTSTGPCRTCMTXPSDGNATAIPIPSSWX wherein the residues coded as X were substituted with Cysteines | peptide |
| 53 | TSTGPCRTCMTTAQG | peptide |
| 54 | GMLPVCPLIPGSSTTSTGPCRTCMTT | peptide |
| 55 | XSMYPSASATKPSDGNXTGPCRTCMTTAQGTSX wherein the residues coded as X were substituted with Cysteines | peptide |
| 56 | PCRTCMTTAQG | amino acids 120-130 of the S domain of HBsAg (HBV-D J02203 |
| 57 | PCX₁TCX₂X₃X₄AQG, wherein X₁ is preferably R or K, X₂ is preferably M or T, X₃ is preferably T or I, and X₄ is preferably T, P or L | epitope |
| 58 | QTFDSTTVV | CDRL3 v7 and CDRL3 v23 (aa) |
| 59 | SYELTQPPSVSVSPGQTVSIPCSGDKLGNKNVCWFQHKP GQSPVLVIYEVKYRPSGIPERFSGSNSGNTATLTISGTQA MDEAAYFCQTFDSTTVVFGGGTRLTVL | VL v7 |
| 60 | AAGCTGGGGAACAAAAAT | CDRL1 v7 and CDRL1 v23 (nuc) |
| 61 | GAGGTGAAA | CDRL2 v7 and CDRL2 v23 nuc |
| 62 | GTCATCTACGAGGTGAAATATCGGCCT | CDRL2 long v7 and CDRL2 long v23 nuc |
| 63 | CAGACATTCGATTCCACCACAGTGGTC | CDRL3 v7 and CDRL3 v23 nuc |
| 64 | TCTTACGAGCTGACACAGCCACCTAGCGTGTCCGTCT CTCCAGGACAGACCGTGTCCATCCCTTGCTCTGGCGA CAAGCTGGGGAACAAAAATGTCTGTTGGTTCCAGCA CAAGCCAGGGCAGAGTCCCGTGCTGGTCATCTACGAG GTGAAATATCGGCCTTCAGGAATTCCAGAACGGTTCA GCGGATCAAACAGCGGCAATACTGCAACCCTGACAAT TAGCGGGACCCAGGCCATGGACGAAGCCGCTTATTTC TGCCAGACATTCGATTCCACCACAGTGGTCTTTGGC GGGGGAACTAGGCTGACCGTGCTG | VL v7 nuc |

TABLE OF SEQUENCES AND SEQ ID NUMBERS (SEQUENCE LISTING):

| SEQ ID NO | Sequence | Remarks |
|---|---|---|
| 65 | SYELTQPPSVSVSPGQTASITCSGDKLGNKNACWYQQKPGQSPVLVIYEVKYRPSGIPERFSGSNSGNTATLTISGTQAMDEADYYCQTFDSTTVVFGGGTKLTVL | VL v23 aa |
| 66 | INQDGSEK | HBC34wt CDRH2 aa |
| 67 | EVQLVESGGGLVQPGGSLRLSCAASGRIFRSFYMSWVRQAPGKGLEWVANINQDGSEKLYVDSVKGRFTISRDNAKNSLFLQMNNLRVEDTAVYYCAAWSGNSGGMDVWGQGTTVTVSS | HBC34 v31, HBC34 v32 and HBC34 v33 VH |
| 68 | GAGGTGCAGCTGGTGGAATCCGGCGGGGGACTGGTGCAGCCTGGCGGCTCACTGAGACTGAGCTGTGCAGCTTCTGGAAGAATCTTCAGATCTTTTTACATGAGTTGGGTGAGACAGGCTCCTGGGAAGGGACTGGAGTGGGTCGCAAACATCAATCAGGACGGATCAGAAAAGCTGTATGTGGATAGCGTCAAAGGCAGGTTCACTATTTCCCGCGACAACGCCAAAAATTCTCTGTTTCTGCAGATGAACAATCTGCGGGTGGAGGATACCGCTGTCTACTATTGTGCAGCCTGGTCTGGCAACAGTGGAGGCATGGACGTGTGGGGACAGGGAACCACAGTGACAGTCAGCTCC | HBC34 v31, HBC34 v32 and HBC34 v33 VH (nuc) |
| 69 | TCTTACGAGCTGACACAGCCCCCTAGCGTGTCCGTCTCTCCAGGCCAGACAGCATCCATCACTTGCTCTGGCGACAAGCTGGGGAACAAAAATGCCTGTTGGTATCAGCAGAAGCCAGGGCAGAGTCCCGTGCTGGTCATCTACGAGGTGAAATATCGGCCTTCAGGAATTCCAGAAAGATTCAGTGGATCAAACAGCGGCAATACTGCTACCCTGACAATTAGCGGGACCCAGGCCATGGACGAAGCTGATTACTATTGCCAGACATTCGATTCCACCACAGTGGTCTTTGGCGGGGGAACTAAGCTGACCGTGCTG | VL v23 nuc |
| 70 | GAACTGCAGCTGGTCGAATCAGGAGGAGGGTGGGTCCAGCCCGGAGGGAGCCAGAGACTGTCTTGTGCCGCATCAGGGAGGATCTTCAGGAGCTTCTACATGTCCTGGGTGCGCCAGGCACCAGGCAAGGGACTGGAGTGGGTCGCCACCATCAACCAGGACGGATCTGAAAAGCTGTATGTGGATAGTGTCAAAGGCCGGTTCACAATTAGCAGAGACAACGCTAAAAATTCTCTGTTTCTGCAGATGAACAATCTGCGAGTGGAGGATACCGCCGTCTACTATTGCGCCGCTTGGTCTGGCAACAGCGGCGGGATGGATGTCTGGGGGCAGGGCACAACAGTGAGCGTCTCTTCC | HBC34 wt VH codon optimized |
| 71 | TCATACGAACTGACTCAGCCTCCCTCCGTCTCCGTCTCACCTGGACAGACCGTCTCAATCCCCTGCTCCGGCGATAAACTGGGCAACAAGAACGTGTGCTGGTTCCAGCACAAACCCGGACAGAGTCCTGTGCTGGTCATCTACGAGGTCAAGTATCGGCCAAGCGGCATTCCCGAAAGATTCAGCGGCTCCAACTCTGGGAATACCGCAACACTGACTATCTCTGGAACCCAGGCAATGGACGAGGCAGCTTACTTTTGCCAGACTTGGGATTCAACTACTGTCGTGTTCGGCGGCGGAACTAGACTGACTGTCCTG | HBC34 wt VL codon optimized |
| 72 | GGGAGGATCTTCAGGAGCTTCTAC | HBC34 wt CDRH1 codon optimized |
| 73 | ATCAACCAGGACGGATCTGAAAAG | HBC34 wt CDRH2 codon optimized |
| 74 | GCCGCTTGGTCTGGCAACAGCGGCGGGATGGATGTC | HBC34 wt CDRH3 codon optimized |
| 75 | AAACTGGGCAACAAGAAC | HBC34 wt CDRL1 codon optimized |
| 76 | GAGGTCAAG | HBC34 wt CDRL2 codon optimized |
| 77 | GTCATCTACGAGGTCAAGTATCGGCCA | HBC34 wt CDRL2 long codon optimized |

TABLE OF SEQUENCES AND SEQ ID NUMBERS (SEQUENCE LISTING):

| SEQ ID NO | Sequence | Remarks |
|---|---|---|
| 78 | CAGACTTGGGATTCAACTACTGTCGTG | HBC34 wt CDRL3 codon optimized |
| 79 | GGSGG | linker |
| 80 | TGPCRTC | epitope |
| 81 | GNCTCIP | epitope |
| 82 | CCIPIPSSWAFGCSTTSTGPCRTCC wherein in particular thy cysteines at positions 2, 21, and 24 are coupled to acetamidomethyl. | discontinuous epitope mimic |
| 83 | CGNCTCIPIPSSWAFCSTTSTGPCRTCC wherein in particular thy cysteines at positions 4, 6, 24, and 27 are coupled to acetamidomethyl. | discontinuous epitope mimic |
| 84 | CGGGCSTTSTGPCRTCC wherein in particular thy cysteines at positions 13 and 16 are coupled to acetamidomethyl. | looped epitope mimic |
| 85 | STTSTGPCRTC | epitope |
| 86 | GNCTCIPIPSSWAFC | epitope |
| 87 | GNCTCIPIPSSWAF | epitope |
| 88 | PCRXC | epitope |

The invention claimed is:

1. An isolated antibody, or an antigen-binding fragment thereof, wherein the antibody or antigen-binding fragment thereof comprises CDRH1, CDRH2, and CDRH3 amino acid sequences and CDRL1, CDRL2, and CDRL3 amino acid sequences comprising:
   (i) SEQ ID NOs: 34-38 and 40, respectively;
   (ii) SEQ ID NOs: 34-37, 39, and 40, respectively;
   (iii) SEQ ID NOs: 34, 66, 36, 37, 38, and 40, respectively;
   (iv) SEQ ID NOs: 34, 66, 36, 37, 39, and 40, respectively;
   (v) SEQ ID NOs: 34-38 and 58, respectively;
   (vi) SEQ ID NOs: 34-37, 39, and 58, respectively;
   (vii) SEQ ID NOs: 34, 35, 36, 37, 38, and 58, respectively; or
   (viii) SEQ ID NOs: 34, 66, 36, 37, 39, and 58, respectively.

2. The antibody, or antigen-binding fragment thereof, of claim 1, comprising a heavy chain variable domain ($V_H$) and a light chain variable domain ($V_L$), wherein $V_H$ and $V_L$ comprise amino acid sequences having at least 95% identity to:
   (i) SEQ ID NOs: 41 and 42, respectively;
   (ii) SEQ ID NOs: 41 and 59, respectively;
   (iii) SEQ ID NOs: 41 and 65, respectively;
   (iv) SEQ ID NOs: 67 and 42, respectively;
   (v) SEQ ID NOs: 67 and 59, respectively; or
   (vi) SEQ ID NOs: 67 and 65, respectively.

3. The antibody, or antigen-binding fragment thereof, of claim 1, wherein the antibody, or the antigen-binding fragment thereof, comprises a Fc moiety.

4. The antibody, or antigen-binding fragment thereof, of claim 1, wherein the antibody, or antigen-binding fragment thereof, is human.

5. The antibody, or antigen-binding fragment thereof, of claim 1, wherein the antibody or antigen-binding fragment thereof comprises a purified antibody, a single chain antibody, a Fab, a Fab', a F(ab')2, a Fv, or a scFv.

6. A nucleic acid molecule comprising a polynucleotide encoding the antibody, or antigen-binding fragment thereof, of claim 1.

7. The nucleic acid molecule of claim 6, wherein the polynucleotide is codon-optimized for expression in a host cell.

8. A vector comprising the nucleic acid molecule according to claim 7.

9. A cell comprising the nucleic acid of claim 7.

10. A pharmaceutical composition comprising the antibody, or antigen-binding fragment thereof, of claim 1, and a pharmaceutically acceptable excipient, diluent, or carrier.

11. A kit, comprising the antibody, or antigen-binding fragment thereof, of claim 1, and one or more of:
   a polymerase inhibitor;
   (ii) an interferon; or
   (iii) a checkpoint inhibitor.

12. A method for treating a hepatitis B and/or a hepatitis D infection, the method comprising administering to a subject in need thereof an effective amount of an antibody, or an antigen-binding fragment thereof, wherein the antibody or the antigen-binding fragment comprises CDRH1, CDRH2, and CDRH3 amino acid sequences and CDRL1, CDRL2, and CDRL3 amino acid sequences of:
   (i) SEQ ID NOs: 34-38 and 40, respectively;
   (ii) SEQ ID NOs: 34-37, 39, and 40, respectively;
   (iii) SEQ ID NOs: 34, 66, 36, 37, 38, and 40, respectively;
   (iv) SEQ ID NOs: 34, 66, 36, 37, 39, and 40, respectively;
   (v) SEQ ID NOs: 34-38 and 58, respectively;
   (vi) SEQ ID NOs: 34-37, 39, and 58, respectively;
   (vii) SEQ ID NOs: 34, 35, 36, 37, 38, and 58, respectively; or
   (viii) SEQ ID NOs: 34, 66, 36, 37, 39, and 58, respectively.

13. The method of claim 12, wherein the antibody or antigen-binding fragment thereof comprises a heavy chain variable domain ($V_H$) and a light chain variable domain ($V_L$), wherein $V_H$ and $V_L$ comprise amino acid sequences having at least 95% identity to:
   (i) SEQ ID NOs: 41 and 42, respectively;
   (ii) SEQ ID NOs: 41 and 59, respectively;
   (iii) SEQ ID NOs: 41 and 65, respectively;
   (iv) SEQ ID NOs: 67 and 42, respectively;
   (v) SEQ ID NOs: 67 and 59, respectively; or
   (vi) SEQ ID NOs: 67 and 65, respectively.

14. The method of claim 12, wherein the subject is receiving or has received one or more of:
   a polymerase inhibitor;
   (ii) an interferon; and
   (iii) a checkpoint inhibitor.

15. The method of claim 14, wherein the polymerase inhibitor comprises lamivudine.

16. The method of claim 12, wherein the hepatitis B infection is a chronic hepatitis B infection.

17. The method of claim 12, wherein the subject has received a liver transplant.

18. The method of claim 12, wherein the subject is non-immunized against hepatitis B.

19. The method of claim 12, wherein the subject is a newborn.

20. The method of claim 12, wherein the subject is undergoing or has undergone hemodialysis.

* * * * *

```
                        SEQUENCE LISTING

Sequence total quantity: 92
SEQ ID NO: 1            moltype = AA  length = 11
FEATURE                 Location/Qualifiers
source                  1..11
                        mol_type = protein
                        note = epitope
                        organism = synthetic construct
SEQUENCE: 1
XXXTCXXXAX G                                                          11

SEQ ID NO: 2            moltype = AA  length = 11
FEATURE                 Location/Qualifiers
VARIANT                 1
                        note = X is P, T or S
VARIANT                 2
                        note = X is C or S
VARIANT                 3
                        note = X is R, K, D or I
VARIANT                 6
                        note = X is M or T
VARIANT                 7
                        note = X is T, A or I
VARIANT                 10
                        note = X is Q, H or L
source                  1..11
                        mol_type = protein
                        note = epitope
                        organism = synthetic construct
VARIANT                 8
                        note = X is T, P or L
SEQUENCE: 2
XXXTCXXXAX G                                                          11

SEQ ID NO: 3            moltype = AA  length = 226
FEATURE                 Location/Qualifiers
source                  1..226
                        mol_type = protein
```

```
                              note = S domain of HBsAg (GenBank acc. no. J02203)
                              organism = synthetic construct
SEQUENCE: 3
MENITSGFLG  PLLVLQAGFF  LLTRILTIPQ  SLDSWWTSLN  FLGGTTVCLG  QNSQSPTSNH   60
SPTSCPPTCP  GYRWMCLRRF  IIFLFILLLC  LIFLLVLLDY  QGMLPVCPLI  PGSSTTSTGP  120
CRTCMTTAQG  TSMYPSCCCT  KPSDGNCTCI  PIPSSWAFGK  FLWEWASARF  SWLSLLVPFV  180
QWFVGLSPTV  WLSVIWMMWY  WGPSLYSILS  PFLPLLPIFF  CLWVYI                 226

SEQ ID NO: 4                  moltype = AA  length = 226
FEATURE                       Location/Qualifiers
source                        1..226
                              mol_type = protein
                              note = S domain of HBsAg (GenBank acc. no. FJ899792)
                              organism = synthetic construct
SEQUENCE: 4
MENVTSGFLG  PLLVLQAGFF  LLTRILTIPQ  SLDSWWTSLN  FLGGTTVCLG  QNSQSPTSNH   60
SPTSCPPTCP  GYRWMCLRRF  IIFLFILLLC  LIFLLVLLDY  QGMLPVCPLI  PGSSTTGTGP  120
CRTCTTPAQG  TSMYPSCCCT  KPSDGNCTCI  PIPSSWAFGK  FLWEWASARF  SWLSLLVPFV  180
QWFVGLSPTV  WLSVIWMMWY  WGPSLYSTLS  PFLPLLPIFF  CLWVYI                 226

SEQ ID NO: 5                  moltype = AA  length = 72
FEATURE                       Location/Qualifiers
source                        1..72
                              mol_type = protein
                              note = antigenic loop region J02203 (D, ayw3)
                              organism = synthetic construct
SEQUENCE: 5
QGMLPVCPLI  PGSSTTSTGP  CRTCMTTAQG  TSMYPSCCCT  KPSDGNCTCI  PIPSSWAFGK   60
FLWEWASARF  SW                                                          72

SEQ ID NO: 6                  moltype = AA  length = 72
FEATURE                       Location/Qualifiers
source                        1..72
                              mol_type = protein
                              note = antigenic loop region FJ899792 (D, adw2)
                              organism = synthetic construct
SEQUENCE: 6
QGMLPVCPLI  PGSSTTGTGP  CRTCTTPAQG  TSMYPSCCCT  KPSDGNCTCI  PIPSSWAFGK   60
FLWEWASARF  SW                                                          72

SEQ ID NO: 7                  moltype = AA  length = 72
FEATURE                       Location/Qualifiers
source                        1..72
                              mol_type = protein
                              note = antigenic loop region AM282986 (A)
                              organism = synthetic construct
SEQUENCE: 7
QGMLPVCPLI  PGTTTTSTGP  CKTCTTPAQG  NSMFPSCCCT  KPSDGNCTCI  PIPSSWAFAK   60
YLWEWASVRF  SW                                                          72

SEQ ID NO: 8                  moltype = AA  length = 72
FEATURE                       Location/Qualifiers
source                        1..72
                              mol_type = protein
                              note = antigenic loop region D23678 (B1)
                              organism = synthetic construct
SEQUENCE: 8
QGMLPVCPLI  PGSSTTSTGP  CKTCTTPAQG  TSMFPSCCCT  KPTDGNCTCI  PIPSSWAFAK   60
YLWEWASVRF  SW                                                          72

SEQ ID NO: 9                  moltype = AA  length = 72
FEATURE                       Location/Qualifiers
source                        1..72
                              mol_type = protein
                              note = antigenic loop region AB117758 (C1)
                              organism = synthetic construct
SEQUENCE: 9
QGMLPVCPLL  PGTSTTSTGP  CKTCTIPAQG  TSMFPSCCCT  KPSDGNCTCI  PIPSSWAFAR   60
FLWEWASVRF  SW                                                          72

SEQ ID NO: 10                 moltype = AA  length = 72
FEATURE                       Location/Qualifiers
source                        1..72
                              mol_type = protein
                              note = antigenic loop region AB205192 (E)
                              organism = synthetic construct
SEQUENCE: 10
QGMLPVCPLI  PGSSTTSTGP  CRTCTTLAQG  TSMFPSCCCS  KPSDGNCTCI  PIPSSWAFGK   60
FLWEWASARF  SW                                                          72
```

```
SEQ ID NO: 11          moltype = AA  length = 72
FEATURE                Location/Qualifiers
source                 1..72
                       mol_type = protein
                       note = antigenic loop region X69798 (F4)
                       organism = synthetic construct
SEQUENCE: 11
QGMLPVCPLL PGSTTTSTGP CKTCTTLAQG TSMFPSCCCS KPSDGNCTCI PIPSSWALGK  60
YLWEWASARF SW                                                     72

SEQ ID NO: 12          moltype = AA  length = 72
FEATURE                Location/Qualifiers
source                 1..72
                       mol_type = protein
                       note = antigenic loop region AF160501 (G)
                       organism = synthetic construct
SEQUENCE: 12
QGMLPVCPLI PGSSTTSTGP CKTCTTPAQG NSMYPSCCCT KPSDGNCTCI PIPSSWAFAK  60
YLWEWASVRF SW                                                     72

SEQ ID NO: 13          moltype = AA  length = 72
FEATURE                Location/Qualifiers
source                 1..72
                       mol_type = protein
                       note = antigenic loop region AY090454 (H)
                       organism = synthetic construct
SEQUENCE: 13
QGMLPVCPLL PGSTTTSTGP CKTCTTLAQG TSMFPSCCCT KPSDGNCTCI PIPSSWAFGK  60
YLWEWASARF SW                                                     72

SEQ ID NO: 14          moltype = AA  length = 72
FEATURE                Location/Qualifiers
source                 1..72
                       mol_type = protein
                       note = antigenic loop region AF241409 (I)
                       organism = synthetic construct
SEQUENCE: 14
QGMLPVCPLI PGSSTTSTGP CKTCTTPAQG NSMYPSCCCT KPSDGNCTCI PIPSSWAFAK  60
YLWEWASARF SW                                                     72

SEQ ID NO: 15          moltype = AA  length = 72
FEATURE                Location/Qualifiers
source                 1..72
                       mol_type = protein
                       note = antigenic loop region AB486012 (J)
                       organism = synthetic construct
SEQUENCE: 15
QGMLPVCPLL PGSTTTSTGP CRTCTITAQG TSMFPSCCCT KPSDGNCTCI PIPSSWAFAK  60
FLWEWASVRF SW                                                     72

SEQ ID NO: 16          moltype = AA  length = 73
FEATURE                Location/Qualifiers
source                 1..73
                       mol_type = protein
                       note = antigenic loop region HBsAg Y100C/P120T
                       organism = synthetic construct
SEQUENCE: 16
CQGMLPVCPL IPGSSTTGTG TCRTCTTPAQ GTSMYPSCCC TKPSDGNCTC IPIPSSWAFG  60
KFLWEWASAR FSW                                                    73

SEQ ID NO: 17          moltype = AA  length = 72
FEATURE                Location/Qualifiers
source                 1..72
                       mol_type = protein
                       note = antigenic loop region HBsAg P120T
                       organism = synthetic construct
SEQUENCE: 17
QGMLPVCPLI PGSSTTGTGT CRTCTTPAQG TSMYPSCCCT KPSDGNCTCI PIPSSWAFGK  60
FLWEWASARF SW                                                     72

SEQ ID NO: 18          moltype = AA  length = 72
FEATURE                Location/Qualifiers
source                 1..72
                       mol_type = protein
                       note = antigenic loop region HBsAg P120T/S143L
                       organism = synthetic construct
SEQUENCE: 18
QGMLPVCPLI PGSSTTGTGT CRTCTTPAQG TSMYPSCCCT KPLDGNCTCI PIPSSWAFGK  60
```

```
FLWEWASARF SW                                                      72

SEQ ID NO: 19           moltype = AA  length = 72
FEATURE                 Location/Qualifiers
source                  1..72
                        mol_type = protein
                        note = antigenic loop region HBsAg C121S
                        organism = synthetic construct
SEQUENCE: 19
QGMLPVCPLI PGSSTTGTGP SRTCTTPAQG TSMYPSCCCT KPSDGNCTCI PIPSSWAFGK  60
FLWEWASARF SW                                                      72

SEQ ID NO: 20           moltype = AA  length = 72
FEATURE                 Location/Qualifiers
source                  1..72
                        mol_type = protein
                        note = antigenic loop region HBsAg R122D
                        organism = synthetic construct
SEQUENCE: 20
QGMLPVCPLI PGSSTTGTGP CDTCTTPAQG TSMYPSCCCT KPSDGNCTCI PIPSSWAFGK  60
FLWEWASARF SW                                                      72

SEQ ID NO: 21           moltype = AA  length = 72
FEATURE                 Location/Qualifiers
source                  1..72
                        mol_type = protein
                        note = antigenic loop region HBsAg R122I
                        organism = synthetic construct
SEQUENCE: 21
QGMLPVCPLI PGSSTTGTGP CITCTTPAQG TSMYPSCCCT KPSDGNCTCI PIPSSWAFGK  60
FLWEWASARF SW                                                      72

SEQ ID NO: 22           moltype = AA  length = 72
FEATURE                 Location/Qualifiers
source                  1..72
                        mol_type = protein
                        note = antigenic loop region HBsAg T123N
                        organism = synthetic construct
SEQUENCE: 22
QGMLPVCPLI PGSSTTGTGP CRNCTTPAQG TSMYPSCCCT KPSDGNCTCI PIPSSWAFGK  60
FLWEWASARF SW                                                      72

SEQ ID NO: 23           moltype = AA  length = 72
FEATURE                 Location/Qualifiers
source                  1..72
                        mol_type = protein
                        note = antigenic loop region HBsAg Q129H
                        organism = synthetic construct
SEQUENCE: 23
QGMLPVCPLI PGSSTTGTGP CRTCTTPAHG TSMYPSCCCT KPSDGNCTCI PIPSSWAFGK  60
FLWEWASARF SW                                                      72

SEQ ID NO: 24           moltype = AA  length = 72
FEATURE                 Location/Qualifiers
source                  1..72
                        mol_type = protein
                        note = antigenic loop region HBsAg Q129L
                        organism = synthetic construct
SEQUENCE: 24
QGMLPVCPLI PGSSTTGTGP CRTCTTPALG TSMYPSCCCT KPSDGNCTCI PIPSSWAFGK  60
FLWEWASARF SW                                                      72

SEQ ID NO: 25           moltype = AA  length = 72
FEATURE                 Location/Qualifiers
source                  1..72
                        mol_type = protein
                        note = antigenic loop region HBsAg M133H
                        organism = synthetic construct
SEQUENCE: 25
QGMLPVCPLI PGSSTTGTGP CRTCTTPAQG TSHYPSCCCT KPSDGNCTCI PIPSSWAFGK  60
FLWEWASARF SW                                                      72

SEQ ID NO: 26           moltype = AA  length = 72
FEATURE                 Location/Qualifiers
source                  1..72
                        mol_type = protein
                        note = antigenic loop region HBsAg M133L
                        organism = synthetic construct
SEQUENCE: 26
```

```
QGMLPVCPLI PGSSTTGTGP CRTCTTPAQG TSLYPSCCCT KPSDGNCTCI PIPSSWAFGK    60
FLWEWASARF SW                                                       72

SEQ ID NO: 27           moltype = AA  length = 72
FEATURE                 Location/Qualifiers
source                  1..72
                        mol_type = protein
                        note = antigenic loop region HBsAg M133T
                        organism = synthetic construct
SEQUENCE: 27
QGMLPVCPLI PGSSTTGTGP CRTCTTPAQG TSTYPSCCCT KPSDGNCTCI PIPSSWAFGK    60
FLWEWASARF SW                                                       72

SEQ ID NO: 28           moltype = AA  length = 72
FEATURE                 Location/Qualifiers
source                  1..72
                        mol_type = protein
                        note = antigenic loop region HBsAg K141E
                        organism = synthetic construct
SEQUENCE: 28
QGMLPVCPLI PGSSTTGTGP CRTCTTPAQG TSMYPSCCCT EPSDGNCTCI PIPSSWAFGK    60
FLWEWASARF SW                                                       72

SEQ ID NO: 29           moltype = AA  length = 72
FEATURE                 Location/Qualifiers
source                  1..72
                        mol_type = protein
                        note = antigenic loop region HBsAg P142S
                        organism = synthetic construct
SEQUENCE: 29
QGMLPVCPLI PGSSTTGTGP CRTCTTPAQG TSMYPSCCCT KSSDGNCTCI PIPSSWAFGK    60
FLWEWASARF SW                                                       72

SEQ ID NO: 30           moltype = AA  length = 72
FEATURE                 Location/Qualifiers
source                  1..72
                        mol_type = protein
                        note = antigenic loop region HBsAg S143K
                        organism = synthetic construct
SEQUENCE: 30
QGMLPVCPLI PGSSTTGTGP CRTCTTPAQG TSMYPSCCCT KPKDGNCTCI PIPSSWAFGK    60
FLWEWASARF SW                                                       72

SEQ ID NO: 31           moltype = AA  length = 72
FEATURE                 Location/Qualifiers
source                  1..72
                        mol_type = protein
                        note = antigenic loop region HBsAg D144A
                        organism = synthetic construct
SEQUENCE: 31
QGMLPVCPLI PGSSTTGTGP CRTCTTPAQG TSMYPSCCCT KPSAGNCTCI PIPSSWAFGK    60
FLWEWASARF SW                                                       72

SEQ ID NO: 32           moltype = AA  length = 72
FEATURE                 Location/Qualifiers
source                  1..72
                        mol_type = protein
                        note = antigenic loop region HBsAg G145R
                        organism = synthetic construct
SEQUENCE: 32
QGMLPVCPLI PGSSTTGTGP CRTCTTPAQG TSMYPSCCCT KPSDRNCTCI PIPSSWAFGK    60
FLWEWASARF SW                                                       72

SEQ ID NO: 33           moltype = AA  length = 72
FEATURE                 Location/Qualifiers
source                  1..72
                        mol_type = protein
                        note = antigenic loop region HBsAg N146A
                        organism = synthetic construct
SEQUENCE: 33
QGMLPVCPLI PGSSTTGTGP CRTCTTPAQG TSMYPSCCCT KPSDGACTCI PIPSSWAFGK    60
FLWEWASARF SW                                                       72

SEQ ID NO: 34           moltype = AA  length = 8
FEATURE                 Location/Qualifiers
source                  1..8
                        mol_type = protein
                        note = antibody HBC34 CDRH1 aa
                        organism = synthetic construct
```

-continued

```
SEQUENCE: 34
GRIFRSFY                                                                         8

SEQ ID NO: 35           moltype = AA  length = 7
FEATURE                 Location/Qualifiers
source                  1..7
                        mol_type = protein
                        note = antibody HBC34 CDRH2 aa
                        organism = synthetic construct
SEQUENCE: 35
NQDGSEK                                                                          7

SEQ ID NO: 36           moltype = AA  length = 12
FEATURE                 Location/Qualifiers
source                  1..12
                        mol_type = protein
                        note = antibody HBC34 CDRH3 aa
                        organism = synthetic construct
SEQUENCE: 36
AAWSGNSGGM DV                                                                   12

SEQ ID NO: 37           moltype = AA  length = 6
FEATURE                 Location/Qualifiers
source                  1..6
                        mol_type = protein
                        note = antibody HBC34 CDRL1 aa
                        organism = synthetic construct
SEQUENCE: 37
KLGNKN                                                                           6

SEQ ID NO: 38           moltype =     length =
SEQUENCE: 38
000

SEQ ID NO: 39           moltype = AA  length = 9
FEATURE                 Location/Qualifiers
source                  1..9
                        mol_type = protein
                        note = antibody HBC34 CDRL2 long aa
                        organism = synthetic construct
SEQUENCE: 39
VIYEVKYRP                                                                        9

SEQ ID NO: 40           moltype = AA  length = 9
FEATURE                 Location/Qualifiers
source                  1..9
                        mol_type = protein
                        note = antibody HBC34 CDRL3 aa
                        organism = synthetic construct
SEQUENCE: 40
QTWDSTTVV                                                                        9

SEQ ID NO: 41           moltype = AA  length = 119
FEATURE                 Location/Qualifiers
source                  1..119
                        mol_type = protein
                        note = antibody HBC34 VH aa
                        organism = synthetic construct
SEQUENCE: 41
ELQLVESGGG WVQPGGSQRL SCAASGRIFR SFYMSWVRQA PGKGLEWVAT INQDGSEKLY               60
VDSVKGRFTI SRDNAKNSLF LQMNNLRVED TAVYYCAAWS GNSGGMDVWG QGTTVSVSS               119

SEQ ID NO: 42           moltype = AA  length = 106
FEATURE                 Location/Qualifiers
source                  1..106
                        mol_type = protein
                        note = antibody HBC34 VL aa
                        organism = synthetic construct
SEQUENCE: 42
SYELTQPPSV SVSPGQTVSI PCSGDKLGNK NVCWFQHKPG QSPVLVIYEV KYRPSGIPER               60
FSGSNSGNTA TLTISGTQAM DEAAYFCQTW DSTTVVFGGG TRLTVL                             106

SEQ ID NO: 43           moltype = DNA  length = 24
FEATURE                 Location/Qualifiers
misc_feature            1..24
                        note = antibody HBC34 CDRH1 nuc
source                  1..24
                        mol_type = other DNA
                        organism = synthetic construct
```

```
SEQUENCE: 43
ggacgcatct ttagaagttt ttac                                              24

SEQ ID NO: 44           moltype = DNA  length = 24
FEATURE                 Location/Qualifiers
misc_feature            1..24
                        note = antibody HBC34 CDRH2 nuc
source                  1..24
                        mol_type = other DNA
                        organism = synthetic construct
SEQUENCE: 44
ataaccaag atggaagtga gaaa                                               24

SEQ ID NO: 45           moltype = DNA  length = 36
FEATURE                 Location/Qualifiers
misc_feature            1..36
                        note = antibody HBC34 CDRH3 nuc
source                  1..36
                        mol_type = other DNA
                        organism = synthetic construct
SEQUENCE: 45
gcggcttgga gcggcaatag tgggggtatg gacgtc                                 36

SEQ ID NO: 46           moltype = DNA  length = 18
FEATURE                 Location/Qualifiers
misc_feature            1..18
                        note = antibody HBC34 CDRL1 nuc
source                  1..18
                        mol_type = other DNA
                        organism = synthetic construct
SEQUENCE: 46
aaattgggga ataaaaat                                                     18

SEQ ID NO: 47           moltype =      length =
SEQUENCE: 47
000

SEQ ID NO: 48           moltype = DNA  length = 27
FEATURE                 Location/Qualifiers
misc_feature            1..27
                        note = antibody HBC34 CDRL2 long nuc
source                  1..27
                        mol_type = other DNA
                        organism = synthetic construct
SEQUENCE: 48
gtcatctatg aggttaaata ccgcccc                                           27

SEQ ID NO: 49           moltype = DNA  length = 27
FEATURE                 Location/Qualifiers
misc_feature            1..27
                        note = antibody HBC34 CDRL3 nuc
source                  1..27
                        mol_type = other DNA
                        organism = synthetic construct
SEQUENCE: 49
cagacgtggg acagcaccac tgtggtg                                           27

SEQ ID NO: 50           moltype = DNA  length = 357
FEATURE                 Location/Qualifiers
misc_feature            1..357
                        note = antibody HBC34 VH nuc
source                  1..357
                        mol_type = other DNA
                        organism = synthetic construct
SEQUENCE: 50
gaactgcagc tggtggagtc tgggggaggc tgggtccagc cggggggtc ccagagactg        60
tcctgtgcag cctctggacg catctttaga agttttaca tgagctgggt ccgccaggcc       120
ccagggaagg ggctggagtg ggtggccact ataaaccaag atggaagtga gaaattatat      180
gtggactctg tgaagggccg attcaccatc tccagagaca cgccaagaa ctcactattt      240
ctgcaaatga acaacctgag agtcgaggac acggccgttt attactgcgc ggcttggagc     300
ggcaatagtg gggtatgga cgtctgggc caggggacca cggtctccgt ctcctca          357

SEQ ID NO: 51           moltype = DNA  length = 318
FEATURE                 Location/Qualifiers
misc_feature            1..318
                        note = antibody HBC34 VL nuc
source                  1..318
                        mol_type = other DNA
                        organism = synthetic construct
```

```
SEQUENCE: 51
tcctatgagc tgactcagcc accctcagtg tccgtgtccc caggacagac agtcagcatc  60
ccctgctctg gagataaatt ggggaataaa aatgtttgct ggtttcagca taagccaggc  120
cagtcccctg tgttggtcat ctatgaggtt aaataccgcc cctcggggat tcctgagcga  180
ttctctggct ccaactctgg gaacacagcc actctgacca tcagcgggac ccaggctatg  240
gatgaggctg cctatttctg tcagacgtgg gacagcacca ctgtggtgtt cggcggaggg  300
accaggctga ccgtccta                                                318

SEQ ID NO: 52           moltype = AA  length = 33
FEATURE                 Location/Qualifiers
VARIANT                 1
                        note = X is substituted with C
VARIANT                 17
                        note = X is substituted with C
VARIANT                 33
                        note = X is substituted with C
source                  1..33
                        mol_type = protein
                        organism = synthetic construct
SEQUENCE: 52
XGSSTTSTGP CRTCMTXPSD GNATAIPIPS SWX                               33

SEQ ID NO: 53           moltype = AA  length = 15
FEATURE                 Location/Qualifiers
source                  1..15
                        mol_type = protein
                        organism = synthetic construct
SEQUENCE: 53
TSTGPCRTCM TTAQG                                                   15

SEQ ID NO: 54           moltype = AA  length = 26
FEATURE                 Location/Qualifiers
source                  1..26
                        mol_type = protein
                        organism = synthetic construct
SEQUENCE: 54
GMLPVCPLIP GSSTTSTGPC RTCMTT                                       26

SEQ ID NO: 55           moltype = AA  length = 33
FEATURE                 Location/Qualifiers
VARIANT                 1
                        note = X is substituted with C
VARIANT                 17
                        note = X is substituted with C
VARIANT                 33
                        note = X is substituted with C
source                  1..33
                        mol_type = protein
                        organism = synthetic construct
SEQUENCE: 55
XSMYPSASAT KPSDGNXTGP CRTCMTTAQG TSX                               33

SEQ ID NO: 56           moltype = AA  length = 11
FEATURE                 Location/Qualifiers
source                  1..11
                        mol_type = protein
                        note = antigenic loop region fragment (amino acids 120 -
                         130 of the Sdomain of HBsAg HBV-D J02203)
                        organism = synthetic construct
SEQUENCE: 56
PCRTCMTTAQ G                                                       11

SEQ ID NO: 57           moltype = AA  length = 11
FEATURE                 Location/Qualifiers
VARIANT                 3
                        note = X may be any amino acid, preferably X is R or K
VARIANT                 6
                        note = X may be any amino acid, preferably X is M or T
VARIANT                 7
                        note = X may be any amino acid, preferably X is T or I
VARIANT                 8
                        note = X may be any amino acid, preferably X is T, P or L
source                  1..11
                        mol_type = protein
                        note = epitope
                        organism = synthetic construct
SEQUENCE: 57
PCXTCXXXAQ G                                                       11
```

| SEQ ID NO: 58 | moltype = AA  length = 9 |
|---|---|
| FEATURE | Location/Qualifiers |
| source | 1..9 |
| | mol_type = protein |
| | note = CDRL3 v7 and CDRL3 v23 (aa) |
| | organism = synthetic construct |

SEQUENCE: 58
QTFDSTTVV                                                                                      9

| SEQ ID NO: 59 | moltype = AA  length = 106 |
|---|---|
| FEATURE | Location/Qualifiers |
| source | 1..106 |
| | mol_type = protein |
| | note = VL v7 |
| | organism = synthetic construct |

SEQUENCE: 59
SYELTQPPSV SVSPGQTVSI PCSGDKLGNK NVCWFQHKPG QSPVLVIYEV KYRPSGIPER    60
FSGSNSGNTA TLTISGTQAM DEAAYFCQTF DSTTVVFGGG TRLTVL                 106

| SEQ ID NO: 60 | moltype = DNA  length = 18 |
|---|---|
| FEATURE | Location/Qualifiers |
| misc_feature | 1..18 |
| | note = CDRL1 v7 and CDRL1 v23 (nuc) |
| source | 1..18 |
| | mol_type = other DNA |
| | organism = synthetic construct |

SEQUENCE: 60
aagctgggga acaaaaat                                                                           18

| SEQ ID NO: 61 | moltype =    length = |
|---|---|

SEQUENCE: 61
000

| SEQ ID NO: 62 | moltype = DNA  length = 27 |
|---|---|
| FEATURE | Location/Qualifiers |
| misc_feature | 1..27 |
| | note = CDRL2 long v7 and CDRL2 long v23 nuc |
| source | 1..27 |
| | mol_type = other DNA |
| | organism = synthetic construct |

SEQUENCE: 62
gtcatctacg aggtgaaata tcggcct                                                                 27

| SEQ ID NO: 63 | moltype = DNA  length = 27 |
|---|---|
| FEATURE | Location/Qualifiers |
| misc_feature | 1..27 |
| | note = CDRL3 v7 and CDRL3 v23 nuc |
| source | 1..27 |
| | mol_type = other DNA |
| | organism = synthetic construct |

SEQUENCE: 63
cagacattcg attccaccac agtggtc                                                                 27

| SEQ ID NO: 64 | moltype = DNA  length = 318 |
|---|---|
| FEATURE | Location/Qualifiers |
| misc_feature | 1..318 |
| | note = VL v7 nuc |
| source | 1..318 |
| | mol_type = other DNA |
| | organism = synthetic construct |

SEQUENCE: 64
tcttacgagc tgacacagcc acctagcgtg tccgtctctc caggacagac cgtgtccatc    60
ccttgctctg gcgacaagct ggggaacaaa aatgtctgtt ggttccagca caagccaggg   120
cagagtcccg tgctggtcat ctacgaggtg aaatatcggc cttcaggaat tccagaacgg   180
ttcagcggat caaacagcgg caatactgca accctgacaa ttagcgggac ccaggccatg   240
gacgaagccg cttatttctg ccagacattc gattccacca gtggtcctt tggcggggga   300
actaggctga ccgtgctg                                                 318

| SEQ ID NO: 65 | moltype = AA  length = 106 |
|---|---|
| FEATURE | Location/Qualifiers |
| source | 1..106 |
| | mol_type = protein |
| | note = VL v23 aa |
| | organism = synthetic construct |

SEQUENCE: 65
SYELTQPPSV SVSPGQTASI TCSGDKLGNK NACWYQQKPG QSPVLVIYEV KYRPSGIPER    60
FSGSNSGNTA TLTISGTQAM DEADYYCQTF DSTTVVFGGG TKLTVL                 106

| SEQ ID NO: 66 | moltype = AA  length = 8 |
|---|---|

```
FEATURE                 Location/Qualifiers
source                  1..8
                        mol_type = protein
                        note = HBC34wt CDRH2 aa
                        organism = synthetic construct
SEQUENCE: 66
INQDGSEK                                                                8

SEQ ID NO: 67           moltype = AA  length = 119
FEATURE                 Location/Qualifiers
source                  1..119
                        mol_type = protein
                        note = HBC34 v31, HBC34 v32 and HBC34 v33 VH
                        organism = synthetic construct
SEQUENCE: 67
EVQLVESGGG LVQPGGSLRL SCAASGRIFR SFYMSWVRQA PGKGLEWVAN INQDGSEKLY   60
VDSVKGRFTI SRDNAKNSLF LQMNNLRVED TAVYYCAAWS GNSGGMDVWG QGTTVTVSS    119

SEQ ID NO: 68           moltype = DNA  length = 357
FEATURE                 Location/Qualifiers
misc_feature            1..357
                        note = HBC34 v31, HBC34 v32 and HBC34 v33 VH (nuc)
source                  1..357
                        mol_type = other DNA
                        organism = synthetic construct
SEQUENCE: 68
gaggtgcagc tggtggaatc cggcggggga ctggtgcagc ctggcggctc actgagactg    60
agctgtgcag cttctggaag aatcttcaga tctttttaca tgagttgggt gagacaggct   120
cctgggaagg gactggagtg ggtcgcaaac atcaatcagg acggatcaga aaagctgtat   180
gtggatagcg tcaaaggcag gttcactatt tcccgcgaca acgccaaaaa ttctctgttt   240
ctgcagatga acaatctgcg ggtggaggat accgctgtct actattgtgc agcctggtct   300
ggcaacagtg gaggcatgga cgtgtgggga cagggaacca cagtgacagt cagctcc     357

SEQ ID NO: 69           moltype = DNA  length = 318
FEATURE                 Location/Qualifiers
misc_feature            1..318
                        note = VL v23 nuc
source                  1..318
                        mol_type = other DNA
                        organism = synthetic construct
SEQUENCE: 69
tcttacgagc tgacacagcc ccctagcgtg tccgtctctc caggccagac agcatccatc    60
acttgctctg gcgacaagct ggggaacaaa aatgcctgtt ggtatcagca gaagccaggg   120
cagagtcccg tgctggtcat ctacgaggtg aaatatcggc cttcaggaat tccagaaaga   180
ttcagtggat caaacagcgg caatactgct accctgacaa ttagcgggac ccaggccatg   240
gacgaagctg attactattg ccagacattc gattccacca cagtggtctt tggcggggga   300
actaagctga ccgtgctg                                                318

SEQ ID NO: 70           moltype = DNA  length = 357
FEATURE                 Location/Qualifiers
misc_feature            1..357
                        note = HBC34 wt VH codon optimized
source                  1..357
                        mol_type = other DNA
                        organism = synthetic construct
SEQUENCE: 70
gaactgcagc tggtcgaatc aggaggaggg tgggtccagc ccggagggag ccagagactg    60
tcttgtgccg catcagggag gatcttcagg agcttctaca gtcctgggt gcgcaggca    120
ccaggcaagg gactggagtg ggtcgccacc atcaaccagg acggatctga aaagctgtat   180
gtggatagtg tcaaaggccg gttcacaatt agcagagaca acgctaaaaa ttctctgttt   240
ctgcagatga acaatctgcg agtggaggat accgccgtct actattgcgc cgcttggtct   300
ggcaacagcg gcgggatgga tgtctggggg cagggcacaa cagtgagcgt ctcttcc     357

SEQ ID NO: 71           moltype = DNA  length = 318
FEATURE                 Location/Qualifiers
misc_feature            1..318
                        note = HBC34 wt VL codon optimized
source                  1..318
                        mol_type = other DNA
                        organism = synthetic construct
SEQUENCE: 71
tcatacgaac tgactcagcc tccctccgtc tccgtctcac ctggacagac cgtctcaatc    60
ccctgctccg gcgataaact gggcaacaag aacgtgtgct ggttccagca aaacccgga   120
cagagtcctg tgctggtcat ctacgaggtc aagtatcggc caagcggcat tcccgaaaga   180
ttcagcggct ccaactctgg gaataccgca acactgacta tctctggaac ccaggcaatg   240
gacgaggcag cttactttg ccagacttgg gattcaacta ctgtcgtgtt cggcggcgga   300
actagactga ctgtcctg                                                318

SEQ ID NO: 72           moltype = DNA  length = 24
```

```
FEATURE                 Location/Qualifiers
misc_feature            1..24
                        note = HBC34 wt CDRH1 codon optimized
source                  1..24
                        mol_type = other DNA
                        organism = synthetic construct
SEQUENCE: 72
gggaggatct tcaggagctt ctac                                            24

SEQ ID NO: 73           moltype = DNA   length = 24
FEATURE                 Location/Qualifiers
misc_feature            1..24
                        note = HBC34 wt CDRH2 codon optimized
source                  1..24
                        mol_type = other DNA
                        organism = synthetic construct
SEQUENCE: 73
atcaaccagg acggatctga aaag                                            24

SEQ ID NO: 74           moltype = DNA   length = 36
FEATURE                 Location/Qualifiers
misc_feature            1..36
                        note = HBC34 wt CDRH3 codon optimized
source                  1..36
                        mol_type = other DNA
                        organism = synthetic construct
SEQUENCE: 74
gccgcttggt ctggcaacag cggcgggatg gatgtc                               36

SEQ ID NO: 75           moltype = DNA   length = 18
FEATURE                 Location/Qualifiers
misc_feature            1..18
                        note = HBC34 wt CDRL1 codon optimized
source                  1..18
                        mol_type = other DNA
                        organism = synthetic construct
SEQUENCE: 75
aaactgggca acaagaac                                                   18

SEQ ID NO: 76           moltype =   length =
SEQUENCE: 76
000

SEQ ID NO: 77           moltype = DNA   length = 27
FEATURE                 Location/Qualifiers
misc_feature            1..27
                        note = HBC34 wt CDRL2 long codon optimized
source                  1..27
                        mol_type = other DNA
                        organism = synthetic construct
SEQUENCE: 77
gtcatctacg aggtcaagta tcggcca                                         27

SEQ ID NO: 78           moltype = DNA   length = 27
FEATURE                 Location/Qualifiers
misc_feature            1..27
                        note = HBC34 wt CDRL3 codon optimized
source                  1..27
                        mol_type = other DNA
                        organism = synthetic construct
SEQUENCE: 78
cagacttggg attcaactac tgtcgtg                                         27

SEQ ID NO: 79           moltype = AA   length = 5
FEATURE                 Location/Qualifiers
source                  1..5
                        mol_type = protein
                        note = linker
                        organism = synthetic construct
SEQUENCE: 79
GGSGG                                                                  5

SEQ ID NO: 80           moltype = AA   length = 7
FEATURE                 Location/Qualifiers
source                  1..7
                        mol_type = protein
                        note = epitope
                        organism = synthetic construct
SEQUENCE: 80
```

```
TGPCRTC                                                             7

SEQ ID NO: 82       moltype = AA  length = 25
FEATURE             Location/Qualifiers
VARIANT             2
                    note = cysteine coupled to acetamidomethyl
VARIANT             21
                    note = cysteine coupled to acetamidomethyl
VARIANT             24
                    note = cysteine coupled to acetamidomethyl
source              1..25
                    mol_type = protein
                    note = discontinuousepitope mimic
                    organism = synthetic construct
SEQUENCE: 82
CCIPIPSSWA FGCSTTSTGP CRTCC                                         25

SEQ ID NO: 81       moltype = AA  length = 7
FEATURE             Location/Qualifiers
source              1..7
                    mol_type = protein
                    note = epitope
                    organism = synthetic construct
SEQUENCE: 81
GNCTCIP                                                             7

SEQ ID NO: 83       moltype = AA  length = 28
FEATURE             Location/Qualifiers
VARIANT             4
                    note = cysteine coupled to acetamidomethyl
VARIANT             6
                    note = cysteine coupled to acetamidomethyl
VARIANT             24
                    note = cysteine coupled to acetamidomethyl
VARIANT             27
                    note = cysteine coupled to acetamidomethyl
source              1..28
                    mol_type = protein
                    note = discontinuous epitope mimic
                    organism = synthetic construct
SEQUENCE: 83
CGNCTCIPIP SSWAFCSTTS TGPCRTCC                                      28

SEQ ID NO: 84       moltype = AA  length = 17
FEATURE             Location/Qualifiers
VARIANT             13
                    note = cysteine coupled to acetamidomethyl
VARIANT             16
                    note = cysteine coupled to acetamidomethyl
source              1..17
                    mol_type = protein
                    note = looped epitope mimic
                    organism = synthetic construct
SEQUENCE: 84
CGGGCSTTST GPCRTCC                                                  17

SEQ ID NO: 85       moltype = AA  length = 11
FEATURE             Location/Qualifiers
source              1..11
                    mol_type = protein
                    note = epitope
                    organism = synthetic construct
SEQUENCE: 85
STTSTGPCRT C                                                        11

SEQ ID NO: 86       moltype = AA  length = 15
FEATURE             Location/Qualifiers
source              1..15
                    mol_type = protein
                    note = epitope
                    organism = synthetic construct
SEQUENCE: 86
GNCTCIPIPS SWAFC                                                    15

SEQ ID NO: 87       moltype = AA  length = 14
FEATURE             Location/Qualifiers
source              1..14
                    mol_type = protein
                    note = epitope
```

```
                             organism = synthetic construct
SEQUENCE: 87
GNCTCIPIPS SWAF                                                          14

SEQ ID NO: 88              moltype = AA  length = 5
FEATURE                    Location/Qualifiers
source                     1..5
                           mol_type = protein
                           note = epitope
                           organism = synthetic construct
SEQUENCE: 88
PCRXC                                                                     5

SEQ ID NO: 89              moltype = AA  length = 19
FEATURE                    Location/Qualifiers
source                     1..19
                           mol_type = protein
                           note = chimeric hinge sequence
                           organism = synthetic construct
SEQUENCE: 89
ESKYGPPCPP CPAPPVAGP                                                     19

SEQ ID NO: 90              moltype = AA  length = 13
FEATURE                    Location/Qualifiers
source                     1..13
                           mol_type = protein
                           note = residues used for substitution in sequences
                           organism = synthetic construct
SEQUENCE: 90
AEFGHKLPQR SVY                                                           13

SEQ ID NO: 91              moltype = AA  length = 19
FEATURE                    Location/Qualifiers
source                     1..19
                           mol_type = protein
                           note = Chimeric hinge
                           organism = synthetic construct
SEQUENCE: 91
ESKYGPPCPP CPAPPVAGP                                                     19

SEQ ID NO: 92              moltype = AA  length = 13
FEATURE                    Location/Qualifiers
source                     1..13
                           mol_type = protein
                           organism = synthetic construct
SEQUENCE: 92
AEFGHKLPQR SVY                                                           13
```